(12) United States Patent
Noda et al.

(10) Patent No.: US 9,074,215 B2
(45) Date of Patent: Jul. 7, 2015

(54) METHOD FOR PRODUCTION OF CHRYSANTHEMUM PLANT HAVING DELPHINIDIN-CONTAINING PETALS

(75) Inventors: Naonobu Noda, Tsukuba (JP); Ryutaro Aida, Tsukuba (JP); Sanae Sato, Tsukuba (JP); Akemi Ohmiya, Tsukuba (JP); Yoshikazu Tanaka, Osaka (JP)

(73) Assignees: Incorporated Adminstrative Agency, National Agriculture and Food Research Organization, Tsukuba-shi, Ibaraki (JP); Suntory Holdings Limited, Osaka-shi, Osaka (JP)

( * ) Notice: Subject to any disclaimer, the term of this patent is extended or adjusted under 35 U.S.C. 154(b) by 713 days.

(21) Appl. No.: 13/265,688

(22) PCT Filed: Mar. 9, 2010

(86) PCT No.: PCT/JP2010/053904
§ 371 (c)(1),
(2), (4) Date: Dec. 30, 2011

(87) PCT Pub. No.: WO2010/122849
PCT Pub. Date: Oct. 28, 2010

(65) Prior Publication Data
US 2012/0096589 A1   Apr. 19, 2012

(30) Foreign Application Priority Data

Apr. 24, 2009  (JP) ................. 2009-107054

(51) Int. Cl.
*C12N 15/82* (2006.01)
*C12N 9/02* (2006.01)
*A01H 5/02* (2006.01)

(52) U.S. Cl.
CPC .......... *C12N 15/8243* (2013.01); *A01H 5/0255* (2013.01); *C12N 9/0071* (2013.01); *C12N 15/825* (2013.01)

(58) Field of Classification Search
USPC ....................................................... 800/282
See application file for complete search history.

(56) References Cited

U.S. PATENT DOCUMENTS

| | | | |
|---|---|---|---|
| 5,948,955 A * | 9/1999 | Holton et al. ................. | 800/298 |
| 6,573,429 B1 | 6/2003 | Shinmyo et al. | |
| 7,105,719 B1 | 9/2006 | Ashikari et al. | |

FOREIGN PATENT DOCUMENTS

| | | |
|---|---|---|
| EP | 1 652 916 | 5/2006 |
| JP | 2003-79372 | 3/2003 |
| JP | 2004-65096 | 3/2004 |
| KR | 10-0726874 | 6/2007 |
| WO | 94/28140 | 12/1994 |
| WO | 96/25500 | 8/1996 |
| WO | 01/72984 | 10/2001 |
| WO | 2005/017147 | 2/2005 |
| WO | 2009/062253 | 5/2009 |

OTHER PUBLICATIONS

Ukiya et al. (Constitutents of Compositae Plants. 2. Triterpene Diols, Triols, and Their 3-o-Fatty Acid Esters from Edible Chrysanthemum Flower Extract and Their Anti-inflammatory Effects, 49 J. Agric. Food Chem., 3187-3197 (2001)).*
Y. Tanaka et al., "Genetic engineering in floriculture," Plant Cell, Tissue and Organ Culture, Kluwer Academic Publishers, DO, vol. 80, No. 1, Jan. 1, 2005, pp. 1-24.
Supplementary European Search Report issued in EP 10766908.7 dated Jan. 23, 2013.
Tanaka, Y., "Flower colour and cytochromes P450", Phytochem Rev., 2006, vol. 5, p. 283-291.
Kanno, Y., et al., "Histochemical Analysis of Gene Expression Directed by the Promoter of a Flavanone 3-Hydroxylase Gene from *Dendranthema x grandiflorum* in *Petunia hybrida*", Journal of the Japanese Soceity for Horticultural Science, 2001, vol. 70, separate vol. 2, p. 193.
Kim, Y., et al., "Identification and Characterization of Flavanone 3-Hydroxylase (F3H) Gene from *Dendranthema grandiflora*", J. Kor. Soc. Hort. Sci., 2002, vol. 43, p. 666-670.
Aida, R., et al. "Improved translation efficiency in chrysanthemum and torenia with a translational enhancer derived from the tobacco *alcohol dehydrogenase* gene", Plant Biotechnology, 2008, vol. 25, p. 69-75.
Seo, J., et al., "Co-expression of *flavonoid 3', 5'-hydroxilase* and flavonoid 3'-*hydroxiylase* Accelerates Decolorization in Transgenic Chrysanthemum Petals", 2007, vol. 50, p. 626-631.
anno, Y., et al., "Expression of Anthocyanin Biosynthetic Genes in 3 cultivars of Chrysanthemum", Journal of the Japanese Society for Horticultural Science, 2000, vol. 69, separate vol. 1, p. 355.
Tanaka, Y., et al., "Biosynthesis of plant pigments: anthocyanins, betalains and carotenoids", The Plant Journal, 2008, vol. 54, p. 733-749.
Kondo, T., et al., "Structure of Malonylshisonin, a Genuine Pigment in Purple Leaves of *Perilla ocimoides* L. var. *crispa* Benth", Agricultural Biological Chemistry, 1989, vol. 53, p. 797-800.

(Continued)

*Primary Examiner* — Ashwin Mehta
*Assistant Examiner* — Rebecca Stephens
(74) *Attorney, Agent, or Firm* — Drinker Biddle & Reath LLP

(57) ABSTRACT

Disclosed are: a method for producing a chrysanthemum plant having delphinidin-containing petals using a transcriptional regulatory region for a chrysanthemum-derived flavanone 3-hydroxylase (F3H) gene; and a chrysanthemum plant, a progeny or a vegetative proliferation product of the plant, or a part or a tissue of the plant, the progeny or the vegetative proliferation product, and particularly a petal or a cut flower of the plant. In the method for producing a chrysanthemum plant having delphinidin-containing petals, a flavonoid 3',5'-hydroxylase (F3'5'H) is caused to be expressed in a chrysanthemum plant using a transcriptional regulatory region for a chrysanthemum-derived flavanone 3-hydroxylase (F3H) gene.

8 Claims, 4 Drawing Sheets

(56) References Cited

OTHER PUBLICATIONS

Mitsuhara, I., et al., "Efficient Promoter Cassettes for Enhanced Expression of Foreign Genes in Dicotyledonous and Monocotyledonous Plants", Plant Cell Physiology, 1996, vol. 37, p. 49-59.

Comai, L., et al., "Novel and useful properties of a chimeric plant promoter combining CaMV 35S and MAS elements", Plant Molecular Biology, 1990, vol. 15, p. 373-381.

Stam, M., et al., "The Silence of Genes in Transgenic Plants", Annals of Botany, 1997, vol. 79, p. 3-12.

Nozaki, K., et al., "Effects of high temperature on flower colour and anthocyanin content in pink flower genotypes of greenhouse chrysanthemum (Chrysanthemum morifolium Ramat.)", Journal of Horticultural Science & Biotechnology, 2006, vol. 81, p. 728-734.

Takatsu, Y., et al., "Transgene inactivation in Agrobacterium-mediated chrysanthemum (Dendranthema grandiflorum (Ramat.) Kitamura) transformants", Plant Biotechnology, 2000, vol. 17, p. 241-245.

Aida, R., et al., "Efficient Transgene Expression in Chrysanthemum, Dendranthema grandiflorum (Ramat.) Kitamura, by Using the Promoter of a Gene for Chrysanthemum Chlorophyll-a/b-binding Protein", Breeding Science, 2004, vol. 54, p. 51-58.

Aida, R., et al., "Efficient Transgene Expression in Chrysanthemum, Chrysanthemum morifolium Ramat., with the Promoter of a Gene for Tobacco Elongation Factor 1 α Protein", Japan Agricultural Research Quarterly, 2005, vol. 39, p. 269-274.

Narumi, T., et al., "Transformation of chrysanthemum with mutated ethylene receptor genes: mDG-ERS1 transgenes conferring reduced ethylene sensitivity and characterization of the transformants", Postharvest Biology and Technology, 2005, vol. 37, p. 101-110.

Aida, R., et al., "Chrysanthemum flower shape modification by suppression of chrysanthemum-AGAMOUSgene", Plant Biotechnology, 2008, vol. 25, p. 55-59.

Aida, R., et al., "Improved translation efficiency in chrysanthemum and torenia with a translational enhancer derived form the tobacco alcohol dehydrogenase gene", Plant Biotechnology, 2008, vol. 25, p. 69-75.

Courtney-Gutterson, N., et al, "Modification of Flower Color in Florist's Chrysanthemum: Production of a White-Flowering Variety Through Molecular Genetics", Bio/Technology, Mar. 1994, vol. 12, p. 268-271.

Ohmiya, A., et al., "Carotenoid Cleavage Dioxygenase (CmCCD4a) Contributes to White Color Formation in Chrysanthemum Petals[1][oa]", Plant Physiology, Nov. 2006, vol. 142, pp. 1193-1201.

Annadana, S., et al., "The potato Lhca3.St.1 promoter confers high and stable transgene expression in chrysanthemum, in contrast to CaMV-based promoters", Molecular Breeding, 2001, vol. 8, p. 335-344.

Annadana, S., et al., "Cloning of the chrysanthemum UEP1 promoter and comparative expression in florets and leaves of Dendranthema grandiflora", Transgenic Research, 2002, vol. 11, p. 437-445.

Gallie, D. R., et al., "The 5'-leader sequence of tobacco mosaic virus RNA enhances the expression of foreign gene transcripts in vitro and in vivo", Nucleic Acids Research, 1987, vol. 15, No. 8, p. 3257-3273.

Kim, Y., "Identification and characterization of flavonoid 3',5'-hydroxylase gene in transgenic Chrysanthemum jawadskii.", Plant Biology, Aug. 1997, p. 299.

Park, S. Y., et al., GenBank Accession: U86837 [online], Mar. 8, 1999. {http://www.ncbi.nlm.nih.gov/sviewer.fcgi?2801406:NCBI:994364}.

International Search Report issued on May 11, 2010 in International PCT Application No. PCT/JP2010/053904 filed Mar. 9, 2010.

Kim et al. (1994) Plant Mol. Biol. 24: 105-117.

Kanno (2002) Nat'l Agricultural Res. Center 16: 281-282.

Noda et al. (2013) Plant Cell Physiol. 54: 1684-1695.

* cited by examiner

SEQUENCE LISTING

<160> NUMBER OF SEQ ID NOS: 87

<210> SEQ ID NO 1
<211> LENGTH: 1096
<212> TYPE: DNA
<213> ORGANISM: Perilla frutescens
<220> FEATURE:
<221> NAME/KEY: promoter
<222> LOCATION: (1)..(1096)
<223> OTHER INFORMATION: anthocyanin 3-acyl transferase promoter

<400> SEQUENCE: 1

```
aactattatg atcccacaga gttttttgaca gatgagtctt caggaggaga tgctgaacct      60
tttcactact ctactgaacg catcacaagt ttatcggctt atatgactaa tagggatcaa     120
cttcacaaca gagaggctca tagagctctt aaagaggatt tgatcgagca catatggaaa     180
aaattcggca ctaactaaat atataattta cgttttatgc actcgtaatt taaaatttca     240
tgtgtctcat tgtagtttat ttaattatgt tttcactctt gtaattttta ttttgttgtg     300
aagtaaatta tgaatttata attatatggg taatttttg  ataattatgc aattaaaaat     360
aattaatatt ttttaaatgc aagagaaaaa tgttatttta ataacatgtt cttattaaaa     420
aataaaatga taaatatttt atgtaggttg ggagaaaatg aaaaaataat attttatttg     480
aaggttgggt tggatgaggt cactgatggg agtataaata atactccctc cgtcccataa     540
ttattgtcca ttattccttt tgggatgtc  ccaaaattat agtcctattc taaattggga     600
ttgtatttaa atattctttt acaaatataa ccctatttga tatagtatga atgcaattaa     660
tatagtaaaa aaataagggc aatataggat aattattgta aattgtatat ttccaataca     720
tattaaatgt gatttcttaa tctgtgtgaa aataggaagt ggactataat tatgggacgg     780
agggagtata agttggagg  ttgtggatgt ggaggagaaa gaattaata  ttttatttaa     840 agattggatt aaaggaggtc actgatgtgg gtagtcttag aggaaatgta gtcttagagg     900
aaatctgccc agcaaaataa aataataagt aaataaataa actaaatatg tattgaatgc     960
gacatctagc aatatagcca catatatagt gcagtagcac gcagcgctcg ttactcgtca    1020
gtcgtcaaag aatggtaagt atagaaaagc atctttaaat aacacaccaa aaaccacagc    1080
tacgttcaac accgcc                                                    1096
```

<210> SEQ ID NO 2
<211> LENGTH: 4087
<212> TYPE: DNA
<213> ORGANISM: Perilla frutescens
<220> FEATURE:
<221> NAME/KEY: CDS
<222> LOCATION: (1097)..(2443)
<223> OTHER INFORMATION: pSPB3311, anthocyanin 3-acyl transferase promoter + CDS + terminator

<400> SEQUENCE: 2

```
aactattatg atcccacaga gttttttgaca gatgagtctt caggaggaga tgctgaacct      60
tttcactact ctactgaacg catcacaagt ttatcggctt atatgactaa tagggatcaa     120
cttcacaaca gagaggctca tagagctctt aaagaggatt tgatcgagca catatggaaa     180
aaattcggca ctaactaaat atataattta cgttttatgc actcgtaatt taaaatttca     240
tgtgtctcat tgtagtttat ttaattatgt tttcactctt gtaattttta ttttgttgtg     300
aagtaaatta tgaatttata attatatggg taatttttg  ataattatgc aattaaaaat     360
aattaatatt ttttaaatgc aagagaaaaa tgttatttta ataacatgtt cttattaaaa     420
```

```
aataaaatga taaatatttt atgtaggttg ggagaaaatg aaaaaataat attttatttg      480
aaggttgggt tggatgaggt cactgatggg agtataaata atactccctc cgtcccataa      540
ttattgtcca ttattccttt tgggatgtc ccaaaattat agtcctattc taaattggga       600
ttgtatttaa atattctttt acaaatataa ccctatttga tatagtatga atgcaattaa      660
tatagtaaaa aaataagggc aatataggat aattattgta aattgtatat ttccaataca     720
tattaaatgt gatttcttaa tctgtgtgaa aataggaagt ggactataat tatgggacgg     780
agggagtata aagttggagg ttgtggatgt ggaggagaaa gaaattaata ttttatttaa     840
agattggatt aaaggaggtc actgatgtgg gtagtcttag aggaaatgta gtcttagagg     900
aaatctgccc agcaaaataa aataataagt aaataaataa actaaatatg tattgaatgc     960
gacatctagc aatatagcca catatatagt gcagtagcac gcagcgctcg ttactcgtca    1020
gtcgtcaaag aatggtaagt atagaaaagc atctttaaat aacacaccaa aaaccacagc    1080
tacgttcaac accgcc atg acc acc acc gtg atc gaa acg tgt aga gtt ggg    1132
              Met Thr Thr Thr Val Ile Glu Thr Cys Arg Val Gly
                1               5                  10 cca ccg ccg gac tcg gtg gcg gag caa tcg ttg ccc ctc aca ttc ttc      1180
Pro Pro Pro Asp Ser Val Ala Glu Gln Ser Leu Pro Leu Thr Phe Phe
            15                  20                  25 gac atg acg tgg ctg cat ttt cat ccc atg ctt cag ctc ctc ttc tac      1228
Asp Met Thr Trp Leu His Phe His Pro Met Leu Gln Leu Leu Phe Tyr
        30                  35                  40 gaa ttc cct tgt tcc aag caa cat ttc tca gaa tcc atc att cca aaa      1276
Glu Phe Pro Cys Ser Lys Gln His Phe Ser Glu Ser Ile Ile Pro Lys
45                  50                  55                  60 ctc aaa caa tct ctc tct aaa act ctc ata cac ttc ttc cct ctc tca      1324
Leu Lys Gln Ser Leu Ser Lys Thr Leu Ile His Phe Phe Pro Leu Ser
                65                  70                  75 tgc aat tta atc tac cct tca tct ccg gag aaa atg ccc gag ttt cgg      1372
Cys Asn Leu Ile Tyr Pro Ser Ser Pro Glu Lys Met Pro Glu Phe Arg
            80                  85                  90 tat cta tcg ggg gac tcg gtt tct ttc act atc gca gaa tct agc gac      1420
Tyr Leu Ser Gly Asp Ser Val Ser Phe Thr Ile Ala Glu Ser Ser Asp
        95                  100                 105 gac ttc gat gat ctc gtc gga aat cgc gca gaa tct ccc gtt agg ctc      1468
Asp Phe Asp Asp Leu Val Gly Asn Arg Ala Glu Ser Pro Val Arg Leu
    110                 115                 120 tac aac ttc gtc cct aaa ttg ccg cag att gtc gaa gaa tct gat aga      1516
Tyr Asn Phe Val Pro Lys Leu Pro Gln Ile Val Glu Glu Ser Asp Arg
125                 130                 135                 140 aaa ctc ttc caa gtt ttc gcc gtg cag gtg act ctt ttc cca ggt cga      1564
Lys Leu Phe Gln Val Phe Ala Val Gln Val Thr Leu Phe Pro Gly Arg
                145                 150                 155 ggc gtc ggt att gga ata gca acg cat cac acc gtt agc gat gcc ccg      1612
Gly Val Gly Ile Gly Ile Ala Thr His His Thr Val Ser Asp Ala Pro
            160                 165                 170 tcg ttt ctc gcc ttt ata acg gct tgg gct tgg atg agc aaa cac att      1660
Ser Phe Leu Ala Phe Ile Thr Ala Trp Ala Trp Met Ser Lys His Ile
        175                 180                 185 gaa gat gaa gat gaa gag ttt aaa tct ttg cca gtt ttc gat aga tcc      1708
Glu Asp Glu Asp Glu Glu Phe Lys Ser Leu Pro Val Phe Asp Arg Ser
    190                 195                 200 gtc ata aaa tat ccg acg aaa ttt gac tcg att tat tgg aaa aag gcg      1756
Val Ile Lys Tyr Pro Thr Lys Phe Asp Ser Ile Tyr Trp Lys Lys Ala
205                 210                 215                 220 cta aaa ttt cct ttg caa tct cgt cat ccc tca tta ccg acg gac cgc      1804
```

-continued

| | | |
|---|---|---|
| Leu Lys Phe Pro Leu Gln Ser Arg His Pro Ser Leu Pro Thr Asp Arg<br>225 230 235 | | |
| att cga acc acg ttc gtt ttc acc caa tcc gaa att aag aaa ttg aag<br>Ile Arg Thr Thr Phe Val Phe Thr Gln Ser Glu Ile Lys Lys Leu Lys<br>240 245 250 | 1852 | |
| ggt tcg att cag tcc aga gtt cca agt tta gtc cat ctc tca tct ttt<br>Gly Ser Ile Gln Ser Arg Val Pro Ser Leu Val His Leu Ser Ser Phe<br>255 260 265 | 1900 | |
| gta gcg att gca gct tat atg tgg gct ggc gta acg aaa tca ctc aca<br>Val Ala Ile Ala Ala Tyr Met Trp Ala Gly Val Thr Lys Ser Leu Thr<br>270 275 280 | 1948 | |
| gca gat gaa gac cac gac gac ggg gat gca ttt ttc ttg att ccg gtc<br>Ala Asp Glu Asp His Asp Asp Gly Asp Ala Phe Phe Leu Ile Pro Val<br>285 290 295 300 | 1996 | |
| gat cta agg cca cga tta gat ccg cca gtt ccc gaa aat tac ttc ggg<br>Asp Leu Arg Pro Arg Leu Asp Pro Pro Val Pro Glu Asn Tyr Phe Gly<br>305 310 315 | 2044 | |
| aac tgc tta tcg tac gcg ctg ccg aga atg cgg cgg cga gag ctg gtg<br>Asn Cys Leu Ser Tyr Ala Leu Pro Arg Met Arg Arg Arg Glu Leu Val<br>320 325 330 | 2092 | |
| gga gag aaa ggg gtg ttt ctg gcg gct gag gca atc gcg gcg gag atc<br>Gly Glu Lys Gly Val Phe Leu Ala Ala Glu Ala Ile Ala Ala Glu Ile<br>335 340 345 | 2140 | |
| aaa aaa agg atc aac gac aag aga ata tta gaa acg gtg gag aaa tgg<br>Lys Lys Arg Ile Asn Asp Lys Arg Ile Leu Glu Thr Val Glu Lys Trp<br>350 355 360 | 2188 | |
| tcg ctg gag att cgt gaa gcg ttg cag aaa tca tat ttt tcg gtg gca<br>Ser Leu Glu Ile Arg Glu Ala Leu Gln Lys Ser Tyr Phe Ser Val Ala<br>365 370 375 380 | 2236 | |
| gga tcg agc aag cta gat ctt tac ggt gca gat ttt gga tgg ggg aag<br>Gly Ser Ser Lys Leu Asp Leu Tyr Gly Ala Asp Phe Gly Trp Gly Lys<br>385 390 395 | 2284 | |
| gcg aga aag caa gaa ata ttg tcg att gat ggg gag aaa tat gca atg<br>Ala Arg Lys Gln Glu Ile Leu Ser Ile Asp Gly Glu Lys Tyr Ala Met<br>400 405 410 | 2332 | |
| acg ctt tgt aaa gcc agg gat ttc gaa gga gga ttg gag gtt tgc ttg<br>Thr Leu Cys Lys Ala Arg Asp Phe Glu Gly Gly Leu Glu Val Cys Leu<br>415 420 425 | 2380 | |
| tct ttg cct aag gac aaa atg gat gct ttt gct gct tat ttt tca gcg<br>Ser Leu Pro Lys Asp Lys Met Asp Ala Phe Ala Ala Tyr Phe Ser Ala<br>430 435 440 | 2428 | |
| gga att aat ggt taa taaatgtatg taattaaact aatattatta tgtaacaatt<br>Gly Ile Asn Gly<br>445 | 2483 | |
| aattaagtgt tgagtaacgt gaagaataat atcttttacc tattatatat ttatgagttg | 2543 | |
| gttcaaataa aatcacttca tttattgtat taaccgttta gtgttcttct caccatattt | 2603 | |
| tggtgctatt ttttaaaaaa tgttttttttt attgtatttt agtattaatt gttttaccac | 2663 | |
| taaaattaca gtaaaatgca agatagttta atttttacat ttacatatga aacacattct | 2723 | |
| ctttataacc aacctctcta tatatataat atgtgtgtat gtatgtatac acatgtatga | 2783 | |
| atactagaaa tatatcttaa accatccatc cttcaaaaat ttcggggcca tattgcatgg | 2843 | |
| tgacattata atatttgata atttcttcga acacgttatt aattcaattt aataattcta | 2903 | |
| ataaaaagac gctcagacaa tatatgtaga taggatcggc ccaaagggggt gtctgggtgg | 2963 | |
| gctgtcgccc atgggccccg aaatcttagg ggcaaaaaaa aaaaaattca ttataccttag | 3023 | |
| ggcaaaaaaa ttaccgctct tcacttctct gcctctctcc ctcatccctc gttcctcctc | 3083 | |

```
tctcttccct atgtacgcct ctttcactcc ctccccctct ctcagttctc tatcacttgt    3143
attttgtatt gaaacttgt tgaaaactaa accaaaaata gaaaaggta tagaaaattt      3203 gaaaacaaag gttgttttt tgtgttgctg cagttcccaa acttgccgag ttgccgactt     3263
gccgtgttga attgttatat atgttaaaag cctaaaatat atcctttcag aattgagatg    3323
gattgttgta actatcaggt ttttttatt gagaattta gatcaattag ttatcttgta      3383
attttttatt cttttaata caatactccc tccatcccaa tagcaaggtc cccttgctat     3443
tgggcacggg tattaaggag gaggattatt ataatgaaaa ttaatataaa gtaagtggat    3503
tccactttat taaggaatat tataatcaaa agtaatataa agtaagtgga ttccacttta    3563
attaggacac taattatttt ctttttggt atgagacttt gctattggga catcccaaaa     3623
aggcaaaaga gaccttgcta ttaggacggt ggacgtgctg ccgaggcacg caaattaatt    3683 taccttcct cttctatact aactcgtagt agcggcgagt aaaggtcgaa ccctcaagga     3743
gcaattgaac tagatgtgct attagaaata aaataaacac aagtgagagg ggagttttg     3803 gtttcaattt aactaaaact aattatgaaa atgaaaaaac aaatataaaa cataaacagg    3863
tagacgaaat atgataaaga tagaattcta gttctcggtt cagttatcac ctttctccaa    3923
gtatttcatg aataatgcaa cgcctctttt catacaactg agaatcgatg tccaaaggtt    3983
aatatcaagc tttatttacc taattgtctc gtacgattag ttaactaaaa caagctcttt    4043
aattaactct actcaattag ataacctaga ataagctctc taga                    4087
```

<210> SEQ ID NO 3
<211> LENGTH: 448
<212> TYPE: PRT
<213> ORGANISM: Perilla frutescens

<400> SEQUENCE: 3

```
Met Thr Thr Thr Val Ile Glu Thr Cys Arg Val Gly Pro Pro Asp
1               5                   10                  15

Ser Val Ala Glu Gln Ser Leu Pro Leu Thr Phe Phe Asp Met Thr Trp
            20                  25                  30

Leu His Phe His Pro Met Leu Gln Leu Leu Phe Tyr Glu Phe Pro Cys
        35                  40                  45

Ser Lys Gln His Phe Ser Glu Ser Ile Ile Pro Lys Leu Lys Gln Ser
    50                  55                  60

Leu Ser Lys Thr Leu Ile His Phe Phe Pro Leu Ser Cys Asn Leu Ile
65                  70                  75                  80

Tyr Pro Ser Ser Pro Glu Lys Met Pro Glu Phe Arg Tyr Leu Ser Gly
                85                  90                  95

Asp Ser Val Ser Phe Thr Ile Ala Glu Ser Ser Asp Asp Phe Asp Asp
            100                 105                 110

Leu Val Gly Asn Arg Ala Glu Ser Pro Val Arg Leu Tyr Asn Phe Val
        115                 120                 125

Pro Lys Leu Pro Gln Ile Val Glu Glu Ser Asp Arg Lys Leu Phe Gln
    130                 135                 140

Val Phe Ala Val Gln Val Thr Leu Phe Pro Gly Arg Gly Val Gly Ile
145                 150                 155                 160

Gly Ile Ala Thr His His Thr Val Ser Asp Ala Pro Ser Phe Leu Ala
                165                 170                 175

Phe Ile Thr Ala Trp Ala Trp Met Ser Lys His Ile Glu Asp Glu Asp
            180                 185                 190

Glu Glu Phe Lys Ser Leu Pro Val Phe Asp Arg Ser Val Ile Lys Tyr
```

```
                195                 200                 205
Pro Thr Lys Phe Asp Ser Ile Tyr Trp Lys Lys Ala Leu Lys Phe Pro
        210                 215                 220

Leu Gln Ser Arg His Pro Ser Leu Pro Thr Asp Arg Ile Arg Thr Thr
225                 230                 235                 240

Phe Val Phe Thr Gln Ser Glu Ile Lys Lys Leu Lys Gly Ser Ile Gln
                245                 250                 255

Ser Arg Val Pro Ser Leu Val His Leu Ser Ser Phe Val Ala Ile Ala
            260                 265                 270

Ala Tyr Met Trp Ala Gly Val Thr Lys Ser Leu Thr Ala Asp Glu Asp
        275                 280                 285

His Asp Asp Gly Asp Ala Phe Phe Leu Ile Pro Val Asp Leu Arg Pro
290                 295                 300

Arg Leu Asp Pro Pro Val Pro Glu Asn Tyr Phe Gly Asn Cys Leu Ser
305                 310                 315                 320

Tyr Ala Leu Pro Arg Met Arg Arg Glu Leu Val Gly Glu Lys Gly
                325                 330                 335

Val Phe Leu Ala Ala Glu Ala Ile Ala Ala Glu Ile Lys Lys Arg Ile
            340                 345                 350

Asn Asp Lys Arg Ile Leu Glu Thr Val Glu Lys Trp Ser Leu Glu Ile
        355                 360                 365

Arg Glu Ala Leu Gln Lys Ser Tyr Phe Ser Val Ala Gly Ser Ser Lys
370                 375                 380

Leu Asp Leu Tyr Gly Ala Asp Phe Gly Trp Gly Lys Ala Arg Lys Gln
385                 390                 395                 400

Glu Ile Leu Ser Ile Asp Gly Glu Lys Tyr Ala Met Thr Leu Cys Lys
                405                 410                 415

Ala Arg Asp Phe Glu Gly Gly Leu Glu Val Cys Leu Ser Leu Pro Lys
            420                 425                 430

Asp Lys Met Asp Ala Phe Ala Ala Tyr Phe Ser Ala Gly Ile Asn Gly
        435                 440                 445

<210> SEQ ID NO 4
<211> LENGTH: 6835
<212> TYPE: DNA
<213> ORGANISM: Perilla frutescens
<220> FEATURE:
<221> NAME/KEY: CDS
<222> LOCATION: (1608)..(2330)
<223> OTHER INFORMATION: Other ORF
<220> FEATURE:
<221> NAME/KEY: CDS
<222> LOCATION: (3439)..(4785)
<223> OTHER INFORMATION: SAT208 ORF
<220> FEATURE:
<221> NAME/KEY: misc_feature
<222> LOCATION: (6815)..(6815)
<223> OTHER INFORMATION: n is a, c, g, or t

<400> SEQUENCE: 4
ccccaaaaac cttgattagg gtgatggttc acgtagtggg ccatcgccct gatagacggt      60
ttttcgccct tgacgttgg agtccacgtt ctttaatagt ggactcttgt tccaaactgg     120
aacaacactc aaccctatct cggtctattc ttttgattta aagggatttt tgccgatttc     180
ggcctattgg ttaaaaaaat gagctgattt acaaaaatt taacgcgaat tttaacaaaa     240
tattaacgct tacaatttcc attcgccatt caggctgcgc aactgttggg aagggcgatc     300
ggtgcgggcc tcttcgctat tacgccagct ggcgaaaggg gatgtgctg caaggcgatt     360
```

-continued

```
aagttgggta acgccagggt tttcccagtc acgacgttgt aaaacgacgg ccagtgagcg      420
cgcgtaatac gactcactat agggcgaatt gggtaccggg ccccccctcg aggtcgacgg      480
tatcgataag cttgatatcg aattcctgca gcccggggga tccactagtt ctagaagatg      540
aagagacaaa acatcgacta cttgcccttg tgtttgggca aaattaaatt aatgtaattg      600
taattgtgag atgtgtgtta gtaattatgc tatgtgtgtg ttagtaatta tgagatgtgt      660
gtgtttgtaa ttttgagatg tcttttcctc actttataaa taattaatgt attttatgca      720
tatctatttc tcttattctt ttcatacaaa cctgcatgca taagtctcaa tcatgcattg      780
gattctttat gccttgtcaa tttctttttg tacaaacctc atgcatctca atcatgcatt      840
ggattcttat actctcattt caatttatat gcaagagtaa agctaagtat atcacatgca      900
ttggattcca ctttatatca aattgatttc ttgataaatc acatgctttt gtcagccatc      960
acatgcattg gattccactt tatatcaaat taatttcttg ataaatcaca tactttgtc     1020 ggccatttca tgcattggat tccactttat atcaaattga ttttttgata atcacatgc     1080 ttttgtcggc tagcccatgc tttgtctata catatctcag aaaatgcaca tcaaaagaaa     1140
ctcaaacaaa atcctcaata ccttaccaca tctttcaact tcactttaga aaaatgtctg     1200
cacatgaaaa ttctgatgtt gaatcaaact caagttctaa ttattctgat tctaacgaac     1260
ttgatgaatg gctagagcga ggttatgaaa atatcgtga agttgatagt ataatccaga     1320
atgtgctcat aaataatccc aatctggttg taggagctca aacttctaca gtcagaagaa     1380
ggtattgtga tagggaacgt gagaatggtg aagagcgttt gatgaaagac tatttttgtct     1440 ctaatccaac gtattctcca gagctcttcc gacgatgatt tcacatgcag aaatcacttt     1500
ttcttcgtat agtggaggcc gttactacca atgatgacta ttttcaacag aggccaaatt     1560
gcacgggtag aaaaggtctt tcaccattgt aaaaatgtac aggagct atg agg gta       1616
                                                        Met Arg Val
                                                        1 ttg gct tat ggg gca tca gcc gat gtc gtt gat gaa tac tta cga atg       1664
Leu Ala Tyr Gly Ala Ser Ala Asp Val Val Asp Glu Tyr Leu Arg Met
    5                  10                  15 agt gca acg gta aca aga gat gct gtc atc cat ttc gta gaa ggt gtc       1712
Ser Ala Thr Val Thr Arg Asp Ala Val Ile His Phe Val Glu Gly Val
20                  25                  30                  35 att tca tgc ttc agt gac aca tat ctt agg aag cct aat caa caa gat       1760
Ile Ser Cys Phe Ser Asp Thr Tyr Leu Arg Lys Pro Asn Gln Gln Asp
                40                  45                  50 ttg gca aga cta ctc tat gtt gga gag caa cgt ggt ttt cct ggc atg       1808
Leu Ala Arg Leu Leu Tyr Val Gly Glu Gln Arg Gly Phe Pro Gly Met
            55                  60                  65 att ggt agt att gat tgc atg cac tgg gaa tgg aca aat tgt cct aat       1856
Ile Gly Ser Ile Asp Cys Met His Trp Glu Trp Thr Asn Cys Pro Asn
        70                  75                  80 gcc tgg gca ggg caa ttt aca ggg aga agt gga aag tca aca atc att       1904
Ala Trp Ala Gly Gln Phe Thr Gly Arg Ser Gly Lys Ser Thr Ile Ile
    85                  90                  95 ttg gaa gct gtt gca tca tat gat tta tgg ata tgg cat gcg ttt ttt       1952
Leu Glu Ala Val Ala Ser Tyr Asp Leu Trp Ile Trp His Ala Phe Phe
100                 105                 110                 115 gga aca tca ggt gcg tgc aat gat att aat gtt ctc cac ggt tct cca       2000
Gly Thr Ser Gly Ala Cys Asn Asp Ile Asn Val Leu His Gly Ser Pro
                120                 125                 130 att ttt agt gat gtt tta gaa ggt cga gca cca cat gtt agt tac atc       2048
Ile Phe Ser Asp Val Leu Glu Gly Arg Ala Pro His Val Ser Tyr Ile
            135                 140                 145
```

```
gtc aat ggt cgc caa aat gat aga gca tat tat ctc acc gat ggc ata      2096
Val Asn Gly Arg Gln Asn Asp Arg Ala Tyr Tyr Leu Thr Asp Gly Ile
            150                 155                 160 tat cct tca tgg gct gca ttt gta aag tca atc aca tct cct atg act      2144
Tyr Pro Ser Trp Ala Ala Phe Val Lys Ser Ile Thr Ser Pro Met Thr
165                 170                 175 cga aag tat aag ttg ttt gtt caa cac caa gaa gct gct aga aaa gat      2192
Arg Lys Tyr Lys Leu Phe Val Gln His Gln Glu Ala Ala Arg Lys Asp
180                 185                 190                 195 gta gaa cgg gcc ttt gga gtt cta caa gct cgt ttt gca ttt att cga      2240
Val Glu Arg Ala Phe Gly Val Leu Gln Ala Arg Phe Ala Phe Ile Arg
                200                 205                 210 cgt cca tgt ctt gtt tgg gac aag gtt ttg atg gga aaa att atg atg      2288
Arg Pro Cys Leu Val Trp Asp Lys Val Leu Met Gly Lys Ile Met Met
            215                 220                 225 gct tgt atc atc ata cac aat atg att gtg gag gat gaa tga              2330
Ala Cys Ile Ile Ile His Asn Met Ile Val Glu Asp Glu
        230                 235                 240 gacacatacc taaactatta tgatcccaca gagttttga cagatgagtc ttcaggagga     2390
gatgctgaac cttttcacta ctctactgaa cgcatcacaa gtttatcggc ttatatgact   2450
aatagggatc aacttcacaa cagagaggct catagagctc ttaaagagga tttgatcgag   2510
cacatatgga aaaaattcgg cactaactaa atatataatt tacgttttat gcactcgtaa   2570
tttaaaattt catgtgtctc attgtagttt atttaattat gttttcactc ttgtaatttt   2630
tattttgttg tgaagtaaat tatgaattta taattatatg ggtaattttt tgataattat   2690
gcaattaaaa ataattaata tttttaaat gcaagagaaa aatgttattt taataacatg    2750
ttcttattaa aaaataaaat gataaatatt ttatgtaggt tgggagaaaa tgaaaaaata  2810
atattttatt tgaaggttgg gttggatgag gtcactgatg ggagtataaa taatactccc   2870
tccgtcccat aattattgtc cattattcct ttttgggatg tcccaaaatt atagtcctat   2930
tctaaattgg gattgtattt aaatattctt ttacaaatat aaccctattt gatatagtat   2990
gaatgcaatt aatatagtaa aaaataagg gcaatatagg ataattattg taaattgtat   3050
atttccaata catattaaat gtgatttctt aatctgtgtg aaaataggaa gtggactata   3110
attatgggac ggaggagta taaagttgga ggttgtggat gtggaggaga agaaattaa    3170 tattttatt aaagattgga ttaaaggagg tcactgatgt gggtagtctt agaggaaatg   3230
tagtcttaga ggaaatctgc ccagcaaaat aaaataataa gtaaataaat aaactaaata   3290
tgtattgaat gcgacatcta gcaatatagc cacatatata gtgcagtagc acgcagcgct   3350
cgttactcgt cagtcgtcaa agaatggtaa gtatagaaaa gcatctttaa ataacacacc   3410
aaaaaccaca gctacgttca acaccgcc atg acc acc acc gtg atc gaa acg      3462
                                Met Thr Thr Thr Val Ile Glu Thr
                                                     245 tgt aga gtt ggg cca ccg ccg gac tcg gtg gcg gag caa tcg ttg ccg     3510
Cys Arg Val Gly Pro Pro Pro Asp Ser Val Ala Glu Gln Ser Leu Pro
        250                 255                 260 ctc aca ttc ttc gac atg acg tgg ctg cat ttt cat ccc atg ctt cag     3558
Leu Thr Phe Phe Asp Met Thr Trp Leu His Phe His Pro Met Leu Gln
265                 270                 275                 280 ctc ctc ttc tac gaa ttc cct tgt tcc aag caa cat ttc tca gaa tcc     3606
Leu Leu Phe Tyr Glu Phe Pro Cys Ser Lys Gln His Phe Ser Glu Ser
                285                 290                 295 atc att cca aaa ctc aaa caa tct ctc tct aaa act ctc ata cac ttc     3654
Ile Ile Pro Lys Leu Lys Gln Ser Leu Ser Lys Thr Leu Ile His Phe
```

|        |        |        |        |        |        |        |        |        |        |        |        |        |        |        |        |      |
|--------|--------|--------|--------|--------|--------|--------|--------|--------|--------|--------|--------|--------|--------|--------|--------|------|
| ttc    | cct    | ctc    | tca    | tgc    | aat    | tta    | atc    | tac    | cct    | tca    | tct    | ccg    | gag    | aaa    | atg    | 3702 |
| Phe    | Pro    | Leu    | Ser    | Cys    | Asn    | Leu    | Ile    | Tyr    | Pro    | Ser    | Ser    | Pro    | Glu    | Lys    | Met    |      |
|        |        | 315    |        |        |        | 320    |        |        |        | 325    |        |        |        |        |        |      |
| ccc    | gag    | ttt    | cgg    | tat    | cta    | tcg    | ggg    | gac    | tcg    | gtt    | tct    | ttc    | act    | atc    | gca    | 3750 |
| Pro    | Glu    | Phe    | Arg    | Tyr    | Leu    | Ser    | Gly    | Asp    | Ser    | Val    | Ser    | Phe    | Thr    | Ile    | Ala    |      |
|        | 330    |        |        |        |        | 335    |        |        |        |        | 340    |        |        |        |        |      |
| gaa    | tct    | agc    | gac    | gac    | ttc    | gat    | gat    | ctc    | gtc    | gga    | aat    | cgc    | gca    | gaa    | tct    | 3798 |
| Glu    | Ser    | Ser    | Asp    | Asp    | Phe    | Asp    | Asp    | Leu    | Val    | Gly    | Asn    | Arg    | Ala    | Glu    | Ser    |      |
| 345    |        |        |        | 350    |        |        |        |        | 355    |        |        |        |        | 360    |        |      |
| ccc    | gtt    | agg    | ctc    | tac    | aac    | ttc    | gtc    | cct    | aaa    | ttg    | ccg    | cag    | att    | gtc    | gaa    | 3846 |
| Pro    | Val    | Arg    | Leu    | Tyr    | Asn    | Phe    | Val    | Pro    | Lys    | Leu    | Pro    | Gln    | Ile    | Val    | Glu    |      |
|        |        |        |        | 365    |        |        |        |        | 370    |        |        |        |        | 375    |        |      |
| gaa    | tct    | gat    | aga    | aaa    | ctc    | ttc    | caa    | gtt    | ttc    | gcc    | gtg    | cag    | gtg    | act    | ctt    | 3894 |
| Glu    | Ser    | Asp    | Arg    | Lys    | Leu    | Phe    | Gln    | Val    | Phe    | Ala    | Val    | Gln    | Val    | Thr    | Leu    |      |
|        |        |        | 380    |        |        |        |        | 385    |        |        |        |        | 390    |        |        |      |
| ttc    | cca    | ggt    | cga    | ggc    | gtc    | ggt    | att    | gga    | ata    | gca    | acg    | cat    | cac    | acc    | gtt    | 3942 |
| Phe    | Pro    | Gly    | Arg    | Gly    | Val    | Gly    | Ile    | Gly    | Ile    | Ala    | Thr    | His    | His    | Thr    | Val    |      |
|        |        | 395    |        |        |        |        | 400    |        |        |        |        | 405    |        |        |        |      |
| agc    | gat    | gcc    | ccg    | tcg    | ttt    | ctc    | gcc    | ttt    | ata    | acg    | gct    | tgg    | gct    | tgg    | atg    | 3990 |
| Ser    | Asp    | Ala    | Pro    | Ser    | Phe    | Leu    | Ala    | Phe    | Ile    | Thr    | Ala    | Trp    | Ala    | Trp    | Met    |      |
|        | 410    |        |        |        |        | 415    |        |        |        |        | 420    |        |        |        |        |      |
| agc    | aaa    | cac    | att    | gaa    | gat    | gaa    | gat    | gaa    | gag    | ttt    | aaa    | tct    | ttg    | cca    | gtt    | 4038 |
| Ser    | Lys    | His    | Ile    | Glu    | Asp    | Glu    | Asp    | Glu    | Glu    | Phe    | Lys    | Ser    | Leu    | Pro    | Val    |      |
| 425    |        |        |        | 430    |        |        |        |        | 435    |        |        |        |        | 440    |        |      |
| ttc    | gat    | aga    | tcc    | gtc    | ata    | aaa    | tat    | ccg    | acg    | aaa    | ttt    | gac    | tcg    | att    | tat    | 4086 |
| Phe    | Asp    | Arg    | Ser    | Val    | Ile    | Lys    | Tyr    | Pro    | Thr    | Lys    | Phe    | Asp    | Ser    | Ile    | Tyr    |      |
|        |        |        |        | 445    |        |        |        |        | 450    |        |        |        |        | 455    |        |      |
| tgg    | aaa    | aag    | gcg    | cta    | aaa    | ttt    | cct    | ttg    | caa    | tct    | cgt    | cat    | ccc    | tca    | tta    | 4134 |
| Trp    | Lys    | Lys    | Ala    | Leu    | Lys    | Phe    | Pro    | Leu    | Gln    | Ser    | Arg    | His    | Pro    | Ser    | Leu    |      |
|        |        |        | 460    |        |        |        |        | 465    |        |        |        |        | 470    |        |        |      |
| ccg    | acg    | gac    | cgc    | att    | cga    | acc    | acg    | ttc    | gtt    | ttc    | acc    | caa    | tcc    | gaa    | att    | 4182 |
| Pro    | Thr    | Asp    | Arg    | Ile    | Arg    | Thr    | Thr    | Phe    | Val    | Phe    | Thr    | Gln    | Ser    | Glu    | Ile    |      |
|        |        |        | 475    |        |        |        |        | 480    |        |        |        |        | 485    |        |        |      |
| aag    | aaa    | ttg    | aag    | ggt    | tcg    | att    | cag    | tcc    | aga    | gtt    | cca    | agt    | tta    | gtc    | cat    | 4230 |
| Lys    | Lys    | Leu    | Lys    | Gly    | Ser    | Ile    | Gln    | Ser    | Arg    | Val    | Pro    | Ser    | Leu    | Val    | His    |      |
|        | 490    |        |        |        |        | 495    |        |        |        |        | 500    |        |        |        |        |      |
| ctc    | tca    | tct    | ttt    | gta    | gcg    | att    | gca    | gct    | tat    | atg    | tgg    | gct    | ggc    | gta    | acg    | 4278 |
| Leu    | Ser    | Ser    | Phe    | Val    | Ala    | Ile    | Ala    | Ala    | Tyr    | Met    | Trp    | Ala    | Gly    | Val    | Thr    |      |
| 505    |        |        |        | 510    |        |        |        |        | 515    |        |        |        |        | 520    |        |      |
| aaa    | tca    | ctc    | aca    | gca    | gat    | gaa    | gac    | cac    | gac    | gac    | ggg    | gat    | gca    | ttt    | ttc    | 4326 |
| Lys    | Ser    | Leu    | Thr    | Ala    | Asp    | Glu    | Asp    | His    | Asp    | Asp    | Gly    | Asp    | Ala    | Phe    | Phe    |      |
|        |        |        |        | 525    |        |        |        |        | 530    |        |        |        |        | 535    |        |      |
| ttg    | att    | ccg    | gtc    | gat    | cta    | agg    | cca    | cga    | tta    | gat    | ccg    | cca    | gtt    | ccc    | gaa    | 4374 |
| Leu    | Ile    | Pro    | Val    | Asp    | Leu    | Arg    | Pro    | Arg    | Leu    | Asp    | Pro    | Pro    | Val    | Pro    | Glu    |      |
|        |        |        | 540    |        |        |        |        | 545    |        |        |        |        | 550    |        |        |      |
| aat    | tac    | ttc    | ggg    | aac    | tgc    | tta    | tcg    | tac    | gcg    | ctg    | ccg    | aga    | atg    | cgg    | cgg    | 4422 |
| Asn    | Tyr    | Phe    | Gly    | Asn    | Cys    | Leu    | Ser    | Tyr    | Ala    | Leu    | Pro    | Arg    | Met    | Arg    | Arg    |      |
|        |        | 555    |        |        |        |        | 560    |        |        |        |        | 565    |        |        |        |      |
| cga    | gag    | ctg    | gtg    | gga    | gag    | aaa    | ggg    | gtg    | ttt    | ctg    | gcg    | gct    | gag    | gca    | atc    | 4470 |
| Arg    | Glu    | Leu    | Val    | Gly    | Glu    | Lys    | Gly    | Val    | Phe    | Leu    | Ala    | Ala    | Glu    | Ala    | Ile    |      |
|        | 570    |        |        |        |        | 575    |        |        |        |        | 580    |        |        |        |        |      |
| gcg    | gcg    | gag    | atc    | aaa    | aaa    | agg    | atc    | aac    | gac    | aag    | aga    | ata    | tta    | gaa    | acg    | 4518 |
| Ala    | Ala    | Glu    | Ile    | Lys    | Lys    | Arg    | Ile    | Asn    | Asp    | Lys    | Arg    | Ile    | Leu    | Glu    | Thr    |      |
| 585    |        |        |        | 590    |        |        |        |        | 595    |        |        |        |        | 600    |        |      |
| gtg    | gag    | aaa    | tgg    | tcg    | ctg    | gag    | att    | cgt    | gaa    | gcg    | ttg    | cag    | aaa    | tca    | tat    | 4566 |
| Val    | Glu    | Lys    | Trp    | Ser    | Leu    | Glu    | Ile    | Arg    | Glu    | Ala    | Leu    | Gln    | Lys    | Ser    | Tyr    |      |
|        |        |        |        | 605    |        |        |        |        | 610    |        |        |        |        | 615    |        |      |
| ttt    | tcg    | gtg    | gca    | gga    | tcg    | agc    | aag    | cta    | gat    | ctt    | tac    | ggt    | gca    | gat    | ttt    | 4614 |

```
Phe Ser Val Ala Gly Ser Ser Lys Leu Asp Leu Tyr Gly Ala Asp Phe
                620             625             630 gga tgg ggg aag gcg aga aag caa gaa ata ttg tcg att gat ggg gag      4662
Gly Trp Gly Lys Ala Arg Lys Gln Glu Ile Leu Ser Ile Asp Gly Glu
            635             640             645 aaa tat gca atg acg ctt tgt aaa gcc agg gat ttc gaa gga gga ttg      4710
Lys Tyr Ala Met Thr Leu Cys Lys Ala Arg Asp Phe Glu Gly Gly Leu
650             655             660 gag gtt tgc ttg tct ttg cct aag gac aaa atg gat gct ttt gct gct      4758
Glu Val Cys Leu Ser Leu Pro Lys Asp Lys Met Asp Ala Phe Ala Ala
665             670             675             680 tat ttt tca gcg gga att aat ggt taa taaatgtatg taattaaact            4805
Tyr Phe Ser Ala Gly Ile Asn Gly
                685 aatattatta tgtaacaatt aattaagtgt tgagtaacgt gaagaataat atctttacc     4865 tattatatat ttatgagttg gttcaaataa aatcacttca tttattgtat taaccgttta    4925 gtgttcttct caccatattt tggtgctatt ttttaaaaaa tgtttttttt attgtatttt    4985 agtattaatt gttttaccac taaaattaca gtaaaatgca agatagttta atttttacat    5045 ttacatatga aacacattct ctttataacc aacctctcta tatatataat atgtgtgtat    5105 gtatgtatac acatgtatga atactagaaa tatatcttaa accatccatc cttcaaaaat   5165 ttcgggccca tattgcatgg tgacattata atatttgata atttcttcga acacgttatt   5225 aattcaattt aataattcta ataaaaagac gctcagacaa tatatgtaga taggatcggc   5285 ccaaaggggt gtctgggtgg gctgtcgccc atgggccccg aaatcttagg ggcaaaaaaa   5345 aaaaaattca ttataccntag ggcaaaaaaa ttaccgctct tcacttctct gcctctctcc  5405 ctcatccctc gttcctcctc tctcttccct atgtacgcct ctttcactcc ctcccctct    5465 ctcagttctc tatcacttgt attttgtatt gaaaacttgt tgaaaactaa accaaaaata   5525 gaaaaaggta tagaaaattt gaaaacaaag gttgtttttt tgtgttgctg cagttcccaa   5585 acttgccgag ttgccgactt gccgtgttga attgttatat atgttaaaag cctaaaatat   5645 atcctttcag aattgagatg gattgttgta actatcaggt ttttttattt gagaattta    5705 gatcaattag ttatcttgta atttttttatt cttttttaata caatactccc tccatcccaa 5765 tagcaaggtc cccttgctat tgggcacggg tattaaggag gaggattatt ataatgaaaa   5825 ttaatataaa gtaagtggat tccactttat taaggaatat tataatcaaa agtaatataa   5885 agtaagtgga ttccacttta attaggacac taattatttt ctttttttggt atgagacttt  5945 gctattggga catcccaaaa aggcaaaaga gaccttgcta ttaggacggt ggacgtgctg   6005 ccgaggcacg caaattaatt tacctttcct cttctatact aactcgtagt agcggcgagt   6065 aaaggtcgaa ccctcaagga gcaattgaac tagatgtgct attagaaata aaataaacac   6125 aagtgagagg ggagtttttg gtttcaattt aactaaaact aattatgaaa atgaaaaaac   6185 aaatataaaa cataaacagg tagacgaaat atgataaaga tagaattcta gttctcggtt   6245 cagttatcac ctttctccaa gtatttcatg aataatgcaa cgcctctttt catacaactt   6305 agaatcgatg tccaaaggtt aatatcaagc tttatttacc taattgtctc gtacgattag   6365 ttaactaaaa caagctctt aattaactct actcaattag ataacctaga ataagctctc    6425 tagagcggcc gccaccgcgg tggagctcca gcttttgttc cctttagtga gggttaattg   6485 cgcgcttggc gtaatcatgg tcatagctgt ttcctgtgtg aaattgttat ccgctcacaa   6545 ttccacacaa catacgagcc ggaagcataa agtgtaaagc ctggggtgcc taatgagtga   6605
```

-continued

```
gctaactcac attaattgcg ttgcgctcac tgcccgcttt ccagtcggga aacctgtcgt    6665
gccagctgca ttaatgaatc ggccaacgcg cggggagagg cgggttgcgt attgggccgc    6725
tcttccgctt ccttggttac ttgactcgct gcgctcggcc gtcggctgcg gcgagcggta    6785
tcaagctcac tcaaaggcgg taataccggn tatccacaga atcagggat                6835
```

<210> SEQ ID NO 5
<211> LENGTH: 240
<212> TYPE: PRT
<213> ORGANISM: Perilla frutescens

<400> SEQUENCE: 5

```
Met Arg Val Leu Ala Tyr Gly Ala Ser Ala Asp Val Val Asp Glu Tyr
1               5                   10                  15

Leu Arg Met Ser Ala Thr Val Thr Arg Asp Ala Val Ile His Phe Val
                20                  25                  30

Glu Gly Val Ile Ser Cys Phe Ser Asp Thr Tyr Leu Arg Lys Pro Asn
            35                  40                  45

Gln Gln Asp Leu Ala Arg Leu Leu Tyr Val Gly Glu Gln Arg Gly Phe
        50                  55                  60

Pro Gly Met Ile Gly Ser Ile Asp Cys Met His Trp Glu Trp Thr Asn
65                  70                  75                  80

Cys Pro Asn Ala Trp Ala Gly Gln Phe Thr Gly Arg Ser Gly Lys Ser
                85                  90                  95

Thr Ile Ile Leu Glu Ala Val Ala Ser Tyr Asp Leu Trp Ile Trp His
                100                 105                 110

Ala Phe Phe Gly Thr Ser Gly Ala Cys Asn Asp Ile Asn Val Leu His
            115                 120                 125

Gly Ser Pro Ile Phe Ser Asp Val Leu Glu Gly Arg Ala Pro His Val
        130                 135                 140

Ser Tyr Ile Val Asn Gly Arg Gln Asn Asp Arg Ala Tyr Tyr Leu Thr
145                 150                 155                 160

Asp Gly Ile Tyr Pro Ser Trp Ala Ala Phe Val Lys Ser Ile Thr Ser
                165                 170                 175

Pro Met Thr Arg Lys Tyr Lys Leu Phe Val Gln His Gln Glu Ala Ala
                180                 185                 190

Arg Lys Asp Val Glu Arg Ala Phe Gly Val Leu Gln Ala Arg Phe Ala
            195                 200                 205

Phe Ile Arg Arg Pro Cys Leu Val Trp Asp Lys Val Leu Met Gly Lys
        210                 215                 220

Ile Met Met Ala Cys Ile Ile Ile His Asn Met Ile Val Glu Asp Glu
225                 230                 235                 240
```

<210> SEQ ID NO 6
<211> LENGTH: 448
<212> TYPE: PRT
<213> ORGANISM: Perilla frutescens

<400> SEQUENCE: 6

```
Met Thr Thr Thr Val Ile Glu Thr Cys Arg Val Gly Pro Pro Pro Asp
1               5                   10                  15

Ser Val Ala Glu Gln Ser Leu Pro Leu Thr Phe Asp Met Thr Trp
                20                  25                  30

Leu His Phe His Pro Met Leu Gln Leu Leu Phe Tyr Glu Phe Pro Cys
            35                  40                  45

Ser Lys Gln His Phe Ser Glu Ser Ile Ile Pro Lys Leu Lys Gln Ser
```

```
            50                  55                  60
Leu Ser Lys Thr Leu Ile His Phe Phe Pro Leu Ser Cys Asn Leu Ile
 65                  70                  75                  80

Tyr Pro Ser Ser Pro Glu Lys Met Pro Glu Phe Arg Tyr Leu Ser Gly
                 85                  90                  95

Asp Ser Val Ser Phe Thr Ile Ala Glu Ser Ser Asp Phe Asp Asp
            100                 105                 110

Leu Val Gly Asn Arg Ala Glu Ser Pro Val Arg Leu Tyr Asn Phe Val
            115                 120                 125

Pro Lys Leu Pro Gln Ile Val Glu Glu Ser Asp Arg Lys Leu Phe Gln
            130                 135                 140

Val Phe Ala Val Gln Val Thr Leu Phe Pro Gly Arg Val Gly Ile
145                 150                 155                 160

Gly Ile Ala Thr His His Thr Val Ser Asp Ala Pro Ser Phe Leu Ala
                165                 170                 175

Phe Ile Thr Ala Trp Ala Trp Met Ser Lys His Ile Glu Asp Glu Asp
                180                 185                 190

Glu Glu Phe Lys Ser Leu Pro Val Phe Asp Arg Ser Val Ile Lys Tyr
            195                 200                 205

Pro Thr Lys Phe Asp Ser Ile Tyr Trp Lys Lys Ala Leu Lys Phe Pro
            210                 215                 220

Leu Gln Ser Arg His Pro Ser Leu Pro Thr Asp Arg Ile Arg Thr Thr
225                 230                 235                 240

Phe Val Phe Thr Gln Ser Glu Ile Lys Lys Leu Lys Gly Ser Ile Gln
                245                 250                 255

Ser Arg Val Pro Ser Leu Val His Leu Ser Ser Phe Val Ala Ile Ala
                260                 265                 270

Ala Tyr Met Trp Ala Gly Val Thr Lys Ser Leu Thr Ala Asp Glu Asp
            275                 280                 285

His Asp Asp Gly Asp Ala Phe Phe Leu Ile Pro Val Asp Leu Arg Pro
            290                 295                 300

Arg Leu Asp Pro Pro Val Pro Glu Asn Tyr Phe Gly Asn Cys Leu Ser
305                 310                 315                 320

Tyr Ala Leu Pro Arg Met Arg Arg Glu Leu Val Gly Glu Lys Gly
            325                 330                 335

Val Phe Leu Ala Ala Glu Ala Ile Ala Ala Glu Ile Lys Lys Arg Ile
            340                 345                 350

Asn Asp Lys Arg Ile Leu Glu Thr Val Glu Lys Trp Ser Leu Glu Ile
            355                 360                 365

Arg Glu Ala Leu Gln Lys Ser Tyr Phe Ser Val Ala Gly Ser Ser Lys
370                 375                 380

Leu Asp Leu Tyr Gly Ala Asp Phe Gly Trp Gly Lys Ala Arg Lys Gln
385                 390                 395                 400

Glu Ile Leu Ser Ile Asp Gly Glu Lys Tyr Ala Met Thr Leu Cys Lys
            405                 410                 415

Ala Arg Asp Phe Glu Gly Gly Leu Glu Val Cys Leu Ser Leu Pro Lys
            420                 425                 430

Asp Lys Met Asp Ala Phe Ala Tyr Phe Ser Ala Gly Ile Asn Gly
            435                 440                 445

<210> SEQ ID NO 7
<211> LENGTH: 27
<212> TYPE: DNA
<213> ORGANISM: Artificial
```

```
<220> FEATURE:
<223> OTHER INFORMATION: HindIII containing primer

<400> SEQUENCE: 7
aagcttaact attatgatcc cacagag                                          27

<210> SEQ ID NO 8
<211> LENGTH: 24
<212> TYPE: DNA
<213> ORGANISM: Artificial
<220> FEATURE:
<223> OTHER INFORMATION: BamHI containing primer

<400> SEQUENCE: 8
ggatccggcg gtgttgaacg tagc                                             24

<210> SEQ ID NO 9
<211> LENGTH: 35
<212> TYPE: DNA
<213> ORGANISM: Artificial
<220> FEATURE:
<223> OTHER INFORMATION: Primer C1
<220> FEATURE:
<221> NAME/KEY: misc_feature
<223> OTHER INFORMATION: primer C1

<400> SEQUENCE: 9
gtacatattg tcgttagaac gcgtaatacg actca                                 35

<210> SEQ ID NO 10
<211> LENGTH: 24
<212> TYPE: DNA
<213> ORGANISM: Artificial
<220> FEATURE:
<223> OTHER INFORMATION: Primer BP40-i5
<220> FEATURE:
<221> NAME/KEY: misc_feature
<223> OTHER INFORMATION: Primer BP40-i5

<400> SEQUENCE: 10
aggtgcatga tcggaccata cttc                                             24

<210> SEQ ID NO 11
<211> LENGTH: 35
<212> TYPE: DNA
<213> ORGANISM: Artificial
<220> FEATURE:
<223> OTHER INFORMATION: Primer C2
<220> FEATURE:
<221> NAME/KEY: misc_feature
<223> OTHER INFORMATION: Primer C2

<400> SEQUENCE: 11
cgttagaacg cgtaatacga ctcactatag ggaga                                 35

<210> SEQ ID NO 12
<211> LENGTH: 25
<212> TYPE: DNA
<213> ORGANISM: Artificial
<220> FEATURE:
<223> OTHER INFORMATION: Primer BP40-i7
<220> FEATURE:
<221> NAME/KEY: misc_feature
<223> OTHER INFORMATION: Primer BP40-i7

<400> SEQUENCE: 12
gaccatactt cttagcgagt ttggc                                            25
```

<210> SEQ ID NO 13
<211> LENGTH: 25
<212> TYPE: DNA
<213> ORGANISM: Artificial
<220> FEATURE:
<223> OTHER INFORMATION: Primer BP40pro-F
<220> FEATURE:
<221> NAME/KEY: misc_feature
<223> OTHER INFORMATION: Primer BP40pro-F

<400> SEQUENCE: 13
actcaaacaa gcatctcgcc atagg                                   25

<210> SEQ ID NO 14
<211> LENGTH: 2369
<212> TYPE: DNA
<213> ORGANISM: Viola x wittrockiana
<220> FEATURE:
<221> NAME/KEY: misc_feature
<223> OTHER INFORMATION: Plasmid pSFL614

<400> SEQUENCE: 14

```
actcaaacaa gcatctcgcc aatggttctc taaattttct tctactctca tctcacgtgg      60
tttccgccaa tctgtctctg attacagcct tttcacatat gtcaaaggtt cagttagtgt     120
ttttgtcctt gtttatgtcg acgatataat cgttactggc aacaatctag atgccatttc     180
tgagactaaa caattcctcg caaattcatt ctctattaaa gatctcggca ctcttcgata     240
ttttcttgga atcgaagtat ctcgttctac gaaaggtatt ttcttatgtc aacgaaaata     300
cactctcgat attctctcag attctggtca ccttggatgt cgaccttctc catttcccat     360
ggagcaacat cttcatctac ttcctgatga tggtacacca ctacccgacc catccattta     420
tcgacgtctg gttggtcgac tactttactt gactgtcact cgtcctgata ttcaatatgc     480
agtgaatact cttagtcaat tcatgcaact tcctcgttcg acccatctcg atgcggcaaa     540
tcgagttctc cgatatctca aaggatcagt tggtaaagga atcctccttt cggccactag     600
tcctctttca cttgttggtt tgctgattc tgactgggct ggttgtccaa ctactcgtcg     660
ttcaactact ggctacatta ccatgcttgg ttcaagtcct atctcttgga aaactaaaaa     720
gcaacccact gtctctcgat cttctgccga agccgaatat cgatcactcg ctgctctcac     780
ttcagagata cagtggcttc attatctact ctcggatctc ggttttcccc ctcaacaacc     840
gattaccgtt cattgtgaca accaagctgc tatacacatc gctaataatc cggttttcca     900
tgaacgaaca aagcacattg agctcgattg tcactttgtt cgtgaaaaaa ttatttctgg     960
tctcgtctcc accagttatt tgcgttcctc agatcaactt gctgatattt tcacaaaacc    1020
acttggtgca gatgcattta atcaccttat ttccaagttg ggcgtgatcg acatctctct    1080
cccggctcca acttgacggg gggtgttaaa cgtatacaag attttctaat cttgtatatt    1140
tgatttctca atatcttgta tatttgattt tctattatct tgtatttgaa cttttgtatt    1200
tccttagtat caggaaagtt agttgtagat attatttat atttcaaatc tgtatctaat    1260
acttgcctat ataaaggcca actaatcaat gaaatgaaca catcaatttt ctcaatttct    1320
cattctctgt tttcatatct attctctatt ttcacatttt ctgaaaagaa agatgcttga    1380
catgatcaga gacagttctt tcttcttcat actttcgtac taaacttctc ctggtccgca    1440
actaatcttc catcatttt ttgtgatctt cacttgagga agtctctag aaaacggcac    1500
ggtcacgctg ataagtgtt taggatccct cgaagttgag ttgcatgaat tttgcgggta    1560
cgcaagtgac ttgactctta tcttggacgt cttatatgct cgaccaaatg ttggccaagt    1620
```

```
cgggatgctc gggttaagcc tctcttaggt caagtttatg agcgaacccc tttctttgag    1680
ggctctttat ttgccaactc gtctgccatt aaagttctat tagagctcta atgctgtgta    1740
tgtggctacc gatcaccttc attctcagag gaatcctctt ttcgaatttc tggtactttg    1800
aaactagctg cttcaatttc agccactcga attaaacact aaaacagaac attgagagga    1860
acgggccctc ttccaaatat agaaagaaac agataatgtc aaaagacaca tcaactaggt    1920
cgagatacct gctcacatgc atcacatcta accaactcga gtcggacgag aaatgagttc    1980
gtaactcgat gataataagg caaaggtcta aaaccacatt cggttggtgg ttgtgttcat    2040
ggaccgatca cgtgccctaa cctaaccccc gcatccatcc accaacagct agtcctcgcc    2100
gagtccccca aagttcctat ttatatcact aaagtccctt tttctcaaca tagacatgca    2160
aacacgagac aacatggcaa ttctagtcac cgacttcgtt gtcgcggcta taattttctt    2220
gatcactcgg ttcttagttc gttctctttt caagaaacca acccgaccgc tcccccgggg    2280
tcctctcggt tggcccttgg tgggcgccct ccctctccta ggcgccatgc ctcacgtcgc    2340
actagccaaa ctcgctaaga agtatggtc                                      2369
```

```
<210> SEQ ID NO 15
<211> LENGTH: 1102
<212> TYPE: DNA
<213> ORGANISM: Viola x wittrockiana
<220> FEATURE:
<221> NAME/KEY: misc_feature
<223> OTHER INFORMATION: BP40pro
<220> FEATURE:
<221> NAME/KEY: misc_feature
<222> LOCATION: (1)..(6)
<223> OTHER INFORMATION: HindIII
<220> FEATURE:
<221> NAME/KEY: misc_feature
<222> LOCATION: (1097)..(1102)
<223> OTHER INFORMATION: BamHI

<400> SEQUENCE: 15
```

```
aagcttgtga tcgacatctc tctcccggct ccaacttgac gggggtgtt aaacgtatac      60 aagattttct aatcttgtat atttgatttt ctaatatctt gtatatttga ttttctatta    120
tcttgtattt gaacttttgt atttccttag tatcaggaaa gttagttgta gatattattt    180
tatatttcaa atctgtatct aatacttgcc tatataaagg ccaactaatc aatgaaatga    240
acacatcaat tttctcaatt tctcattctc tgttttcata tctattctct attttcacat    300
tttctgaaaa gaaagatgct tgacatgatc agagacagtt cttt cttctt catactttcg    360 tactaaactt ctcctggtcc gcaactaatc ttccatcatt ttcttgtgat cttcacttga    420
ggatagtctc tagaaaacgg cacggtcacg ctggataagt gtttagctag cctcgaagtt    480
gagttgcatg aattttgcgg gtacgcaagt gacttgactc ttatcttgga cgtcttatat    540
gctcgaccaa atgttggcca agtcgggatg ctcgggttaa gcctctctta ggtcaagttt    600
atgagcgaac ccctttcttt gagggctctt tatttgccaa ctcgtctgcc attaaagttc    660
tattagagct ctaatgctgt gtatgtggct accgatcacc ttcattctca gaggaatcct    720
cttttcgaat ttctggtact ttgaaactag ctgcttcaat ttcagccact cgaattaaac    780
actaaaacag aacattgaga ggaacgggcc ctcttccaaa tatagaaaga aacagataat    840
gtcaaaagac acatcaacta ggtcgagata cctgctcaca tgcatcacat ctaaccaact    900
cgagtcggac gagaaatgag ttcgtaactc gatgataata aggcaaaggt ctaaaaccac    960
attcggttgg tggttgtgtt catggaccga tcacgtgccc taacctaacc cccgcatcca   1020
```
tccaccaaca gctagtcctc gccgagtccc ccaaagttcc tatttatatc actaaagtcc    1080 cttttttctca acatagggat cc                                            1102

<210> SEQ ID NO 16
<211> LENGTH: 25
<212> TYPE: DNA
<213> ORGANISM: Artificial
<220> FEATURE:
<223> OTHER INFORMATION: Primer BP40pro-HindIII-F
<220> FEATURE:
<221> NAME/KEY: misc_feature
<223> OTHER INFORMATION: Primer BP40pro-HindIII-F

<400> SEQUENCE: 16
aagcttgtga tcgacatctc tctcc                                          25

<210> SEQ ID NO 17
<211> LENGTH: 21
<212> TYPE: DNA
<213> ORGANISM: Artificial
<220> FEATURE:
<223> OTHER INFORMATION: Primer BP40pro-NheI-R
<220> FEATURE:
<221> NAME/KEY: misc_feature
<223> OTHER INFORMATION: Primer BP40pro-NheI-R

<400> SEQUENCE: 17
cgaggctagc taaacactta t                                              21

<210> SEQ ID NO 18
<211> LENGTH: 20
<212> TYPE: DNA
<213> ORGANISM: Artificial
<220> FEATURE:
<223> OTHER INFORMATION: Primer BP40pro-NheI-F
<220> FEATURE:
<221> NAME/KEY: misc_feature
<223> OTHER INFORMATION: BPpro-NheI-F

<400> SEQUENCE: 18
tttagctagc ctcgaagttg                                                20

<210> SEQ ID NO 19
<211> LENGTH: 27
<212> TYPE: DNA
<213> ORGANISM: Artificial
<220> FEATURE:
<223> OTHER INFORMATION: Primer BP40pro-BamHI-R
<220> FEATURE:
<221> NAME/KEY: misc_feature
<223> OTHER INFORMATION: Primer BP40pro-BamHI-R

<400> SEQUENCE: 19
ggatccctat gttgagaaaa agggact                                        27

<210> SEQ ID NO 20
<211> LENGTH: 24
<212> TYPE: DNA
<213> ORGANISM: Artificial
<220> FEATURE:
<223> OTHER INFORMATION: DFRproHindIIIF

<400> SEQUENCE: 20
taataagctt acagtgtaat tatc                                           24

<210> SEQ ID NO 21

```
<211> LENGTH: 23
<212> TYPE: DNA
<213> ORGANISM: Artificial
<220> FEATURE:
<223> OTHER INFORMATION: DFRproNheIR

<400> SEQUENCE: 21
ttatgctagc gtgtcaagac cac                                           23

<210> SEQ ID NO 22
<211> LENGTH: 22
<212> TYPE: DNA
<213> ORGANISM: Artificial
<220> FEATURE:
<223> OTHER INFORMATION: DFRproNheIF

<400> SEQUENCE: 22
acacgctagc ataagtctgt tg                                            22

<210> SEQ ID NO 23
<211> LENGTH: 20
<212> TYPE: DNA
<213> ORGANISM: Artificial
<220> FEATURE:
<223> OTHER INFORMATION: DFRproBamHI-R

<400> SEQUENCE: 23 gcttgtgggat ccatcttagg                                              20

<210> SEQ ID NO 24
<211> LENGTH: 25
<212> TYPE: DNA
<213> ORGANISM: Artificial
<220> FEATURE:
<223> OTHER INFORMATION: Primer RrF3H-F

<400> SEQUENCE: 24
aagcttctag ttagacaaaa agcta                                         25

<210> SEQ ID NO 25
<211> LENGTH: 25
<212> TYPE: DNA
<213> ORGANISM: Artificial
<220> FEATURE:
<223> OTHER INFORMATION: Primer RrF3H-R

<400> SEQUENCE: 25
ggatcctctc ttgatatttc cgttc                                         25

<210> SEQ ID NO 26
<211> LENGTH: 33
<212> TYPE: DNA
<213> ORGANISM: Artificial
<220> FEATURE:
<223> OTHER INFORMATION: ADH-BP40Fd

<400> SEQUENCE: 26
caagaaaaat aaatggcaat tctagtcacc gac                                33

<210> SEQ ID NO 27
<211> LENGTH: 20
<212> TYPE: DNA
<213> ORGANISM: Artificial
<220> FEATURE:
<223> OTHER INFORMATION: NcoI-BP40-Rv

<400> SEQUENCE: 27
```

```
ctcgagcgta cgtgagcatc                                              20
```

<210> SEQ ID NO 28
<211> LENGTH: 29
<212> TYPE: DNA
<213> ORGANISM: Artificial
<220> FEATURE:
<223> OTHER INFORMATION: BamHI-ADH-Fd

<400> SEQUENCE: 28

```
cgcggatccg tctatttaac tcagtattc                                    29
```

<210> SEQ ID NO 29
<211> LENGTH: 35
<212> TYPE: DNA
<213> ORGANISM: Artificial
<220> FEATURE:
<223> OTHER INFORMATION: BP40-ADH-Rv

<400> SEQUENCE: 29

```
tagaattgcc atttattttt cttgatttcc ttcac                             35
```

<210> SEQ ID NO 30
<211> LENGTH: 29
<212> TYPE: DNA
<213> ORGANISM: Artificial
<220> FEATURE:
<223> OTHER INFORMATION: BamHI-ADH-Fd

<400> SEQUENCE: 30

```
cgcggatccg tctatttaac tcagtattc                                    29
```

<210> SEQ ID NO 31
<211> LENGTH: 20
<212> TYPE: DNA
<213> ORGANISM: Artificial
<220> FEATURE:
<223> OTHER INFORMATION: NcoI-BP40Rv

<400> SEQUENCE: 31

```
ctcgagcgta cgtgagcatc                                              20
```

<210> SEQ ID NO 32
<211> LENGTH: 27
<212> TYPE: DNA
<213> ORGANISM: Artificial
<220> FEATURE:
<223> OTHER INFORMATION: ADH KpnI Forward

<400> SEQUENCE: 32

```
cggtaccgtc tatttaactc agtattc                                      27
```

<210> SEQ ID NO 33
<211> LENGTH: 25
<212> TYPE: DNA
<213> ORGANISM: Artificial
<220> FEATURE:
<223> OTHER INFORMATION: GUS19R

<400> SEQUENCE: 33

```
tttctacagg acgtaacata aggga                                        25
```

<210> SEQ ID NO 34
<211> LENGTH: 1047
<212> TYPE: DNA

<213> ORGANISM: Chrysanthemum
<220> FEATURE:
<221> NAME/KEY: misc_feature
<223> OTHER INFORMATION: Flavanone 3-hydroxylase (F3H) promoter
<220> FEATURE:
<221> NAME/KEY: primer_bind
<222> LOCATION: (1)..(23)
<220> FEATURE:
<221> NAME/KEY: primer_bind
<222> LOCATION: (1023)..(1047)

<400> SEQUENCE: 34

```
ttacaaaacc atgtgcaaga atgaagaaag aagaaacaat gagggtctaa tatgtaatag      60
ttagcttagc ttttctagta agctaaattt agggttttta tgtaacctcc ctctcttata     120
taaagagggt aggcgtctag ggtttcggta ttcctttcca ttatcttttt cattcatcct     180
ttcatttcat agtattcatc tctaatgaga gtctagacac acgatcatag cgtgtgtata     240
atagttgtag tagttttttt gttttaatta ataaagaaaa ccttattatt agtgatgttg     300
attgtgtttt taatcattcc gctgttttca atcaattgat atcactcata ccctagttga     360
gtcccgatct tgttttcaac aattggtttc agagcctcgt ggctctcgat ctagggttta     420
taagattttc atgtaattag ggtttatact ctaattcatc tattgcagca gatttgaaaa     480
gaaaagaggc agcagatggg gaattgatca catggctact gttcgaacct acaaaggaat     540
atcaatacga gggctcaatt attgtctcgg attcaatgaa ttcacaaggt aaataaacgc     600
ggtactcttt tcattggtcc ttcgttttat ttgtttgaca attaattggg atggctggcg     660
tgtataattc tcaatacatg tctgatttaa tatgtgattg gttgacattc atgtgaaatt     720
aatatactca ttttatgatt acaaagaccc acgatgtata attaattcca atcttgtgga     780
atgggatcca ttgtgaaccg gtgcatgatt gttacggtgg ggattacttt tgattggttc     840
agcattatca tataaccccc gttcaacgga tgcatgctac attggtacgt atacatatac     900
gattcacgtg tggtagttga taactagcgc gatacgcccc cacccccatat ttcttcaatt     960
ttctctacaa atacccatgc caaccttacg aaacactcat tccctctac tcatagacgc    1020
accaagtgtg tgaagaaaaa ataaaaa                                        1047
```

<210> SEQ ID NO 35
<211> LENGTH: 2346
<212> TYPE: DNA
<213> ORGANISM: Chrysanthemum
<220> FEATURE:
<221> NAME/KEY: misc_feature
<223> OTHER INFORMATION: pBluescript SK-F3H9 which contains Flavanone
   3-hydroxylase (F3H) promoter
<220> FEATURE:
<221> NAME/KEY: primer_bind
<222> LOCATION: (1092)..(1114)
<220> FEATURE:
<221> NAME/KEY: primer_bind
<222> LOCATION: (2114)..(2138)

<400> SEQUENCE: 35

```
aagctttcgg gggatgaatt cttcgctacc acgtaattcc ccatggcttt gagtctaact      60
taaagactcg gtaataaaga aaagtgctct ttcgggagac aacccgaatt atccttttta     120
tttcttttat ttcactttt gtttggtttt gtgttttta cattttgcag gaattggaga     180
agaattcaca agtgactaaa acggggacct gttctgtcca acagttacgg cgtaactcat     240
cctcatggtt acgccgtaac atatcctcag tagcgattct ctccaataca taaaccatta     300
cggcgtaatc ccattctatg gttacgccgt agctattctc cagtagcaaa ttgccagttt     360
```

-continued

```
ttaccacaat tacagcttaa ctcctctttc gggttacgtc gtaactatcc tacaattcta     420
atttttccta tattaacaca ataaccttgt attagttttt aaatgaactt tgcgggtatg     480
ttccatgtaa gccctcatga gactacactc gtccacttgg dacaccaagt ggtttaaaat     540
gcttgttgca tatgctaaat gcaaccgtga ttcctacgaa agtgagttag atttcttttt     600
gtttttgttt ttattttct ttttagaatt atgcttgttg gttagtgtga tatcagggaa     660
tgaagtttgc tcgtggatgc ttaagcaaag gcacgattct cttcgtaggc cttctttctt     720
tttaagagca aatttcaggg aagttctcgc tctaattcta ctttctcttc acctttattt     780
aacgtttagt acaaaaggga ctttgtacat cttaagtggg ggggacggga gtagaattat     840
tacttgaact taattgccct cgttttcta gtttatttg aaaaattatg ccatttttaa       900
aattttggca tgttttctt aagctaacta gattagacct tagccgagca ctttataacc     960
cttgatattt tatggtgaga ttagctttat ccgtttctaa ttatttaccc aaatccacta    1020
aattattaga gtgtcggtag cttgtaaact ttagaacttg gtctttgtgt tgggaattgt    1080
cgagttgaag attacaaaac catgtgcaag aatgaagaaa aagaaacaa tgagggtcta    1140 atatgtaata gttagcttag cttttctagt aagctaaatt tagggttttt atgtaacctc    1200
cctctcttat ataagaggg taggcgtcta gggtttcggt attcctttcc attatccttt     1260
tcattcatcc tttcatttca tagtattcat ctctaatgag agtctagaca cacgatcata    1320
gcgtgtgtat aatagttgta gtagttttt tgttttaatt aataaagaaa acccttattat    1380 tagtgatgtt gattgtgttt ttaatcattc cgctgttttc aatcaattga tatcactcat    1440
accctagttg agtcccgatc ttgttttcaa caattggttt cagagcctcg tggctctcga    1500
tctagggttt ataagatttt catgtaatta gggtttatac tctaattcat ctattgcagc    1560
agatttgaaa agaaaagagg cagcagatgg ggaattgatc acatggctac tgttcgaacc    1620
tacaaaggaa tatcaatacg agggctcaat tattgtctcg gattcaatga attcacaagg    1680
taaataaacg cggtactctt ttcattggtc cttcgtttta tttgtttgac aattaattgg    1740
gatggctggc gtgtataatt ctcaatacat gtctgattta atatgtgatt ggttgacatt    1800
catgtgaaat taatatactc atttttatgat tacaaagacc cacgatgtat aattaattcc    1860
aatcttgtgg aatgggatcc attgtgaacc ggtgcatgat tgttacggtg gggattactt    1920
ttgattggtt cagcattatc atataacccc cgttcaacgg atgcatgcta cattggtacg    1980
tatacatata cgattcacgt gtggtagttg ataactagcg cgatacgccc ccaccccata    2040
tttcttcaat tttctctaca aatacccatg ccaaccttac gaaacactca ttcccctcta    2100
ctcatagacg caccaagtgt gtgaagaaaa aataaaaaat ggcacctata tccttgaaat    2160
gggacgataa ttcgctgcat gaaaaccggt tcgtccgtga tgaggacgag cggcctaagg    2220
tgccatacaa caagtttacc aacgagattc ccgttatctc acttaaggga attgacgatg    2280
tggaagagag tagcggtggt atcaaatcac gtagggccga gatttgtgag aagataataa    2340
aagctt                                                               2346
```

<210> SEQ ID NO 36
<211> LENGTH: 55
<212> TYPE: DNA
<213> ORGANISM: Artificial
<220> FEATURE:
<223> OTHER INFORMATION: HANS-F3Hpro1k-Fd

<400> SEQUENCE: 36

```
ccaagcttgg cgcgccgcgg ccgcatttaa atttacaaaa ccatgtgcaa gaatg          55
```

<210> SEQ ID NO 37
<211> LENGTH: 43
<212> TYPE: DNA
<213> ORGANISM: Artificial
<220> FEATURE:
<223> OTHER INFORMATION: SNM-F3Hpro-Rv

<400> SEQUENCE: 37
actagtgcta gcacgcgttt tttattttttt cttcacacac ttg      43

<210> SEQ ID NO 38
<211> LENGTH: 43
<212> TYPE: DNA
<213> ORGANISM: Artificial
<220> FEATURE:
<223> OTHER INFORMATION: NSM-F3Hpro-Rv

<400> SEQUENCE: 38
gctagcacta gtacgcgttt tttattttttt cttcacacac ttg      43

<210> SEQ ID NO 39
<211> LENGTH: 34
<212> TYPE: DNA
<213> ORGANISM: Artificial
<220> FEATURE:
<223> OTHER INFORMATION: BclI-CmF3Hp-Rv

<400> SEQUENCE: 39
ttttgatcat ttttattttt tcttcacac agtg      34

<210> SEQ ID NO 40
<211> LENGTH: 33
<212> TYPE: DNA
<213> ORGANISM: Artificial
<220> FEATURE:
<223> OTHER INFORMATION: ADH-EgF3'5'H-Fd

<400> SEQUENCE: 40
caagaaaaat aaatggctgt tggaaatggc gtt      33

<210> SEQ ID NO 41
<211> LENGTH: 21
<212> TYPE: DNA
<213> ORGANISM: Artificial
<220> FEATURE:
<223> OTHER INFORMATION: HpaI-EgF3'5'H-Rv

<400> SEQUENCE: 41
gttaacgctg agcctagtgc c      21

<210> SEQ ID NO 42
<211> LENGTH: 32
<212> TYPE: DNA
<213> ORGANISM: Artificial
<220> FEATURE:
<223> OTHER INFORMATION: XbaI-ADH-Fd

<400> SEQUENCE: 42
acgcgttcta gagtctattt aactcagtat tc      32

<210> SEQ ID NO 43
<211> LENGTH: 35
<212> TYPE: DNA
<213> ORGANISM: Artificial
<220> FEATURE:

<223> OTHER INFORMATION: EgF3'5'H-ADH-Rv

<400> SEQUENCE: 43
tccaacagcc atttattttt cttgatttcc ttcac　　　　　　　　　　　　　　35

<210> SEQ ID NO 44
<211> LENGTH: 21
<212> TYPE: DNA
<213> ORGANISM: Artificial
<220> FEATURE:
<223> OTHER INFORMATION: HpaI-EgF3'5'H-Rv

<400> SEQUENCE: 44
gttaacgctg agcctagtgc c　　　　　　　　　　　　　　　　　　　　　　21

<210> SEQ ID NO 45
<211> LENGTH: 32
<212> TYPE: DNA
<213> ORGANISM: Artificial
<220> FEATURE:
<223> OTHER INFORMATION: ADH-LeF3'5'H-Fd

<400> SEQUENCE: 45
caagaaaaat aaatggacgc gacawacatt gc　　　　　　　　　　　　　　　32

<210> SEQ ID NO 46
<211> LENGTH: 21
<212> TYPE: DNA
<213> ORGANISM: Artificial
<220> FEATURE:
<223> OTHER INFORMATION: HpaI-LeF3'5'H-Rv

<400> SEQUENCE: 46
gttaacatct cgggcagcac c　　　　　　　　　　　　　　　　　　　　　　21

<210> SEQ ID NO 47
<211> LENGTH: 35
<212> TYPE: DNA
<213> ORGANISM: Artificial
<220> FEATURE:
<223> OTHER INFORMATION: LeF3'5'H-ADH-Rv

<400> SEQUENCE: 47
tgtcgcgtcc atttattttt cttgatttcc ttcac　　　　　　　　　　　　　　35

<210> SEQ ID NO 48
<211> LENGTH: 21
<212> TYPE: DNA
<213> ORGANISM: Artificial
<220> FEATURE:
<223> OTHER INFORMATION: HpaI-LeF3'5'H-Rv

<400> SEQUENCE: 48
gttaacatct cgggcagcac c　　　　　　　　　　　　　　　　　　　　　　21

<210> SEQ ID NO 49
<211> LENGTH: 21
<212> TYPE: DNA
<213> ORGANISM: Artificial
<220> FEATURE:
<223> OTHER INFORMATION: CamF1

<400> SEQUENCE: 49
gtgaagccac catgtctata g　　　　　　　　　　　　　　　　　　　　　　21

-continued

```
<210> SEQ ID NO 50
<211> LENGTH: 22
<212> TYPE: DNA
<213> ORGANISM: Artificial
<220> FEATURE:
<223> OTHER INFORMATION: CamR1

<400> SEQUENCE: 50
gcatttgcct agacagtgta ag                                              22

<210> SEQ ID NO 51
<211> LENGTH: 1585
<212> TYPE: DNA
<213> ORGANISM: Campanula medium
<220> FEATURE:
<221> NAME/KEY: misc_feature
<223> OTHER INFORMATION: Cline #4 pSPB2561
<220> FEATURE:
<221> NAME/KEY: CDS
<222> LOCATION: (12)..(1577)

<400> SEQUENCE: 51
gtgaagccac c atg tct ata gac ata acc att ctc tta tgt gaa ctt gtt          50
            Met Ser Ile Asp Ile Thr Ile Leu Leu Cys Glu Leu Val
              1               5                  10 gct gca att tca ctc tac tta tta acc tac tat ttc att tgt ttc ctc          98
Ala Ala Ile Ser Leu Tyr Leu Leu Thr Tyr Tyr Phe Ile Cys Phe Leu
 15                  20                  25 ttc aaa ccc tct cat cat cac cac cac ctc cct ccc ggc cca acc gga         146
Phe Lys Pro Ser His His His His His Leu Pro Pro Gly Pro Thr Gly
 30                  35                  40                  45 tgg ccg atc att gga tcc ctt cct ctc tta ggc act atg cca cat gtt         194
Trp Pro Ile Ile Gly Ser Leu Pro Leu Leu Gly Thr Met Pro His Val
                 50                  55                  60 tcc tta gcc gac atg gcc gta aaa tac ggg cct ata atg tac cta aaa         242
Ser Leu Ala Asp Met Ala Val Lys Tyr Gly Pro Ile Met Tyr Leu Lys
             65                  70                  75 ctt ggt tca aag ggc acc gtc gtg gcc tca aat cca aaa gcc gcc cga         290
Leu Gly Ser Lys Gly Thr Val Val Ala Ser Asn Pro Lys Ala Ala Arg
         80                  85                  90 gca ttc ttg aaa tcc cat gat gcc aat ttt tct aac cgt ccg att gat         338
Ala Phe Leu Lys Ser His Asp Ala Asn Phe Ser Asn Arg Pro Ile Asp
     95                 100                 105 ggg ggg ccc acc tac ctc gcg tat aat gca caa gac atg gtt ttt gca         386
Gly Gly Pro Thr Tyr Leu Ala Tyr Asn Ala Gln Asp Met Val Phe Ala
110                 115                 120                 125 gaa tat ggc cca aaa tgg aag ctt ttg cga aag cta tgt agc ttg cac         434
Glu Tyr Gly Pro Lys Trp Lys Leu Leu Arg Lys Leu Cys Ser Leu His
                130                 135                 140 atg tta ggc ccg aag gca ctc gag gat tgg gct cat gtc aga gtt tca         482
Met Leu Gly Pro Lys Ala Leu Glu Asp Trp Ala His Val Arg Val Ser
            145                 150                 155 gag gtc ggt cat atg ctc aaa gaa atg tac gag caa tcg agt aag tcc         530
Glu Val Gly His Met Leu Lys Glu Met Tyr Glu Gln Ser Ser Lys Ser
        160                 165                 170 gtg cca gtg gtg gtg cca gag atg tta act tat gcc atg gct aat atg         578
Val Pro Val Val Val Pro Glu Met Leu Thr Tyr Ala Met Ala Asn Met
    175                 180                 185 att gga cga atc ata ctc agt cga cgc cct ttt gtt atc acg agc aaa         626
Ile Gly Arg Ile Ile Leu Ser Arg Arg Pro Phe Val Ile Thr Ser Lys
190                 195                 200                 205 tta gac tcg tct gct tct gct gct tct gtt agt gaa ttc caa tat atg         674
Leu Asp Ser Ser Ala Ser Ala Ala Ser Val Ser Glu Phe Gln Tyr Met
```

```
                    210                 215                     220
gtt atg gag ctc atg agg atg gca ggg ttg ttc aat att ggt gat ttc       722
Val Met Glu Leu Met Arg Met Ala Gly Leu Phe Asn Ile Gly Asp Phe
            225                 230                 235 ata cca tat att gcg tgg atg gat ttg caa ggc att caa cgc gat atg       770
Ile Pro Tyr Ile Ala Trp Met Asp Leu Gln Gly Ile Gln Arg Asp Met
        240                 245                 250 aag gtt ata cag caa aag ttt gat gtc ttg ttg aac aaa atg atc aag       818
Lys Val Ile Gln Gln Lys Phe Asp Val Leu Leu Asn Lys Met Ile Lys
            255                 260                 265 gaa cat aca gaa tcc gct cat gat cgt aaa gat aat cct gat ttt ctt       866
Glu His Thr Glu Ser Ala His Asp Arg Lys Asp Asn Pro Asp Phe Leu
270                 275                 280                 285 gat att ctt atg gcg gct acc caa gaa aac acg gag gga att cag ctt       914
Asp Ile Leu Met Ala Ala Thr Gln Glu Asn Thr Glu Gly Ile Gln Leu
                290                 295                 300 aat ctc gta aat gtt aag gcg ctt ctt ttg gat tta ttc acg gcg ggc       962
Asn Leu Val Asn Val Lys Ala Leu Leu Leu Asp Leu Phe Thr Ala Gly
            305                 310                 315 acg gat aca tcg tcg agt gtg atc gaa tgg gca cta gcc gaa atg ttg      1010
Thr Asp Thr Ser Ser Ser Val Ile Glu Trp Ala Leu Ala Glu Met Leu
        320                 325                 330 aac aat cga cag atc cta aac cgg gcc cac gaa gaa atg gac caa gtc      1058
Asn Asn Arg Gln Ile Leu Asn Arg Ala His Glu Glu Met Asp Gln Val
            335                 340                 345 att ggc aga aac aga aga cta gaa caa tct gac ata cca aac ttg cca      1106
Ile Gly Arg Asn Arg Arg Leu Glu Gln Ser Asp Ile Pro Asn Leu Pro
350                 355                 360                 365 tat ttc caa gcc ata tgc aaa gaa aca ttc cga aaa cac cct tcc acg      1154
Tyr Phe Gln Ala Ile Cys Lys Glu Thr Phe Arg Lys His Pro Ser Thr
                370                 375                 380 ccc tta aac ctc cca aga atc tca aca gaa gaa tgt gaa gtc gaa gga      1202
Pro Leu Asn Leu Pro Arg Ile Ser Thr Glu Glu Cys Glu Val Glu Gly
            385                 390                 395 ttt cgc ata ccc aaa aac act aga cta ata gtg aac ata tgg gca ata      1250
Phe Arg Ile Pro Lys Asn Thr Arg Leu Ile Val Asn Ile Trp Ala Ile
        400                 405                 410 ggg aga gac cct aaa gtg tgg gaa aat cca ttg gat ttt acc ccg gaa      1298
Gly Arg Asp Pro Lys Val Trp Glu Asn Pro Leu Asp Phe Thr Pro Glu
            415                 420                 425 cga ttc ttg agt gaa aaa cac gcg aaa att gat ccg cga ggt aat cat      1346
Arg Phe Leu Ser Glu Lys His Ala Lys Ile Asp Pro Arg Gly Asn His
430                 435                 440                 445 ttt gag tta atc cca ttt ggg gcg gga cgg agg ata tgt gca ggg gct      1394
Phe Glu Leu Ile Pro Phe Gly Ala Gly Arg Arg Ile Cys Ala Gly Ala
                450                 455                 460 aga atg gga gcg gcc tcg gtc gag tac att tta ggt aca ttg gtg cac      1442
Arg Met Gly Ala Ala Ser Val Glu Tyr Ile Leu Gly Thr Leu Val His
            465                 470                 475 tca ttt gat tgg aaa ttg cct gat gga gtt gtg gaa gtt aat atg gaa      1490
Ser Phe Asp Trp Lys Leu Pro Asp Gly Val Val Glu Val Asn Met Glu
        480                 485                 490 gag agc ttt ggg ata gca ttg cag aaa aag atg cct ctt tct gct att      1538
Glu Ser Phe Gly Ile Ala Leu Gln Lys Lys Met Pro Leu Ser Ala Ile
            495                 500                 505 gtt act cca aga ttg cct cca agt gct tac act gtc tag gcaaatgc         1585
Val Thr Pro Arg Leu Pro Pro Ser Ala Tyr Thr Val
510                 515                 520
```

<210> SEQ ID NO 52
<211> LENGTH: 521
<212> TYPE: PRT
<213> ORGANISM: Campanula medium

<400> SEQUENCE: 52

```
Met Ser Ile Asp Ile Thr Ile Leu Leu Cys Glu Leu Val Ala Ala Ile
1               5                   10                  15

Ser Leu Tyr Leu Leu Thr Tyr Tyr Phe Ile Cys Phe Leu Phe Lys Pro
            20                  25                  30

Ser His His His His Leu Pro Pro Gly Pro Thr Gly Trp Pro Ile
        35                  40                  45

Ile Gly Ser Leu Pro Leu Leu Gly Thr Met Pro His Val Ser Leu Ala
    50                  55                  60

Asp Met Ala Val Lys Tyr Gly Pro Ile Met Tyr Leu Lys Leu Gly Ser
65                  70                  75                  80

Lys Gly Thr Val Val Ala Ser Asn Pro Lys Ala Ala Arg Ala Phe Leu
                85                  90                  95

Lys Ser His Asp Ala Asn Phe Ser Asn Arg Pro Ile Asp Gly Gly Pro
            100                 105                 110

Thr Tyr Leu Ala Tyr Asn Ala Gln Asp Met Val Phe Ala Glu Tyr Gly
        115                 120                 125

Pro Lys Trp Lys Leu Leu Arg Lys Leu Cys Ser Leu His Met Leu Gly
130                 135                 140

Pro Lys Ala Leu Glu Asp Trp Ala His Val Arg Val Ser Glu Val Gly
145                 150                 155                 160

His Met Leu Lys Glu Met Tyr Glu Gln Ser Ser Lys Ser Val Pro Val
                165                 170                 175

Val Val Pro Glu Met Leu Thr Tyr Ala Met Ala Asn Met Ile Gly Arg
            180                 185                 190

Ile Ile Leu Ser Arg Arg Pro Phe Val Ile Thr Ser Lys Leu Asp Ser
        195                 200                 205

Ser Ala Ser Ala Ala Ser Val Ser Glu Phe Gln Tyr Met Val Met Glu
    210                 215                 220

Leu Met Arg Met Ala Gly Leu Phe Asn Ile Gly Asp Phe Ile Pro Tyr
225                 230                 235                 240

Ile Ala Trp Met Asp Leu Gln Gly Ile Gln Arg Asp Met Lys Val Ile
                245                 250                 255

Gln Gln Lys Phe Asp Val Leu Leu Asn Lys Met Ile Lys Glu His Thr
            260                 265                 270

Glu Ser Ala His Asp Arg Lys Asp Asn Pro Asp Phe Leu Asp Ile Leu
        275                 280                 285

Met Ala Ala Thr Gln Glu Asn Thr Glu Gly Ile Gln Leu Asn Leu Val
    290                 295                 300

Asn Val Lys Ala Leu Leu Leu Asp Leu Phe Thr Ala Gly Thr Asp Thr
305                 310                 315                 320

Ser Ser Ser Val Ile Glu Trp Ala Leu Ala Glu Met Leu Asn Asn Arg
                325                 330                 335

Gln Ile Leu Asn Arg Ala His Glu Glu Met Asp Gln Val Ile Gly Arg
            340                 345                 350

Asn Arg Arg Leu Glu Gln Ser Asp Ile Pro Asn Leu Pro Tyr Phe Gln
        355                 360                 365

Ala Ile Cys Lys Glu Thr Phe Arg Lys His Pro Ser Thr Pro Leu Asn
    370                 375                 380
```

Leu Pro Arg Ile Ser Thr Glu Glu Cys Glu Val Glu Gly Phe Arg Ile
385                 390                 395                 400

Pro Lys Asn Thr Arg Leu Ile Val Asn Ile Trp Ala Ile Gly Arg Asp
            405                 410                 415

Pro Lys Val Trp Glu Asn Pro Leu Asp Phe Thr Pro Glu Arg Phe Leu
        420                 425                 430

Ser Glu Lys His Ala Lys Ile Asp Pro Arg Gly Asn His Phe Glu Leu
        435                 440                 445

Ile Pro Phe Gly Ala Gly Arg Arg Ile Cys Ala Gly Ala Arg Met Gly
    450                 455                 460

Ala Ala Ser Val Glu Tyr Ile Leu Gly Thr Leu Val His Ser Phe Asp
465                 470                 475                 480

Trp Lys Leu Pro Asp Gly Val Val Glu Val Asn Met Glu Glu Ser Phe
            485                 490                 495

Gly Ile Ala Leu Gln Lys Lys Met Pro Leu Ser Ala Ile Val Thr Pro
        500                 505                 510

Arg Leu Pro Pro Ser Ala Tyr Thr Val
        515                 520

<210> SEQ ID NO 53
<211> LENGTH: 34
<212> TYPE: DNA
<213> ORGANISM: Artificial
<220> FEATURE:
<223> OTHER INFORMATION: ADH-Campa-Fd

<400> SEQUENCE: 53
caagaaaaat aaatgtctat agacataacc attc                              34

<210> SEQ ID NO 54
<211> LENGTH: 21
<212> TYPE: DNA
<213> ORGANISM: Artificial
<220> FEATURE:
<223> OTHER INFORMATION: HpaI-Campa-Rv

<400> SEQUENCE: 54
gttaacatct ctggcaccac c                                            21

<210> SEQ ID NO 55
<211> LENGTH: 35
<212> TYPE: DNA
<213> ORGANISM: Artificial
<220> FEATURE:
<223> OTHER INFORMATION: Campa-ADH-Rv

<400> SEQUENCE: 55
gtctatagac atttattttt cttgatttcc ttcac                             35

<210> SEQ ID NO 56
<211> LENGTH: 21
<212> TYPE: DNA
<213> ORGANISM: Artificial
<220> FEATURE:
<223> OTHER INFORMATION: HpaI-Campa-Rv

<400> SEQUENCE: 56
gttaacatct ctggcaccac c                                            21

<210> SEQ ID NO 57
<211> LENGTH: 33
<212> TYPE: DNA

<210> SEQ ID NO 57
<211> LENGTH: 33
<212> TYPE: DNA
<213> ORGANISM: Artificial
<220> FEATURE:
<223> OTHER INFORMATION: ADH-ScF3'5'H-Fd

<400> SEQUENCE: 57
caagaaaaat aaatgagcat tctaaccctc atc                33

<210> SEQ ID NO 58
<211> LENGTH: 24
<212> TYPE: DNA
<213> ORGANISM: Artificial
<220> FEATURE:
<223> OTHER INFORMATION: NdeI-ScF3'5'H-Rv

<400> SEQUENCE: 58
catatgttta gctccagaat ttgg                24

<210> SEQ ID NO 59
<211> LENGTH: 35
<212> TYPE: DNA
<213> ORGANISM: Artificial
<220> FEATURE:
<223> OTHER INFORMATION: ScF3'5'H-ADH-Rv

<400> SEQUENCE: 59
tagaatgctc atttattttt cttgatttcc ttcac                35

<210> SEQ ID NO 60
<211> LENGTH: 24
<212> TYPE: DNA
<213> ORGANISM: Artificial
<220> FEATURE:
<223> OTHER INFORMATION: NdeI-ScF3'5'H-Rv

<400> SEQUENCE: 60
catatgttta gctccagaat ttgg                24

<210> SEQ ID NO 61
<211> LENGTH: 34
<212> TYPE: DNA
<213> ORGANISM: Artificial
<220> FEATURE:
<223> OTHER INFORMATION: ADH-Gentian-Fd

<400> SEQUENCE: 61
caagaaaaat aaatgtcacc catttacacc accc                34

<210> SEQ ID NO 62
<211> LENGTH: 20
<212> TYPE: DNA
<213> ORGANISM: Artificial
<220> FEATURE:
<223> OTHER INFORMATION: SalI-GentianF3'5'H-Rv

<400> SEQUENCE: 62
gtcgacgcta ttgctaagcc                20

<210> SEQ ID NO 63
<211> LENGTH: 35
<212> TYPE: DNA
<213> ORGANISM: Artificial
<220> FEATURE:
<223> OTHER INFORMATION: Gentian-ADH-Rv

<400> SEQUENCE: 63
aatgggtgac atttattttt cttgatttcc ttcac                35

<210> SEQ ID NO 64
<211> LENGTH: 20
<212> TYPE: DNA
<213> ORGANISM: Artificial
<220> FEATURE:
<223> OTHER INFORMATION: SalI-GentianF3'5'H-Rv

<400> SEQUENCE: 64
gtcgacgcta ttgctaagcc                                           20

<210> SEQ ID NO 65
<211> LENGTH: 36
<212> TYPE: DNA
<213> ORGANISM: Artificial
<220> FEATURE:
<223> OTHER INFORMATION: ADH-Verbena-Fd

<400> SEQUENCE: 65
caagaaaaat aaatgacgtt ttcagagctt ataaac                         36

<210> SEQ ID NO 66
<211> LENGTH: 22
<212> TYPE: DNA
<213> ORGANISM: Artificial
<220> FEATURE:
<223> OTHER INFORMATION: NcoI-Verbena-F3'5'H-Rv

<400> SEQUENCE: 66
ccatggagta aatcagcatc tc                                        22

<210> SEQ ID NO 67
<211> LENGTH: 35
<212> TYPE: DNA
<213> ORGANISM: Artificial
<220> FEATURE:
<223> OTHER INFORMATION: Verbena-ADH-Rv

<400> SEQUENCE: 67
tgaaaacgtc atttattttt cttgatttcc ttcac                          35

<210> SEQ ID NO 68
<211> LENGTH: 22
<212> TYPE: DNA
<213> ORGANISM: Artificial
<220> FEATURE:
<223> OTHER INFORMATION: NcoI-VerbenaF3'5'H-Rv

<400> SEQUENCE: 68
ccatggagta aatcagcatc tc                                        22

<210> SEQ ID NO 69
<211> LENGTH: 1755
<212> TYPE: DNA
<213> ORGANISM: Antirrhinum kellogii
<220> FEATURE:
<221> NAME/KEY: misc_feature
<223> OTHER INFORMATION: F3'5'HcDNA#1 pSPB3145
<220> FEATURE:
<221> NAME/KEY: CDS
<222> LOCATION: (73)..(1602)

<400> SEQUENCE: 69
ttcggcacga gggtaccttt agtatgttca atctctagtt ttttattaat cacaactcaa    60
tagataatcg tc atg cag ata ata att ccg gtc ctc ctg aag gag ctc acc   111
            Met Gln Ile Ile Ile Pro Val Leu Leu Lys Glu Leu Thr

|       |       |       |       |       |       |       |       |       |       |       |       |       |       |       |       |      |
|-------|-------|-------|-------|-------|-------|-------|-------|-------|-------|-------|-------|-------|-------|-------|-------|------|
|       |       | 1     |       |       |       | 5     |       |       |       |       | 10    |       |       |       |       |      |
| gta   | gca   | gca   | tta   | ctc   | tat   | gtt   | ttc   | act   | aac   | att   | ctc   | atc   | cgc   | tca   | ctt   | 159  |
| Val   | Ala   | Ala   | Leu   | Leu   | Tyr   | Val   | Phe   | Thr   | Asn   | Ile   | Leu   | Ile   | Arg   | Ser   | Leu   |      |
|       |       | 15    |       |       |       | 20    |       |       |       |       | 25    |       |       |       |       |      |
| ctc   | aca   | aga   | ccc   | tgt   | cac   | cgt   | ctc   | ccg   | cca   | ggg   | cca   | aga   | ggc   | ttt   | cca   | 207  |
| Leu   | Thr   | Arg   | Pro   | Cys   | His   | Arg   | Leu   | Pro   | Pro   | Gly   | Pro   | Arg   | Gly   | Phe   | Pro   |      |
| 30    |       |       |       | 35    |       |       |       |       | 40    |       |       |       |       | 45    |       |      |
| gta   | gtc   | ggc   | gct   | ctt   | cca   | ctc   | cta   | ggc   | agc   | atg   | cca   | cac   | gtg   | gcg   | ctc   | 255  |
| Val   | Val   | Gly   | Ala   | Leu   | Pro   | Leu   | Leu   | Gly   | Ser   | Met   | Pro   | His   | Val   | Ala   | Leu   |      |
|       |       |       |       | 50    |       |       |       |       | 55    |       |       |       |       | 60    |       |      |
| gcc   | aaa   | atg   | tcc   | aaa   | act   | tat   | ggt   | ccc   | gtc   | ata   | tac   | cta   | aaa   | gta   | ggc   | 303  |
| Ala   | Lys   | Met   | Ser   | Lys   | Thr   | Tyr   | Gly   | Pro   | Val   | Ile   | Tyr   | Leu   | Lys   | Val   | Gly   |      |
|       |       |       | 65    |       |       |       |       | 70    |       |       |       |       | 75    |       |       |      |
| gca   | cac   | ggc   | atg   | gca   | gtg   | gcc   | tca   | act   | cct   | gaa   | tcc   | gcc   | aaa   | gcg   | ttc   | 351  |
| Ala   | His   | Gly   | Met   | Ala   | Val   | Ala   | Ser   | Thr   | Pro   | Glu   | Ser   | Ala   | Lys   | Ala   | Phe   |      |
|       |       | 80    |       |       |       |       | 85    |       |       |       |       | 90    |       |       |       |      |
| ctc   | aaa   | acc   | cta   | gac   | acc   | aac   | ttc   | tcc   | aac   | cgc   | ccg   | cca   | aat   | gcc   | ggt   | 399  |
| Leu   | Lys   | Thr   | Leu   | Asp   | Thr   | Asn   | Phe   | Ser   | Asn   | Arg   | Pro   | Pro   | Asn   | Ala   | Gly   |      |
|       | 95    |       |       |       |       | 100   |       |       |       |       | 105   |       |       |       |       |      |
| gcc   | act   | cac   | ctg   | gct   | tat   | aac   | tca   | caa   | gac   | atg   | gtg   | ttt   | gcc   | gcc   | tac   | 447  |
| Ala   | Thr   | His   | Leu   | Ala   | Tyr   | Asn   | Ser   | Gln   | Asp   | Met   | Val   | Phe   | Ala   | Ala   | Tyr   |      |
| 110   |       |       |       |       | 115   |       |       |       |       | 120   |       |       |       |       | 125   |      |
| ggc   | ccg   | agg   | tgg   | aga   | ttg   | ctt   | aga   | aag   | ttg   | agc   | aat   | ctc   | cac   | atg   | ttg   | 495  |
| Gly   | Pro   | Arg   | Trp   | Arg   | Leu   | Leu   | Arg   | Lys   | Leu   | Ser   | Asn   | Leu   | His   | Met   | Leu   |      |
|       |       |       |       | 130   |       |       |       |       | 135   |       |       |       |       | 140   |       |      |
| ggg   | act   | aag   | gct   | tta   | gac   | gat   | tgg   | gca   | aat   | gtt   | agg   | gtt   | tcg   | gag   | gtt   | 543  |
| Gly   | Thr   | Lys   | Ala   | Leu   | Asp   | Asp   | Trp   | Ala   | Asn   | Val   | Arg   | Val   | Ser   | Glu   | Val   |      |
|       |       |       | 145   |       |       |       |       | 150   |       |       |       |       | 155   |       |       |      |
| gga   | tac   | atg   | tta   | gag   | gac   | atg   | cat   | ggg   | gca   | agt   | ggc   | cgc   | gga   | gag   | gcg   | 591  |
| Gly   | Tyr   | Met   | Leu   | Glu   | Asp   | Met   | His   | Gly   | Ala   | Ser   | Gly   | Arg   | Gly   | Glu   | Ala   |      |
|       |       | 160   |       |       |       |       | 165   |       |       |       |       | 170   |       |       |       |      |
| gtg   | ggt   | gtg   | ccg   | ggg   | atg   | ttg   | gtg   | tac   | gca   | atg   | gct   | aat   | atg   | ata   | gga   | 639  |
| Val   | Gly   | Val   | Pro   | Gly   | Met   | Leu   | Val   | Tyr   | Ala   | Met   | Ala   | Asn   | Met   | Ile   | Gly   |      |
|       | 175   |       |       |       |       | 180   |       |       |       |       | 185   |       |       |       |       |      |
| cag   | gtg   | ata   | ctt   | agt   | cgg   | cgt   | gtt   | ttc   | gtg   | acg   | aga   | gga   | gaa   | gaa   | ttg   | 687  |
| Gln   | Val   | Ile   | Leu   | Ser   | Arg   | Arg   | Val   | Phe   | Val   | Thr   | Arg   | Gly   | Glu   | Glu   | Leu   |      |
| 190   |       |       |       |       | 195   |       |       |       |       | 200   |       |       |       |       | 205   |      |
| aac   | gag   | ttt   | aag   | gat   | atg   | gtg   | gtg   | gag   | ctc   | atg   | act   | tcg   | gct   | gga   | tat   | 735  |
| Asn   | Glu   | Phe   | Lys   | Asp   | Met   | Val   | Val   | Glu   | Leu   | Met   | Thr   | Ser   | Ala   | Gly   | Tyr   |      |
|       |       |       |       | 210   |       |       |       |       | 215   |       |       |       |       | 220   |       |      |
| ttc   | aat   | att   | ggt   | gat   | ttt   | att   | ccg   | tct   | ttt   | gct   | tgg   | atg   | gat   | ttg   | caa   | 783  |
| Phe   | Asn   | Ile   | Gly   | Asp   | Phe   | Ile   | Pro   | Ser   | Phe   | Ala   | Trp   | Met   | Asp   | Leu   | Gln   |      |
|       |       |       | 225   |       |       |       |       | 230   |       |       |       |       | 235   |       |       |      |
| gga   | ata   | gag   | aag   | gga   | atg   | aag   | ggc   | ttg   | cac   | aaa   | aag   | ttt   | gat   | gat   | ttg   | 831  |
| Gly   | Ile   | Glu   | Lys   | Gly   | Met   | Lys   | Gly   | Leu   | His   | Lys   | Lys   | Phe   | Asp   | Asp   | Leu   |      |
|       |       | 240   |       |       |       |       | 245   |       |       |       |       | 250   |       |       |       |      |
| atc   | agt   | aga   | atg   | ttg   | gag   | gaa   | cac   | ctg   | gcg   | tca   | gct   | cat   | atc   | cga   | aag   | 879  |
| Ile   | Ser   | Arg   | Met   | Leu   | Glu   | Glu   | His   | Leu   | Ala   | Ser   | Ala   | His   | Ile   | Arg   | Lys   |      |
| 255   |       |       |       |       | 260   |       |       |       |       | 265   |       |       |       |       |       |      |
| gag   | aaa   | cct   | gat   | ttt   | ctt   | gat   | gtc   | att   | ttg   | gct   | aat   | cgt   | gat   | act   | ttg   | 927  |
| Glu   | Lys   | Pro   | Asp   | Phe   | Leu   | Asp   | Val   | Ile   | Leu   | Ala   | Asn   | Arg   | Asp   | Thr   | Leu   |      |
| 270   |       |       |       |       | 275   |       |       |       |       | 280   |       |       |       |       | 285   |      |
| gag   | gga   | gag   | agg   | ctt   | acc   | act   | tct   | aac   | atc   | aag   | gct   | ctt   | tta   | ctg   | aac   | 975  |
| Glu   | Gly   | Glu   | Arg   | Leu   | Thr   | Thr   | Ser   | Asn   | Ile   | Lys   | Ala   | Leu   | Leu   | Leu   | Asn   |      |
|       |       |       | 290   |       |       |       |       | 295   |       |       |       |       | 300   |       |       |      |
| ttg   | ttc   | acc   | gcc   | ggt   | acg   | gat   | aca   | tct   | tcg   | agc   | aca   | ata   | gag   | tgg   | gcg   | 1023 |
| Leu   | Phe   | Thr   | Ala   | Gly   | Thr   | Asp   | Thr   | Ser   | Ser   | Ser   | Thr   | Ile   | Glu   | Trp   | Ala   |      |
|       |       | 305   |       |       |       |       | 310   |       |       |       |       | 315   |       |       |       |      |
| ctg   | gcg   | gag   | atg   | ata   | aaa   | aac   | ccg   | gcg   | atc   | ctc   | aag   | aaa   | gca   | cac   | gat   | 1071 |

```
Leu Ala Glu Met Ile Lys Asn Pro Ala Ile Leu Lys Lys Ala His Asp
            320                 325                 330 gaa atg gat caa gtc gta ggc cgg aat cga cgt tta atg gag tcg gac    1119
Glu Met Asp Gln Val Val Gly Arg Asn Arg Arg Leu Met Glu Ser Asp
335                 340                 345 ata ccc aaa ctt cca tac cta caa gcg ata tgc aag gaa tca ttt cgt    1167
Ile Pro Lys Leu Pro Tyr Leu Gln Ala Ile Cys Lys Glu Ser Phe Arg
350                 355                 360                 365 aag cac cct tcc act cct tta aat ctg ccc cga atc tct tca caa gca    1215
Lys His Pro Ser Thr Pro Leu Asn Leu Pro Arg Ile Ser Ser Gln Ala
                370                 375                 380 tgc acg gtg aac ggt tac tac ata ccg aag aac acg agg ctc aac gtc    1263
Cys Thr Val Asn Gly Tyr Tyr Ile Pro Lys Asn Thr Arg Leu Asn Val
            385                 390                 395 aac ata tgg gcg atc gga agg gat ccc aac gtg tgg gag aat ccc ctg    1311
Asn Ile Trp Ala Ile Gly Arg Asp Pro Asn Val Trp Glu Asn Pro Leu
        400                 405                 410 gaa ttc aac ccc gac agg ttc atg tcc ggt aag aat gca aag ctc gat    1359
Glu Phe Asn Pro Asp Arg Phe Met Ser Gly Lys Asn Ala Lys Leu Asp
    415                 420                 425 ccg aga gga aat gat ttt gaa ctc att ccg ttc ggg gct ggt cga agg    1407
Pro Arg Gly Asn Asp Phe Glu Leu Ile Pro Phe Gly Ala Gly Arg Arg
430                 435                 440                 445 att tgt gcg gga gcg agg atg ggg ata gtt ctt gtg gaa tat ata ttg    1455
Ile Cys Ala Gly Ala Arg Met Gly Ile Val Leu Val Glu Tyr Ile Leu
                450                 455                 460 gga agt ttg gtg cat tct ttt gat tgg aaa ttg ccc gaa gga gtg aag    1503
Gly Ser Leu Val His Ser Phe Asp Trp Lys Leu Pro Glu Gly Val Lys
            465                 470                 475 gag atg aat ttg gat gag gct ttt ggg ctt gct ttg caa aaa gct gtt    1551
Glu Met Asn Leu Asp Glu Ala Phe Gly Leu Ala Leu Gln Lys Ala Val
        480                 485                 490 cct ctt gca gca atg gtt act ccg agg ttg cct tca aat tgt tat gct    1599
Pro Leu Ala Ala Met Val Thr Pro Arg Leu Pro Ser Asn Cys Tyr Ala
    495                 500                 505 cct taagtaatag tatttaagtg cgtcggaata tcgaagtcta tatgattttc         1652
Pro
510 ttgtgcttgt ttctatccac tatgttgtaa gaattcatct ccgatcctct ggtggtcatg  1712 gctatatatc gtaattcttt ttcgaaaaaa aaaaaaaaaa aaa                    1755

<210> SEQ ID NO 70
<211> LENGTH: 510
<212> TYPE: PRT
<213> ORGANISM: Antirrhinum kellogii

<400> SEQUENCE: 70

Met Gln Ile Ile Ile Pro Val Leu Leu Lys Glu Leu Thr Val Ala Ala
1               5                   10                  15

Leu Leu Tyr Val Phe Thr Asn Ile Leu Ile Arg Ser Leu Leu Thr Arg
            20                  25                  30

Pro Cys His Arg Leu Pro Pro Gly Pro Arg Gly Phe Pro Val Val Gly
        35                  40                  45

Ala Leu Pro Leu Leu Gly Ser Met Pro His Val Ala Leu Ala Lys Met
    50                  55                  60

Ser Lys Thr Tyr Gly Pro Val Ile Tyr Leu Lys Val Gly Ala His Gly
65                  70                  75                  80

Met Ala Val Ala Ser Thr Pro Glu Ser Ala Lys Ala Phe Leu Lys Thr
```

```
                    85                  90                  95
Leu Asp Thr Asn Phe Ser Asn Arg Pro Pro Asn Ala Gly Ala Thr His
                100                 105                 110
Leu Ala Tyr Asn Ser Gln Asp Met Val Phe Ala Ala Tyr Gly Pro Arg
            115                 120                 125
Trp Arg Leu Leu Arg Lys Leu Ser Asn Leu His Met Leu Gly Thr Lys
        130                 135                 140
Ala Leu Asp Asp Trp Ala Asn Val Arg Val Ser Glu Val Gly Tyr Met
145                 150                 155                 160
Leu Glu Asp Met His Gly Ala Ser Gly Arg Gly Glu Ala Val Gly Val
                165                 170                 175
Pro Gly Met Leu Val Tyr Ala Met Ala Asn Met Ile Gly Gln Val Ile
                180                 185                 190
Leu Ser Arg Arg Val Phe Val Thr Arg Gly Glu Glu Leu Asn Glu Phe
            195                 200                 205
Lys Asp Met Val Val Glu Leu Met Thr Ser Ala Gly Tyr Phe Asn Ile
        210                 215                 220
Gly Asp Phe Ile Pro Ser Phe Ala Trp Met Asp Leu Gln Gly Ile Glu
225                 230                 235                 240
Lys Gly Met Lys Gly Leu His Lys Lys Phe Asp Asp Leu Ile Ser Arg
                245                 250                 255
Met Leu Glu Glu His Leu Ala Ser Ala His Ile Arg Lys Glu Lys Pro
                260                 265                 270
Asp Phe Leu Asp Val Ile Leu Ala Asn Arg Asp Thr Leu Glu Gly Glu
            275                 280                 285
Arg Leu Thr Thr Ser Asn Ile Lys Ala Leu Leu Leu Asn Leu Phe Thr
        290                 295                 300
Ala Gly Thr Asp Thr Ser Ser Ser Thr Ile Glu Trp Ala Leu Ala Glu
305                 310                 315                 320
Met Ile Lys Asn Pro Ala Ile Leu Lys Lys Ala His Asp Glu Met Asp
                325                 330                 335
Gln Val Val Gly Arg Asn Arg Arg Leu Met Glu Ser Asp Ile Pro Lys
                340                 345                 350
Leu Pro Tyr Leu Gln Ala Ile Cys Lys Glu Ser Phe Arg Lys His Pro
            355                 360                 365
Ser Thr Pro Leu Asn Leu Pro Arg Ile Ser Ser Gln Ala Cys Thr Val
        370                 375                 380
Asn Gly Tyr Tyr Ile Pro Lys Asn Thr Arg Leu Asn Val Asn Ile Trp
385                 390                 395                 400
Ala Ile Gly Arg Asp Pro Asn Val Trp Glu Asn Pro Leu Glu Phe Asn
                405                 410                 415
Pro Asp Arg Phe Met Ser Gly Lys Asn Ala Lys Leu Asp Pro Arg Gly
                420                 425                 430
Asn Asp Phe Glu Leu Ile Pro Phe Gly Ala Gly Arg Arg Ile Cys Ala
            435                 440                 445
Gly Ala Arg Met Gly Ile Val Leu Val Glu Tyr Ile Leu Gly Ser Leu
        450                 455                 460
Val His Ser Phe Asp Trp Lys Leu Pro Glu Gly Val Lys Glu Met Asn
465                 470                 475                 480
Leu Asp Glu Ala Phe Gly Leu Ala Leu Gln Lys Ala Val Pro Leu Ala
                485                 490                 495
Ala Met Val Thr Pro Arg Leu Pro Ser Asn Cys Tyr Ala Pro
                500                 505                 510
```

<210> SEQ ID NO 71
<211> LENGTH: 1811
<212> TYPE: DNA
<213> ORGANISM: Antirrhinum kellogii
<220> FEATURE:
<221> NAME/KEY: misc_feature
<223> OTHER INFORMATION: F3'5'cDNA#12 pSPB3146
<220> FEATURE:
<221> NAME/KEY: CDS
<222> LOCATION: (86)..(1615)

<400> SEQUENCE: 71

```
gatactaaaa accatccaaa ttaagtacct ttagtatgtt caatctctag ttttttttatt      60 aatcacaact caatagataa tcgtc atg cag ata ata att ccg gtc ctc ctg         112
                            Met Gln Ile Ile Ile Pro Val Leu Leu
                            1               5 aag gag ctc acc gta gca gca tta ctc tat gtt ttc act aac att ctc         160
Lys Glu Leu Thr Val Ala Ala Leu Leu Tyr Val Phe Thr Asn Ile Leu
10              15                  20                  25 atc cgc tca ctt ctc aca aga ccc cgt cac cgt ctc ccg cca ggg cca         208
Ile Arg Ser Leu Leu Thr Arg Pro Arg His Arg Leu Pro Pro Gly Pro
            30                  35                  40 aga ggc ttt cca gta gtc ggc gct ctt cca ctc cta ggc agc atg cca         256
Arg Gly Phe Pro Val Val Gly Ala Leu Pro Leu Leu Gly Ser Met Pro
        45                  50                  55 cac gtg gcg ctc gcc aaa atg tcc aaa act tat ggt ccc gtc ata tac         304
His Val Ala Leu Ala Lys Met Ser Lys Thr Tyr Gly Pro Val Ile Tyr
    60                  65                  70 cta aaa gta ggc gca cac ggc atg gca gtg gcc tca act cct gaa tcc         352
Leu Lys Val Gly Ala His Gly Met Ala Val Ala Ser Thr Pro Glu Ser
75                  80                  85 gcc aaa gcg ttc ctc aaa acc cta gac acc aac ttc tcc aac cgc ccg         400
Ala Lys Ala Phe Leu Lys Thr Leu Asp Thr Asn Phe Ser Asn Arg Pro
90              95                  100                 105 cca aat gcc ggt gcc act cac ctg gct tat aac tca caa gac atg gtg         448
Pro Asn Ala Gly Ala Thr His Leu Ala Tyr Asn Ser Gln Asp Met Val
            110                 115                 120 ttt gcc gcc tac ggc ccg agg tgg aga ttg ctt aga aag ttg agc aat         496
Phe Ala Ala Tyr Gly Pro Arg Trp Arg Leu Leu Arg Lys Leu Ser Asn
        125                 130                 135 ctc cac atg ttg ggg act aag gct tta gac gat tgg gca aat gtt agg         544
Leu His Met Leu Gly Thr Lys Ala Leu Asp Asp Trp Ala Asn Val Arg
    140                 145                 150 gtt tcg gag gtt gga tac atg tta gag gac atg cat ggg gca agt ggc         592
Val Ser Glu Val Gly Tyr Met Leu Glu Asp Met His Gly Ala Ser Gly
155                 160                 165 cgc gga aag gtg gtg ggt gtg ccg ggg atg ttg gtg tac gca atg gct         640
Arg Gly Lys Val Val Gly Val Pro Gly Met Leu Val Tyr Ala Met Ala
170                 175                 180                 185 aat atg ata gga cag gtg ata ctt agt cgg cgt gtt ttc gtg acg aga         688
Asn Met Ile Gly Gln Val Ile Leu Ser Arg Arg Val Phe Val Thr Arg
            190                 195                 200 gaa gaa gaa ttg aac gag ttt aag gat atg gtg gtg gag ctc atg act         736
Glu Glu Glu Leu Asn Glu Phe Lys Asp Met Val Val Glu Leu Met Thr
        205                 210                 215 tcg gct gga tat ttc aat att ggt gat ttt att ccg tct ttt gca tgg         784
Ser Ala Gly Tyr Phe Asn Ile Gly Asp Phe Ile Pro Ser Phe Ala Trp
    220                 225                 230 atg gat ttg caa gga ata gag aag gga atg aag ggt ttg cac aaa aag         832
Met Asp Leu Gln Gly Ile Glu Lys Gly Met Lys Gly Leu His Lys Lys
```

```
                235                 240                 245
ttt gat gat ttg atc agt aga atg ttg aag gaa cac ctg gcg tca gct      880
Phe Asp Asp Leu Ile Ser Arg Met Leu Lys Glu His Leu Ala Ser Ala
250                 255                 260                 265 cat atc cga aag gag aaa cct gat ttt ctt gat gtc att ttg gct aat      928
His Ile Arg Lys Glu Lys Pro Asp Phe Leu Asp Val Ile Leu Ala Asn
                270                 275                 280 cgt gat act ttg gag gga gag agg ctt acc act tct aac atc aag gct      976
Arg Asp Thr Leu Glu Gly Glu Arg Leu Thr Thr Ser Asn Ile Lys Ala
            285                 290                 295 ctt tta ctg aac ttg ttc acc gcc ggt acg gat aca tct tcg agc aca     1024
Leu Leu Leu Asn Leu Phe Thr Ala Gly Thr Asp Thr Ser Ser Ser Thr
        300                 305                 310 ata gag tgg gcg ctg gcg gag atg ata aaa aac ccg gcg atc ctc aag     1072
Ile Glu Trp Ala Leu Ala Glu Met Ile Lys Asn Pro Ala Ile Leu Lys
    315                 320                 325 aaa gca cat gat gaa atg gat caa gtc gta ggc tgg aat cga cgt tta     1120
Lys Ala His Asp Glu Met Asp Gln Val Val Gly Trp Asn Arg Arg Leu
330                 335                 340                 345 atg gag tcg gac ata ccc aaa ctt cca tac cta caa gcg ata tgc aag     1168
Met Glu Ser Asp Ile Pro Lys Leu Pro Tyr Leu Gln Ala Ile Cys Lys
                350                 355                 360 gaa tca ttt cgt aag cac cct tcc act cct tta aat ctg ccc cga atc     1216
Glu Ser Phe Arg Lys His Pro Ser Thr Pro Leu Asn Leu Pro Arg Ile
            365                 370                 375 tct tca caa gca tgc acg gtg aac ggt tac tac ata ccg aag aac acg     1264
Ser Ser Gln Ala Cys Thr Val Asn Gly Tyr Tyr Ile Pro Lys Asn Thr
        380                 385                 390 agg ctc aac gtc aac ata tgg gcg atc gga agg gat ccc aat gtg tgg     1312
Arg Leu Asn Val Asn Ile Trp Ala Ile Gly Arg Asp Pro Asn Val Trp
    395                 400                 405 gag aat ccc ctg gaa ttc aac ccc gac agg ttc atg tcc ggt aag aac     1360
Glu Asn Pro Leu Glu Phe Asn Pro Asp Arg Phe Met Ser Gly Lys Asn
410                 415                 420                 425 gca aag ctc gat ccg aga gga aat gat ttt gaa ctc att ccg ttc ggg     1408
Ala Lys Leu Asp Pro Arg Gly Asn Asp Phe Glu Leu Ile Pro Phe Gly
                430                 435                 440 gct ggt cga agg att tgt gcg gga gcg agg atg ggg ata gtt ctt gtg     1456
Ala Gly Arg Arg Ile Cys Ala Gly Ala Arg Met Gly Ile Val Leu Val
            445                 450                 455 gaa tat ata ttg gga agt ttg gtg cat tct ttt gat tgg aaa ttg ccc     1504
Glu Tyr Ile Leu Gly Ser Leu Val His Ser Phe Asp Trp Lys Leu Pro
        460                 465                 470 gaa gga gtg aag gag atg aat ttg gat gag gct ttt ggg ctt gct ttg     1552
Glu Gly Val Lys Glu Met Asn Leu Asp Glu Ala Phe Gly Leu Ala Leu
    475                 480                 485 caa aaa gct gtt cct ctt gca gca atg gtt act ccg agg ttg cct tca     1600
Gln Lys Ala Val Pro Leu Ala Ala Met Val Thr Pro Arg Leu Pro Ser
490                 495                 500                 505 aat tgt tat gct cct taagtaatag tatttaagtg cgtccgaata tcgaagttta    1655
Asn Cys Tyr Ala Pro
                510 tatgattttc ttgtgcttgt ttctatccac tatgttgtaa gaattcatct ccgatcctct  1715 ggtggtcatg gctatatatc gtaattcttt ttctatgtcg tactaatatc aatcaattat  1775 attttcaaac ttttttctaa aaaaaaaaaa aaaaaa                            1811

<210> SEQ ID NO 72
<211> LENGTH: 510
```

<212> TYPE: PRT
<213> ORGANISM: Antirrhinum kellogii

<400> SEQUENCE: 72

| | | | | | | | | | | | | | | |
|---|---|---|---|---|---|---|---|---|---|---|---|---|---|---|
| Met | Gln | Ile | Ile | Ile | Pro | Val | Leu | Leu | Lys | Glu | Leu | Thr | Val | Ala | Ala |
| 1 | | | | 5 | | | | | 10 | | | | | 15 | |
| Leu | Leu | Tyr | Val | Phe | Thr | Asn | Ile | Leu | Ile | Arg | Ser | Leu | Leu | Thr | Arg |
| | | | 20 | | | | | 25 | | | | | 30 | | |
| Pro | Arg | His | Arg | Leu | Pro | Pro | Gly | Pro | Arg | Gly | Phe | Pro | Val | Val | Gly |
| | | 35 | | | | | 40 | | | | | 45 | | | |
| Ala | Leu | Pro | Leu | Leu | Gly | Ser | Met | Pro | His | Val | Ala | Leu | Ala | Lys | Met |
| | 50 | | | | | 55 | | | | | 60 | | | | |
| Ser | Lys | Thr | Tyr | Gly | Pro | Val | Ile | Tyr | Leu | Lys | Val | Gly | Ala | His | Gly |
| 65 | | | | | 70 | | | | 75 | | | | | 80 | |
| Met | Ala | Val | Ala | Ser | Thr | Pro | Glu | Ser | Ala | Lys | Ala | Phe | Leu | Lys | Thr |
| | | | | 85 | | | | | 90 | | | | | 95 | |
| Leu | Asp | Thr | Asn | Phe | Ser | Asn | Arg | Pro | Pro | Asn | Ala | Gly | Ala | Thr | His |
| | | | 100 | | | | | 105 | | | | | 110 | | |
| Leu | Ala | Tyr | Asn | Ser | Gln | Asp | Met | Val | Phe | Ala | Ala | Tyr | Gly | Pro | Arg |
| | | 115 | | | | | 120 | | | | | 125 | | | |
| Trp | Arg | Leu | Leu | Arg | Lys | Leu | Ser | Asn | Leu | His | Met | Leu | Gly | Thr | Lys |
| | 130 | | | | | 135 | | | | | 140 | | | | |
| Ala | Leu | Asp | Asp | Trp | Ala | Asn | Val | Arg | Val | Ser | Glu | Val | Gly | Tyr | Met |
| 145 | | | | | 150 | | | | 155 | | | | | 160 | |
| Leu | Glu | Asp | Met | His | Gly | Ala | Ser | Gly | Arg | Gly | Lys | Val | Val | Gly | Val |
| | | | | 165 | | | | | 170 | | | | | 175 | |
| Pro | Gly | Met | Leu | Val | Tyr | Ala | Met | Ala | Asn | Met | Ile | Gly | Gln | Val | Ile |
| | | | 180 | | | | | 185 | | | | | 190 | | |
| Leu | Ser | Arg | Arg | Val | Phe | Val | Thr | Arg | Glu | Glu | Leu | Asn | Glu | Phe | |
| | | 195 | | | | | 200 | | | | | 205 | | | |
| Lys | Asp | Met | Val | Val | Glu | Leu | Met | Thr | Ser | Ala | Gly | Tyr | Phe | Asn | Ile |
| | 210 | | | | | 215 | | | | | 220 | | | | |
| Gly | Asp | Phe | Ile | Pro | Ser | Phe | Ala | Trp | Met | Asp | Leu | Gln | Gly | Ile | Glu |
| 225 | | | | | 230 | | | | 235 | | | | | 240 | |
| Lys | Gly | Met | Lys | Gly | Leu | His | Lys | Lys | Phe | Asp | Asp | Leu | Ile | Ser | Arg |
| | | | | 245 | | | | | 250 | | | | | 255 | |
| Met | Leu | Lys | Glu | His | Leu | Ala | Ser | Ala | His | Ile | Arg | Lys | Glu | Lys | Pro |
| | | | 260 | | | | | 265 | | | | | 270 | | |
| Asp | Phe | Leu | Asp | Val | Ile | Leu | Ala | Asn | Arg | Asp | Thr | Leu | Glu | Gly | Glu |
| | | 275 | | | | | 280 | | | | | 285 | | | |
| Arg | Leu | Thr | Thr | Ser | Asn | Ile | Lys | Ala | Leu | Leu | Leu | Asn | Leu | Phe | Thr |
| | 290 | | | | | 295 | | | | | 300 | | | | |
| Ala | Gly | Thr | Asp | Thr | Ser | Ser | Ser | Thr | Ile | Glu | Trp | Ala | Leu | Ala | Glu |
| 305 | | | | | 310 | | | | 315 | | | | | 320 | |
| Met | Ile | Lys | Asn | Pro | Ala | Ile | Leu | Lys | Lys | Ala | His | Asp | Glu | Met | Asp |
| | | | | 325 | | | | | 330 | | | | | 335 | |
| Gln | Val | Val | Gly | Trp | Asn | Arg | Arg | Leu | Met | Glu | Ser | Asp | Ile | Pro | Lys |
| | | | 340 | | | | | 345 | | | | | 350 | | |
| Leu | Pro | Tyr | Leu | Gln | Ala | Ile | Cys | Lys | Glu | Ser | Phe | Arg | Lys | His | Pro |
| | | 355 | | | | | 360 | | | | | 365 | | | |
| Ser | Thr | Pro | Leu | Asn | Leu | Pro | Arg | Ile | Ser | Ser | Gln | Ala | Cys | Thr | Val |
| | 370 | | | | | 375 | | | | | 380 | | | | |
| Asn | Gly | Tyr | Tyr | Ile | Pro | Lys | Asn | Thr | Arg | Leu | Asn | Val | Asn | Ile | Trp |
| 385 | | | | | 390 | | | | 395 | | | | | 400 | |

```
Ala Ile Gly Arg Asp Pro Asn Val Trp Glu Asn Pro Leu Glu Phe Asn
            405                 410                 415

Pro Asp Arg Phe Met Ser Gly Lys Asn Ala Lys Leu Asp Pro Arg Gly
            420                 425                 430

Asn Asp Phe Glu Leu Ile Pro Phe Gly Ala Gly Arg Arg Ile Cys Ala
            435                 440                 445

Gly Ala Arg Met Gly Ile Val Leu Val Glu Tyr Ile Leu Gly Ser Leu
        450                 455                 460

Val His Ser Phe Asp Trp Lys Leu Pro Glu Gly Val Lys Glu Met Asn
465                 470                 475                 480

Leu Asp Glu Ala Phe Gly Leu Ala Leu Gln Lys Ala Val Pro Leu Ala
            485                 490                 495

Ala Met Val Thr Pro Arg Leu Pro Ser Asn Cys Tyr Ala Pro
            500                 505                 510

<210> SEQ ID NO 73
<211> LENGTH: 34
<212> TYPE: DNA
<213> ORGANISM: Artificial
<220> FEATURE:
<223> OTHER INFORMATION: ADH-AkF3'5'H-Fd

<400> SEQUENCE: 73
caagaaaaat aaatgcagat aataattccg gtcc                              34

<210> SEQ ID NO 74
<211> LENGTH: 23
<212> TYPE: DNA
<213> ORGANISM: Artificial
<220> FEATURE:
<223> OTHER INFORMATION: NsiI-AkF3'5'H-Rv

<400> SEQUENCE: 74
atgcatgtcc tctaacatgt atc                                          23

<210> SEQ ID NO 75
<211> LENGTH: 35
<212> TYPE: DNA
<213> ORGANISM: Artificial
<220> FEATURE:
<223> OTHER INFORMATION: AkF3'5'H-ADH-Rv

<400> SEQUENCE: 75
tattatctgc atttattttt cttgatttcc ttcac                             35

<210> SEQ ID NO 76
<211> LENGTH: 23
<212> TYPE: DNA
<213> ORGANISM: Artificial
<220> FEATURE:
<223> OTHER INFORMATION: NsiI-AkF3'5'H-Rv

<400> SEQUENCE: 76
atgcatgtcc tctaacatgt atc                                          23

<210> SEQ ID NO 77
<211> LENGTH: 1667
<212> TYPE: DNA
<213> ORGANISM: Cineraria
<220> FEATURE:
<221> NAME/KEY: misc_feature
<223> OTHER INFORMATION: Ci5a18
<220> FEATURE:
```

```
<221> NAME/KEY: CDS
<222> LOCATION: (39)..(1550)

<400> SEQUENCE: 77
gaattactaa ccaattctta cgttgtcaag taaataaa atg agc att cta acc cta         56
                                          Met Ser Ile Leu Thr Leu
                                           1               5 atc tgc acc ttc atc act ggt ttg atg ttc tat ggg ttg gtt aat ttg         104
Ile Cys Thr Phe Ile Thr Gly Leu Met Phe Tyr Gly Leu Val Asn Leu
             10                  15                  20 ctt agc cgt cgc gct agc cgt ctt cct cca ggt cca acc cca tgg cca         152
Leu Ser Arg Arg Ala Ser Arg Leu Pro Pro Gly Pro Thr Pro Trp Pro
         25                  30                  35 atc atc ggc aac cta atg cac ctt ggt aaa ctt cca cat cac tcg ctg         200
Ile Ile Gly Asn Leu Met His Leu Gly Lys Leu Pro His His Ser Leu
 40                  45                  50 gcg gac ttg gcg aaa aag tat ggt ccg ttg ata cat gtc cga cta ggg         248
Ala Asp Leu Ala Lys Lys Tyr Gly Pro Leu Ile His Val Arg Leu Gly
 55                  60                  65                  70 tcc gtt gat gtt gtg gtg gcc tcg tct gcg tcc gtt gct ggg cag ttt         296
Ser Val Asp Val Val Val Ala Ser Ser Ala Ser Val Ala Gly Gln Phe
                 75                  80                  85 tta aag gtg cac gat gcg aat ttt gcc aac agg cca cca aat tct gga         344
Leu Lys Val His Asp Ala Asn Phe Ala Asn Arg Pro Pro Asn Ser Gly
             90                  95                 100 gct aaa cat atg gcg tat aat tat cat gat atg gtg ttt gcg ccg tat         392
Ala Lys His Met Ala Tyr Asn Tyr His Asp Met Val Phe Ala Pro Tyr
         105                 110                 115 ggt cca agg tgg cga atg ctt cga aag atg tgc tcc atg cat ctg ttt         440
Gly Pro Arg Trp Arg Met Leu Arg Lys Met Cys Ser Met His Leu Phe
     120                 125                 130 tct gcc aaa gca ctc act gat ttt cgt caa gtt cga cag gag gag gta         488
Ser Ala Lys Ala Leu Thr Asp Phe Arg Gln Val Arg Gln Glu Glu Val
135                 140                 145                 150 atg ata ctc acg cgc gtt ttg gcc ggg act gaa caa tcg gca gtg aaa         536
Met Ile Leu Thr Arg Val Leu Ala Gly Thr Glu Gln Ser Ala Val Lys
                 155                 160                 165 cta gat caa caa ctt aac gtg tgc ttc gca aac aca tta tcc cga atg         584
Leu Asp Gln Gln Leu Asn Val Cys Phe Ala Asn Thr Leu Ser Arg Met
             170                 175                 180 atg tta gac agg aga gta ttt gga gac ggt gat cca aag gcg gac gac         632
Met Leu Asp Arg Arg Val Phe Gly Asp Gly Asp Pro Lys Ala Asp Asp
         185                 190                 195 tac aag gat atg gtg gtt gag ttg atg act ttg gcc gga caa ttc aac         680
Tyr Lys Asp Met Val Val Glu Leu Met Thr Leu Ala Gly Gln Phe Asn
     200                 205                 210 atc ggt gac tac att cct tgg ctt gac ttg ctt gac cta caa ggc att         728
Ile Gly Asp Tyr Ile Pro Trp Leu Asp Leu Leu Asp Leu Gln Gly Ile
215                 220                 225                 230 gtc aaa agg atg aag aaa gtt cat tct caa ttc gat tcg ttc ctt gac         776
Val Lys Arg Met Lys Lys Val His Ser Gln Phe Asp Ser Phe Leu Asp
                 235                 240                 245 acc atc att gat gaa cat act att ggc acg ggc cgt cat gtt gac atg         824
Thr Ile Ile Asp Glu His Thr Ile Gly Thr Gly Arg His Val Asp Met
             250                 255                 260 tta agc aca atg att tca ctc aaa gat aat gcc gat gga gag gga ggg         872
Leu Ser Thr Met Ile Ser Leu Lys Asp Asn Ala Asp Gly Glu Gly Gly
         265                 270                 275 aag ctt tcg ttc atc gag atc aaa gct ctt cta ctg aac tta ttc tca         920
Lys Leu Ser Phe Ile Glu Ile Lys Ala Leu Leu Leu Asn Leu Phe Ser
```

|   |   |   |   |   |   |   |   |   |   |   |   |   |   |   |   |
|---|---|---|---|---|---|---|---|---|---|---|---|---|---|---|---|
|   |   | 280 |   |   |   | 285 |   |   |   | 290 |   |   |   |   |   |
| gcg | gga | acg | gac | acg | tca | tct | agt | acc | gtg | gaa | tgg | gga | ata | gcg | gaa | 968
| Ala | Gly | Thr | Asp | Thr | Ser | Ser | Ser | Thr | Val | Glu | Trp | Gly | Ile | Ala | Glu |
| 295 |   |   |   |   | 300 |   |   |   |   | 305 |   |   |   |   | 310 |

| ctc | att | cgc | cac | cca | cag | cta | atg | aaa | caa | gcg | caa | gaa | gaa | atg | gac | 1016 |
| Leu | Ile | Arg | His | Pro | Gln | Leu | Met | Lys | Gln | Ala | Gln | Glu | Glu | Met | Asp |
|   |   |   |   | 315 |   |   |   |   | 320 |   |   |   |   | 325 |   |

| att | gta | att | gga | aaa | aac | cgg | ctt | gta | aca | gaa | atg | gac | ata | agc | caa | 1064 |
| Ile | Val | Ile | Gly | Lys | Asn | Arg | Leu | Val | Thr | Glu | Met | Asp | Ile | Ser | Gln |
|   |   |   | 330 |   |   |   |   | 335 |   |   |   |   | 340 |   |   |

| cta | aca | ttc | ctc | caa | gcc | att | gtg | aaa | gaa | acg | ttt | aga | ctc | cac | ccc | 1112 |
| Leu | Thr | Phe | Leu | Gln | Ala | Ile | Val | Lys | Glu | Thr | Phe | Arg | Leu | His | Pro |
|   |   |   |   | 345 |   |   |   |   | 350 |   |   |   |   | 355 |   |

| gcg | acg | cca | ctt | tcc | ctg | cca | agg | att | gca | tcg | gaa | agc | tgt | gag | gtc | 1160 |
| Ala | Thr | Pro | Leu | Ser | Leu | Pro | Arg | Ile | Ala | Ser | Glu | Ser | Cys | Glu | Val |
|   |   | 360 |   |   |   |   | 365 |   |   |   |   | 370 |   |   |   |

| aag | ggg | tat | cat | gtt | cct | aag | gga | tcc | ata | ctc | ttt | gtt | aac | gtg | tgg | 1208 |
| Lys | Gly | Tyr | His | Val | Pro | Lys | Gly | Ser | Ile | Leu | Phe | Val | Asn | Val | Trp |
| 375 |   |   |   |   | 380 |   |   |   |   | 385 |   |   |   |   | 390 |

| gcc | att | gct | cga | caa | tca | gaa | ttg | tgg | acc | gac | cca | ctt | gaa | ttt | cgg | 1256 |
| Ala | Ile | Ala | Arg | Gln | Ser | Glu | Leu | Trp | Thr | Asp | Pro | Leu | Glu | Phe | Arg |
|   |   |   |   | 395 |   |   |   |   | 400 |   |   |   |   | 405 |   |

| cct | ggt | cgt | ttc | cta | atc | cca | gga | gaa | aaa | cct | aat | gtt | gaa | gtg | aag | 1304 |
| Pro | Gly | Arg | Phe | Leu | Ile | Pro | Gly | Glu | Lys | Pro | Asn | Val | Glu | Val | Lys |
|   |   |   | 410 |   |   |   |   | 415 |   |   |   |   | 420 |   |   |

| cca | aat | gat | ttc | gaa | att | gta | cca | ttc | ggg | gga | gga | cga | agg | att | tgt | 1352 |
| Pro | Asn | Asp | Phe | Glu | Ile | Val | Pro | Phe | Gly | Gly | Gly | Arg | Arg | Ile | Cys |
|   |   |   | 425 |   |   |   |   | 430 |   |   |   |   | 435 |   |   |

| gca | ggt | atg | agc | ctc | gga | ttg | aga | atg | gtc | aat | ttg | ctt | att | gca | aca | 1400 |
| Ala | Gly | Met | Ser | Leu | Gly | Leu | Arg | Met | Val | Asn | Leu | Leu | Ile | Ala | Thr |
|   |   | 440 |   |   |   |   | 445 |   |   |   |   | 450 |   |   |   |

| ttg | gtt | caa | gcc | ttt | gat | tgg | gaa | ttg | gct | aat | ggg | tta | gag | cca | gaa | 1448 |
| Leu | Val | Gln | Ala | Phe | Asp | Trp | Glu | Leu | Ala | Asn | Gly | Leu | Glu | Pro | Glu |
| 455 |   |   |   |   | 460 |   |   |   |   | 465 |   |   |   |   | 470 |

| aag | ctt | aac | atg | gaa | gaa | gtg | ttt | ggg | att | agc | ctt | caa | agg | gtt | caa | 1496 |
| Lys | Leu | Asn | Met | Glu | Glu | Val | Phe | Gly | Ile | Ser | Leu | Gln | Arg | Val | Gln |
|   |   |   |   | 475 |   |   |   |   | 480 |   |   |   |   | 485 |   |

| ccc | ttg | ttg | gtg | cac | ccg | agg | cca | agg | tta | gcc | cgt | cac | gta | tac | gga | 1544 |
| Pro | Leu | Leu | Val | His | Pro | Arg | Pro | Arg | Leu | Ala | Arg | His | Val | Tyr | Gly |
|   |   |   | 490 |   |   |   |   | 495 |   |   |   |   | 500 |   |   |

| acg | ggt | taaggaaata | aactgcctgt | ttgtaagata | aatctgtttg | aatttatgta |   | 1600 |
| Thr | Gly | ttaaatagtt atgctaagaa ctattttac aaataaagt atattggttt gaaaaaaaaa 1660 aaaaaaa 1667

<210> SEQ ID NO 78
<211> LENGTH: 504
<212> TYPE: PRT
<213> ORGANISM: Cineraria
<400> SEQUENCE: 78

| Met | Ser | Ile | Leu | Thr | Leu | Ile | Cys | Thr | Phe | Ile | Thr | Gly | Leu | Met | Phe |
|---|---|---|---|---|---|---|---|---|---|---|---|---|---|---|---|
| 1 |   |   |   | 5 |   |   |   |   | 10 |   |   |   |   | 15 |   |

| Tyr | Gly | Leu | Val | Asn | Leu | Leu | Ser | Arg | Arg | Ala | Ser | Arg | Leu | Pro | Pro |
|---|---|---|---|---|---|---|---|---|---|---|---|---|---|---|---|
|   |   |   | 20 |   |   |   |   | 25 |   |   |   |   | 30 |   |   |

| Gly | Pro | Thr | Pro | Trp | Pro | Ile | Ile | Gly | Asn | Leu | Met | His | Leu | Gly | Lys |
|---|---|---|---|---|---|---|---|---|---|---|---|---|---|---|---|
|   |   |   | 35 |   |   |   |   | 40 |   |   |   |   | 45 |   |   |

Leu Pro His His Ser Leu Ala Asp Leu Ala Lys Lys Tyr Gly Pro Leu

```
            50                  55                  60
Ile His Val Arg Leu Gly Ser Val Asp Val Val Ala Ser Ser Ala
 65                      70                  75              80

Ser Val Ala Gly Gln Phe Leu Lys Val His Asp Ala Asn Phe Ala Asn
                     85                  90                  95

Arg Pro Pro Asn Ser Gly Ala Lys His Met Ala Tyr Asn Tyr His Asp
                    100                 105                 110

Met Val Phe Ala Pro Tyr Gly Pro Arg Trp Arg Met Leu Arg Lys Met
                115                 120                 125

Cys Ser Met His Leu Phe Ser Ala Lys Ala Leu Thr Asp Phe Arg Gln
            130                 135                 140

Val Arg Gln Glu Glu Val Met Ile Leu Thr Arg Val Leu Ala Gly Thr
145                 150                 155                 160

Glu Gln Ser Ala Val Lys Leu Asp Gln Gln Leu Asn Val Cys Phe Ala
                165                 170                 175

Asn Thr Leu Ser Arg Met Met Leu Asp Arg Arg Val Phe Gly Asp Gly
                180                 185                 190

Asp Pro Lys Ala Asp Asp Tyr Lys Asp Met Val Val Glu Leu Met Thr
                195                 200                 205

Leu Ala Gly Gln Phe Asn Ile Gly Asp Tyr Ile Pro Trp Leu Asp Leu
210                 215                 220

Leu Asp Leu Gln Gly Ile Val Lys Arg Met Lys Lys Val His Ser Gln
225                 230                 235                 240

Phe Asp Ser Phe Leu Asp Thr Ile Ile Asp Glu His Thr Ile Gly Thr
                245                 250                 255

Gly Arg His Val Asp Met Leu Ser Thr Met Ile Ser Leu Lys Asp Asn
                260                 265                 270

Ala Asp Gly Glu Gly Gly Lys Leu Ser Phe Ile Glu Ile Lys Ala Leu
                275                 280                 285

Leu Leu Asn Leu Phe Ser Ala Gly Thr Asp Thr Ser Ser Ser Thr Val
                290                 295                 300

Glu Trp Gly Ile Ala Glu Leu Ile Arg His Pro Gln Leu Met Lys Gln
305                 310                 315                 320

Ala Gln Glu Glu Met Asp Ile Val Ile Gly Lys Asn Arg Leu Val Thr
                325                 330                 335

Glu Met Asp Ile Ser Gln Leu Thr Phe Leu Gln Ala Ile Val Lys Glu
                340                 345                 350

Thr Phe Arg Leu His Pro Ala Thr Pro Leu Ser Leu Pro Arg Ile Ala
                355                 360                 365

Ser Glu Ser Cys Glu Val Lys Gly Tyr His Val Pro Lys Gly Ser Ile
    370                 375                 380

Leu Phe Val Asn Val Trp Ala Ile Ala Arg Gln Ser Glu Leu Trp Thr
385                 390                 395                 400

Asp Pro Leu Glu Phe Arg Pro Gly Arg Phe Leu Ile Pro Gly Glu Lys
                405                 410                 415

Pro Asn Val Glu Val Lys Pro Asn Asp Phe Glu Ile Val Pro Phe Gly
                420                 425                 430

Gly Gly Arg Arg Ile Cys Ala Gly Met Ser Leu Gly Leu Arg Met Val
                435                 440                 445

Asn Leu Leu Ile Ala Thr Leu Val Gln Ala Phe Asp Trp Glu Leu Ala
                450                 455                 460

Asn Gly Leu Glu Pro Glu Lys Leu Asn Met Glu Glu Val Phe Gly Ile
465                 470                 475                 480
```

Ser Leu Gln Arg Val Gln Pro Leu Leu Val His Pro Arg Pro Arg Leu
            485                 490                 495

Ala Arg His Val Tyr Gly Thr Gly
            500

<210> SEQ ID NO 79
<211> LENGTH: 8552
<212> TYPE: DNA
<213> ORGANISM: Cineraria
<220> FEATURE:
<221> NAME/KEY: misc_feature
<223> OTHER INFORMATION: gCi01-pBluestar

<400> SEQUENCE: 79

| | | | | | |
|---|---|---|---|---|---|
| gcggccgcgg | atcccgggaa | ttctcgatcc | agccatgtgt | ctagtacaac | catacagacg | 60 |
| attaaaaaaa | aaactttaaa | ccacaaaacg | ggttttgcaa | acgaagaaat | tgcctcaaaa | 120 |
| catttccata | tggagtttag | ggacagagtg | cgtttgctac | attaaacaac | tcttttataa | 180 |
| aaaaacatag | cggtacgaga | atgacccact | aaccgttcat | gtccattggc | aaaagttact | 240 |
| attgtgagtc | ttgtatatac | atttaaaaaa | aagaatata | tcagttccat | aaagggcctg | 300 |
| aaacataagt | aagaatatat | caatgacgtt | cggttcggtt | tttggtttat | ataaagagaa | 360 |
| cttgatttga | aaaattacga | gaataacaaa | tatttggggt | gtcatttat | aaaatatcaa | 420 |
| aattttaaaa | ctattttaca | aaatgttaac | aagtaagttg | ttttttttt | tttttcaca | 480 |
| agcagttgaa | acagttttg | ttgaacgtga | agttatagct | ttacttgaag | tttgatattt | 540 |
| tggcatcttg | acactacatg | tctttctagt | gtgacccta | tcttacaact | atcacatgtc | 600 |
| aacggttttg | tctgtccttt | ggatagtata | cggtctttgt | tttaggacgt | ctcgcatgtg | 660 |
| tcctctctat | ggtggtgggt | tgatcgtatg | aatccttagg | atcgtagcca | tttagaagga | 720 |
| tttccgacat | ggaatatcaa | tcatgtatat | gtacgtttat | aattctcggc | gttgaaccaa | 780 |
| tgttgtgtcg | aactcccgac | atcgttcatt | tccaaatgtg | ttaaaactgt | tgtaaggtgt | 840 |
| gaacaaggta | taccatattt | tgccaaaact | tgacaactgc | attttttta | tcatgttgtc | 900 |
| acacacctca | tacattttatc | attaactggt | atgactttcc | atccaaactt | gacaagctct | 960 |
| taaccatttg | gcgacatcta | aactattcga | tagtgactta | attcgtaagt | taatgcacaa | 1020 |
| atgtcgacaa | catattccgc | gagtcgcatc | tggtatggaa | cacaaatgga | tcaagagggc | 1080 |
| taaaacccat | gaggttagaa | aattttactt | ccaagttcaa | gttcatttga | tacaagcact | 1140 |
| gcaaaatcat | tctgcagact | aatctaaatc | ttattcttcc | agagatgata | agttagtttg | 1200 |
| cagctcggtt | tttatgtttt | cttgatacgt | ttatctgtag | atgtgatcga | aatgatagta | 1260 |
| cacgcgctta | tttttttgtag | tcgtatcgca | tatgttagtt | aaaaagtctg | aaactaactt | 1320 |
| aaaaagtttg | tcattttgaa | taggtggtag | ttgaaaatta | ggagtataag | tttacaaggg | 1380 |
| ttggtgttac | ttaacaatct | cctaatcttt | aagtcattct | tttgattttt | cggcataaat | 1440 |
| atatcgatga | caatctcccct | acataaacgc | gattttggtt | aataacctga | ggtagaaata | 1500 |
| tggctggggg | tggagaactt | agtactatca | caacaaaaac | aggcgaacat | gtggttagga | 1560 |
| ggccacgggg | caggccagct | gggtcaaaaa | acaggccgaa | accacccatt | atcattaccc | 1620 |
| gagacagtgc | caatacgttg | cgggctcatg | ccatggaggt | tagcccaggg | tgtgacattg | 1680 |
| ttgagagctt | agccactttt | gctaggagga | acaacaagg | gatttgggtg | ctaagtccg | 1740 |
| ctggatttgt | gagcaatgtt | atgttgcgtc | aacctggccc | atcacaggct | ggtacgggtt | 1800 |
| ccgggcctat | tgtcacactt | catggccggt | ttgagatttt | atctttggtt | ggttctgtat | 1860 |

```
tgccacatcc ggctccgcca ggtgtcactg ggttagccat atatttagtt ggcccgcagg    1920
gccaagtcgt gggtggtgcc attgctggcc cactcatgac atcgggacct gtggtgctca    1980
tggcagccac tttcatgaat gccactttcg ataggttgcc tatcgaaaaa gatgaaatgg    2040
ttgcagccac tactacacac gatcgacatc accattgtgt caatggtgtt tcggatattt    2100
atgggacgac ccaacaaaac atgctttcta acacaaccct ccctcatccc gagatttata    2160
cctggtcaac ggctcgacca ttgtccaagg cataagttat ggaaaagaaa aaataaaaaa    2220
catatagaaa gtaaactttt aaaacttgtg taagcccaaa ttgtattact caagatcggc    2280
aggcgattta cgacctcagt tacgtgttta agcgtttgat atgtaaactt ttacgagcga    2340
aaaatgatca agaaaattta gtcatatgaa gttagaagtc attagattct gtaatgtaat    2400
gtatgtttct ggtatcaaaa gttattatca gtttgtgttt ctaaatcctt aacagaatca    2460
atatgcattc gacttacagt gattaagacg atcatagaag ggattatcgt cacaaaattt    2520
agtcagatac ttatgaactg acaaaatcct ttacagaatc aatatgcatt agacttacag    2580
tgcaaacata tacgccgaga gctaaaagcg acggtgataa gagtagaatc gtaatttcac    2640
agaatcagca gacttcttat aaagaaaaca caactgaaaa tcaagttcac aaactacttc    2700
atttactaat ctttgatgtt caacaagtcg ttggcgaggg catgggtact tcggtaattt    2760
cacacaactc atgaatgttt ttatgaagaa aacacttcca agtataaacc aagttctcaa    2820
actaatatgt tcactaatca atgacgttcg agtaaatcac acctgaatac aatgagccta    2880
gattttacct ggcaattcga attttcaaac cattgaacta atcttttgca ataattctct    2940
tgcaccaaga tcatcgggtg aacgagaggt ccactcctgg taatggcgaa gactaccagt    3000
gaaatctgta aaaagcccgt caaggcgtca actcccattg tgtctatcca gtaattgtat    3060
tccatatatg ggccttcaca gaatttgaaa tgcaagaact ggttttcatt gcgaaatgtg    3120
taagggtgca gctgcaagta ttagtaaaag acgttcggtt tgactttga ggtcaacaca    3180 tagaaaaatt ctactccaat tttactcgaa gtaatgtgat tttcaggaaa gattacaaag    3240
aaactcgtaa catattaaat atgggacaat attagtatta agaacttacc cagattcaaa    3300
tcagtttgaa aatttgaaag ttatatataa agataaaatt tgacctctca aggtcaaaca    3360
gagaaatcca actccgttta tacacaacct taacgaaatt ttaagaaaat atcaacgatt    3420
accaaaacag ttctaacatg ttaacacgtg gaaacgattc gtctcttgag actaagtaaa    3480
ttatatttac attaatgtgt gattctgaaa aaggtcgtc aaaatatcta ttaaatctaa    3540
tgtacctgta gattatgggc gtgagctcgg gttttgagat tgggaggcgt ttgaatgtag    3600
ttatctttca caggaacaac agtgtctttc catggaccaa taccgacaac atattctttg    3660
atatatttga agtaacgatc tgaagtgatt tctgcatacg tctgcaaatg aaaagaaat    3720 cagattataa acatccattg caaactatcc ttgcatcgtg tttggatgtt cgttttaagc    3780
gagtatttta tggaatagggg agaatcagac aattagttgt aataaaacat gatctttaat    3840
tgtgctacta gtttaagtta taatgataat agaaaacatt tagtcttcgg aaaattatat    3900
aaattaccaa aaatgggttt aactgtttca aaccaaaagt ggcaagatgt caggtcggat    3960
ggattgggta acgggtcaaa atgggttgga ctgaaacatg ttcaaacata gcgcgtaggc    4020
cgtagagatt acaaaaattc tccgttccaa ataaggttaa cagatatgac tatgctgact    4080
ttttaagtgt caaatgcgat tctcttttcc ggtatgcata aaaaactgac gacggacatt    4140
acactatata aaaatttaga aggttataat aaaccaagaa aatataattg tattaaattg    4200
```

```
tgtgagttat atgaattaca tagaaccttt tatatatggt tgaattacct tgctgaacaa    4260
gaaacctaaa cctattagaa atgtctcaaa aatcctaagc ttcaggaata ccttcccggc    4320
cttagcgacg aggaagatat gctagagtgt atgtgtgact cgttaaaatc atgaactaga    4380
acaaagggaa aggaacaatg ttacaatctc aatgattaga taggatataa ctcgataaca    4440 aacctaaccca gcagagttag atcaagtggt aagtctttgc ctttgaagac ataggtcgag    4500
ggttcgatcc tcactccatg tggtcggagg tttattggtg aatgcatgct tagctaccgt    4560
tcaaagtaac tttattggtg aatgcatgct tagctaccgt tcaaaatctt caaaaagggt    4620
aattatgtct aatatgccat ctaagttcta accaacccct caaatgttca ttcctataat    4680
tactaaccaa ttcttacgtt gtcaagtaaa taaaatgagc attctaaccc taatctgcac    4740
cttcatcact ggtttgatgt tctatgggtt ggttaatttg cttagccgtc gcgctagccg    4800
tcttcctcca ggtccaaccc catggccaat catcggcaac ctaatgcacc ttggtaaact    4860
tccacatcac tcgctggcgg acttggcgaa aaagtatggt ccgttgatac atgtccgact    4920
agggtccgtt gatgttgtgg tggcctcgtc tgcgtccgtt gctgggcagt ttttaaaggt    4980
gcatgatgcg aatttttgcca acaggccacc aaattctgga gctaaacata tggcgtataa    5040
ttatcatgat atggtgtttg cgccgtatgg tccaaggtgg cgaatgcttc gaaagatgtg    5100
ctccatgcat ctgttttctg ccaaagcact cactgatttt cgtcaagttc gacaggtttt    5160
gtactttcac tttcgtcata tatatagga gattagtacg agaacgaaca cttttaaaat    5220 cacttttaa taatcaaaat atcttttttt ttttaaacaa aatcatggaa tcttattcaa    5280
ataacttttc taaccttcta aattttttt aattttttaa ttttttttt acttacagtg    5340 attaagataa tcacataaaa tatatagata atcacatgaa atttttgtg attatttagt    5400 tcaaatacat tattatcgat atattttttg tgattatctt aaccaccgta aaaaaaattc    5460
aaaaataaaa taaaatctga gaaggttaaa aaagttatat aaataagatt ttccgatttt    5520
gttttcaaca ataaaataaa atttcagaac gtaataaaaa ttgatttttt gttaacgaga    5580
gtttgtaaca atagacggtc aacggaaaat gtgtattatc tggtggtatc accatcggat    5640
tatgccaagc atgcataaaa aaacaaaatc gtaactacag gaggaggtaa cgatactcac    5700
gcgcgttttg gccaggactg gacaatcggc agtgaaacta gatcaacaac ttaacgtgtg    5760
cttcgcaaac acattatccc gaatgatgtt agacaggaga gtatttggag acggtgatcc    5820
aaaggcggac gactacaagg atatggtggt tgagttgatg actttggccg gacaattcaa    5880
catcggtgac tacattcctt ggcttgactt gcttgaccta caaggcattg tcaaaaggat    5940
gaagaaagtt cattctcaat tcgattcgtt ccttgacacc atcattgatg aacatactat    6000
tggcacgggc cgtcatgttg acatgttaag cacaatgatt tcactcaaag ataatgccga    6060
tggagaggga gggaagcttt cgttcatcga gatcaaagct cttctactgg tgcgcgtaat    6120
acatagtagt caacttttt ttttttctgg taatgactct ttgagcaggt aaaatgtccc    6180
caacaggaat caaacttggt acctatcatt tttgggaaaa attttaaaag tactagcttt    6240
ttcaaaaaga ttatgaaaag tatctgtttt tctggacgat tgttaaatct accccaaacg    6300
catgtcttat atgcgttccc ttaatcaaac gttgagggtg cgcatatggt acatgcatac    6360
cctccaaagg agttcccatg cacgttgagg gtgcacatat acacatgcgc accctcttcg    6420
tggtttgcca ccaaggcaaa tcctggagga cagtcaacct ttttgatata agttcagatc    6480
taactctagg ctaatactgt tgatgtttca gaacttgttc tcagcgggaa cggacacgtc    6540
atctagtacc gtggaatggg gaatagcgga actcattcgc cacccacagc taatgaaaca    6600
```

```
agcgcaagaa gaaatggaca ttgtagttgg aaaaaaccgg cttgtaacag aaatggacat    6660
aagccaacta acattccttc aagccattgt gaaagaaacg tttaggctac accccgcgac    6720
gccactttcc ctgccaagga ttgcatcaga aagctgtgag gtcaaggggt atcatgttcc    6780
taagggatcg atactctttg ttaacgtgtg ggccattgct cgacaatcag aattgtggac    6840
cgacccactt gaatttcggc ctggtcgttt cctaatccca ggagaaaaac ctaatgttga    6900
agtgaagcca aatgatttcg aaattgtacc attcggggga ggacgaagga tttgtgcagg    6960
tatgagcctc ggattgagaa tggtcaattt gcttattgca acattggttc aagcctttga    7020
ttgggaattg gctaatgggt tagagccaga aaagcttaac atggaagaag tgtttgggat    7080
tagccttcaa agggttcaac ccttgttggt gcacccgagg ccaaggttag cccgtcacgt    7140
atacggaacg ggttaaggaa ataaactgtc tgtttgtaag atgaatctgt ttgaatttat    7200
gtattaaata gttatgctaa gaactatttt tacaaataaa agtatattgg tttgattgtt    7260
ctcgcttagc ctttgctaaa tcttagatag atgagttgta taacacatca tcattaactc    7320
acatcacgtg gtaacgattt gttttgagt taaaattttt aagaaagga agaaagaga     7380 aagtaaatat aaaaaattt gtgttcccga gaagtttttt acgaaggaag aggggagaaa    7440
gagagagaat tttagagaaa ttttgagtat tttacaacaa aaatcatcct ctcattttg     7500 ggatgatttg gaggatcttt tttctttctt ttccttcgtc cacttcacct cccttttcttt   7560 ccaaaaaaat ctcggaaaca tagcgtaatg ataaacaaaa accaataaaa atgagcagga    7620
gcaaacccta gaaggacgaa atcttgaaaa tttattctaa gatttttaaa aaaaacttgg    7680
cagttggaaa gggcggcgga tatcagtagg tagttgtgtc acaacgacca gggcggtgtg    7740
tcaagaaacc ttgttttgag ttgtgtctat atttaaggct ccaaaatctc cctcgacttc    7800
aaagtgtaca tagaactgcg ttcaaagtga ccgtaggact gcttgtgagt aggagataac    7860
tacaaaatta aacttagtta ggaattagta tgtccgacca aaagattgtg atggtttaga    7920
attaagagac aattacatat attttcaatt aaaactctat aataaaatat ttttcaatca    7980
aattttaaaa taatatatat atatttattt taaaagtata taataatata tttatccaat    8040 caaatttta aataacatat atatatatat tttaaaattt taaattatat atttatccat    8100
ttctatcaat tataataaaa aaataactat tatacctttt ttgataaaac aaaataaaca    8160
tatttaacaa attttattat ataaacttca ataaaatata aatatatga aataaacaga     8220 aatcgtgtta tcgcttactt gaatcaaata ataagttgca gaagataaaa aaaaaattag    8280
actttgaaaa ataaaataaa aaataatata tggttataaa tactataatt tatcaaaaat    8340
actatatttt atcaaaatcc aaaacaaata gttttttttgt tatgaaaaaa aaaatctcta   8400
cacaaacaca ttaaaatttt ataatttaat ttcaaatctc aattaattat ttgagaagat    8460
tcgttcaata tatttgttaa taaagtggac aataagaatt tatttgcttc aaataaacga    8520
caacatgatt tttgttaatt tcatatattt tg                                 8552
```

<210> SEQ ID NO 80
<211> LENGTH: 5638
<212> TYPE: DNA
<213> ORGANISM: Cineraria
<220> FEATURE:
<221> NAME/KEY: misc_feature
<223> OTHER INFORMATION: PvuI-EcoRV fragment from gCi01-pBluestar
<220> FEATURE:
<221> NAME/KEY: exon
<222> LOCATION: (2652)..(3092)
<220> FEATURE:

<221> NAME/KEY: exon
<222> LOCATION: (3618)..(4046)
<220> FEATURE:
<221> NAME/KEY: exon
<222> LOCATION: (4449)..(5090)

<400> SEQUENCE: 80

```
cgacatcacc attgtgtcaa tggtgtttcg gatatttatg ggacgaccca acaaaacatg      60
ctttctaaca caaccctccc tcatcccgag atttataccr ggtcaacggc tcgaccattg     120
tccaaggcat aagttatgga aaagaaaaaa taaaaaacat atagaaagta aacttttaaa     180
acttgtgtaa gcccaaattg tattactcaa gatcggcagg cgatttacga cctcagttac     240
gtgtttaagc gtttgatatg taaactttta cgagcgaaaa atgatcaaga aaatttagtc     300
atatgaagtt agaagtcatt agattctgta atgtaatgta tgtttctggt atcaaaagtt     360
attatcagtt tgtgtttcta aatccttaac agaatcaata tgcattcgac ttacagtgat     420
taagacgatc atagaaggga ttatcgtcac aaaatttagt cagatactta tgaactgaca     480
aaatccttta cagaatcaat atgcattaga cttacagtgc aaacatatac gccgagagct     540
aaaagcgacg gtgataagag tagaatcgta atttcacaga atcagcagac ttcttataaa     600
gaaaacacaa ctagaaaatca agttcacaaa ctacttcatt tactaatctt tgatgttcaa     660
caagtcgttg gcgagggcat gggtacttcg gtaatttcac acaactcatg aatgttttta     720
tgaagaaaac acttccaagt ataaaccaag ttctcaaact aatatgttca ctaatcaatg     780
acgttcgagt aaatcacacc tgaatacaat gagcctagat tttacctggc aattcgaatt     840
ttcaaaccat tgaactaatc ttttgcaata attctcttgc accaagatca tcgggtgaac     900
gagaggtcca ctcctggtaa tggcgaagac taccagtgaa atctgtaaaa agcccgtcaa     960
ggcgtcaact cccattgtgt ctatccagta attgtattcc atatatgggc cttcacagaa    1020
tttgaaatgc aagaactggt tttcattgcg aaatgtgtaa gggtgcagct gcaagtatta    1080
gtaaagacg ttcggtttga cttttgaggt caacacatag aaaaattcta ctccaatttt    1140
actcgaagta atgtgatttt caggaaagat tacaagaaa ctcgtaacat attaaatatg    1200
ggacaatatt agtattaaga acttacccag attcaaatca gtttgaaaat ttgaaagtta    1260
tatataaaga taaaatttga cctctcaagg tcaaacagag aaatccaact ccgtttatac    1320
acaaccttaa cgaaatttta agaaaatatc aacgattacc aaaacagttc taacatgtta    1380
acacgtggaa acgattcgtc tcttgagact aagtaaatta tatttacatt aatgtgtgat    1440
tctgaaaaaa ggtcgtcaaa atatctatta aatctaatgt acctgtagat tatgggcgtg    1500
agctcgggtt ttgagattgg gaggcgtttg aatgtagtta tctttcacag gaacaacagt    1560
gtctttccat ggaccaatac cgacaacata ttctttgata tatttgaagt aacgatctga    1620
agtgatttct gcatacgtct gcaaatgaaa aagaaatcag attataaaca tccattgcaa    1680
actatccttg catcgtgttt ggatgttcgt tttaagcgag tatttttatgg aatagggaga    1740
atcagacaat tagttgtaat aaaacatgat ctttaattgt gctactagtt taagttataa    1800
tgataataga aaacatttag tcttcggaaa attatataaa ttaccaaaaa tgggtttaac    1860
tgtttcaaac caaagtggc aagatgtcag gtcggatgga ttgggtaacg ggtcaaaatg    1920
ggttggactg aaacatgttc aaacatagcg cgtaggccgt agagattaca aaaattctcc    1980
gttccaaata aggttaacag atatgactat gctgactttt taagtgtcaa atgcgattct    2040
cttttccggt atgcataaaa aactgacgac ggacattaca ctatataaaa atttagaagg    2100
ttataataaa ccaagaaaat ataattgtat taaattgtgt gagttatatg aattacatag    2160
```

```
aaccttttat atatggttga attaccttgc tgaacaagaa acctaaacct attagaaatg    2220
tctcaaaaat cctaagcttc aggaatacct tcccggcctt agcgacgagg aagatatgct    2280
agagtgtatg tgtgactcgt taaaatcatg aactagaaca aagggaaagg aacaatgtta    2340
caatctcaat gattagatag gatataactc gataacaaac ctaaccagca gagttagatc    2400
aagtggtaag tctttgcctt tgaagacata ggtcgagggt tcgatcctca ctccatgtgg    2460
tcggaggttt attggtgaat gcatgcttag ctaccgttca aagtaacttt attggtgaat    2520
gcatgcttag ctaccgttca aaatcttcaa aaagggtaat tatgtctaat atgccatcta    2580
agttctaacc aacccttcaa atgttcattc ctataattac taaccaattc ttacgttgtc    2640
aagtaaataa a atg agc att cta acc cta atc tgc acc ttc atc act ggt    2690
              Met Ser Ile Leu Thr Leu Ile Cys Thr Phe Ile Thr Gly
                1               5                  10 ttg atg ttc tat ggg ttg gtt aat ttg ctt agc cgt cgc gct agc cgt    2738
Leu Met Phe Tyr Gly Leu Val Asn Leu Leu Ser Arg Arg Ala Ser Arg
     15                 20                  25 ctt cct cca ggt cca acc cca tgg cca atc atc ggc aac cta atg cac    2786
Leu Pro Pro Gly Pro Thr Pro Trp Pro Ile Ile Gly Asn Leu Met His
30                  35                  40                  45 ctt ggt aaa ctt cca cat cac tcg ctg gcg gac ttg gcg aaa aag tat    2834
Leu Gly Lys Leu Pro His His Ser Leu Ala Asp Leu Ala Lys Lys Tyr
                 50                  55                  60 ggt ccg ttg ata cat gtc cga cta ggg tcc gtt gat gtt gtg gtg gcc    2882
Gly Pro Leu Ile His Val Arg Leu Gly Ser Val Asp Val Val Val Ala
             65                  70                  75 tcg tct gcg tcc gtt gct ggg cag ttt tta aag gtg cat gat gcg aat    2930
Ser Ser Ala Ser Val Ala Gly Gln Phe Leu Lys Val His Asp Ala Asn
         80                  85                  90 ttt gcc aac agg cca cca aat tct gga gct aaa cat atg gcg tat aat    2978
Phe Ala Asn Arg Pro Pro Asn Ser Gly Ala Lys His Met Ala Tyr Asn
     95                 100                 105 tat cat gat atg gtg ttt gcg ccg tat ggt cca agg tgg cga atg ctt    3026
Tyr His Asp Met Val Phe Ala Pro Tyr Gly Pro Arg Trp Arg Met Leu
110                 115                 120                 125 cga aag atg tgc tcc atg cat ctg ttt tct gcc aaa gca ctc act gat    3074
Arg Lys Met Cys Ser Met His Leu Phe Ser Ala Lys Ala Leu Thr Asp
                130                 135                 140 ttt cgt caa gtt cga cag gttttgtact ttcactttcg tcatatatat            3122
Phe Arg Gln Val Arg Gln
                145 agggagatta gtacgagaac gaacactttt aaaatcactt tttaataatc aaaatatctt    3182 tttttttta aacaaaatca tggaatctta ttcaaataac ttttctaacc ttctaaattt     3242 tttttaattt tttaattttt tttttactta cagtgattaa gataatcaca taaaatatat    3302 agataatcac atgaaatttt ttgtgattat ttagttcaaa tacattatta tcgatatatt    3362 ttttgtgatt atcttaacca ccgtaaaaaa aattcaaaaa taaataaaa tctgagaagg     3422 ttaaaaaagt tatataaata agattttccg attttgtttt caacaataaa ataaaatttc    3482 agaacgtaat aaaaattgat tttttgttaa cgagagtttg taacaataga cggtcaacgg    3542 aaaatgtgta ttatctggtg gtatcaccat cggattatgc caagcatgca taaaaaaaca    3602 aaatcgtaac tacag gag gag gta acg ata ctc acg cgc gtt ttg gcc agg    3653
                  Glu Glu Val Thr Ile Leu Thr Arg Val Leu Ala Arg
                                    150                 155 act gga caa tcg gca gtg aaa cta gat caa caa ctt aac gtg tgc ttc    3701
Thr Gly Gln Ser Ala Val Lys Leu Asp Gln Gln Leu Asn Val Cys Phe
```

| | | |
|---|---|---|
| gca aac aca tta tcc cga atg atg tta gac agg aga gta ttt gga gac<br>Ala Asn Thr Leu Ser Arg Met Met Leu Asp Arg Arg Val Phe Gly Asp<br>180                185                190 | | 3749 |
| ggt gat cca aag gcg gac gac tac aag gat atg gtg gtt gag ttg atg<br>Gly Asp Pro Lys Ala Asp Asp Tyr Lys Asp Met Val Val Glu Leu Met<br>        195                200              205 | | 3797 |
| act ttg gcc gga caa ttc aac atc ggt gac tac att cct tgg ctt gac<br>Thr Leu Ala Gly Gln Phe Asn Ile Gly Asp Tyr Ile Pro Trp Leu Asp<br>210                215                220 | | 3845 |
| ttg ctt gac cta caa ggc att gtc aaa agg atg aag aaa gtt cat tct<br>Leu Leu Asp Leu Gln Gly Ile Val Lys Arg Met Lys Lys Val His Ser<br>    225                230              235 | | 3893 |
| caa ttc gat tcg ttc ctt gac acc atc att gat gaa cat act att ggc<br>Gln Phe Asp Ser Phe Leu Asp Thr Ile Ile Asp Glu His Thr Ile Gly<br>240                245                250              255 | | 3941 |
| acg ggc cgt cat gtt gac atg tta agc aca atg att tca ctc aaa gat<br>Thr Gly Arg His Val Asp Met Leu Ser Thr Met Ile Ser Leu Lys Asp<br>                260              265              270 | | 3989 |
| aat gcc gat gga gag gga ggg aag ctt tcg ttc atc gag atc aaa gct<br>Asn Ala Asp Gly Glu Gly Gly Lys Leu Ser Phe Ile Glu Ile Lys Ala<br>275                280                285 | | 4037 |
| ctt cta ctg gtgcgcgtaa tacatagtag tcaactttttt ttttttctg<br>Leu Leu Leu<br>        290 | | 4086 |
| gtaatgactc tttgagcagg taaaatgtcc ccaacaggaa tcaaacttgg tacctatcat | | 4146 |
| ttttgggaaa aattttaaaa gtactagctt tttcaaaaag attatgaaaa gtatctgttt | | 4206 |
| ttctggacga ttgttaaatc taccccaaac gcatgtctta tatgcgttcc cttaatcaaa | | 4266 |
| cgttgagggt gcgcatatgg tacatgcata ccctccaaag gagttcccat gcacgttgag | | 4326 |
| ggtgcacata tacacatgcg caccctcttc gtggtttgcc accaaggcaa atcctggagg | | 4386 |
| acagtcaacc tttttgatat aagttcgat ctaactctag gctaatactg ttgatgtttc | | 4446 |
| ag aac ttg ttc tca gcg gga acg gac acg tca tct agt acc gtg gaa<br>   Asn Leu Phe Ser Ala Gly Thr Asp Thr Ser Ser Ser Thr Val Glu<br>                      295                300              305 | | 4493 |
| tgg gga ata gcg gaa ctc att cgc cac cca cag cta atg aaa caa gcg<br>Trp Gly Ile Ala Glu Leu Ile Arg His Pro Gln Leu Met Lys Gln Ala<br>                310                315              320 | | 4541 |
| caa gaa gaa atg gac att gta gtt gga aaa aac cgg ctt gta aca gaa<br>Gln Glu Glu Met Asp Ile Val Val Gly Lys Asn Arg Leu Val Thr Glu<br>        325                330              335 | | 4589 |
| atg gac ata agc caa cta aca ttc ctt caa gcc att gtg aaa gaa acg<br>Met Asp Ile Ser Gln Leu Thr Phe Leu Gln Ala Ile Val Lys Glu Thr<br>                340                345              350 | | 4637 |
| ttt agg cta cac ccc gcg acg cca ctt tcc ctg cca agg att gca tca<br>Phe Arg Leu His Pro Ala Thr Pro Leu Ser Leu Pro Arg Ile Ala Ser<br>355                360                365 | | 4685 |
| gaa agc tgt gag gtc aag ggg tat cat gtt cct aag gga tcg ata ctc<br>Glu Ser Cys Glu Val Lys Gly Tyr His Val Pro Lys Gly Ser Ile Leu<br>370                375                380              385 | | 4733 |
| ttt gtt aac gtg tgg gcc att gct cga caa tca gaa ttg tgg acc gac<br>Phe Val Asn Val Trp Ala Ile Ala Arg Gln Ser Glu Leu Trp Thr Asp<br>                390                395              400 | | 4781 |
| cca ctt gaa ttt cgg cct ggt cgt ttc cta atc cca gga gaa aaa cct<br>Pro Leu Glu Phe Arg Pro Gly Arg Phe Leu Ile Pro Gly Glu Lys Pro<br>        405                410              415 | | 4829 |
| aat gtt gaa gtg aag cca aat gat ttc gaa att gta cca ttc ggg gga | | 4877 |

```
                Asn Val Glu Val Lys Pro Asn Asp Phe Glu Ile Val Pro Phe Gly Gly
                    420                 425                 430 gga cga agg att tgt gca ggt atg agc ctc gga ttg aga atg gtc aat        4925
Gly Arg Arg Ile Cys Ala Gly Met Ser Leu Gly Leu Arg Met Val Asn
    435                 440                 445 ttg ctt att gca aca ttg gtt caa gcc ttt gat tgg gaa ttg gct aat        4973
Leu Leu Ile Ala Thr Leu Val Gln Ala Phe Asp Trp Glu Leu Ala Asn
450                 455                 460                 465 ggg tta gag cca gaa aag ctt aac atg gaa gaa gtg ttt ggg att agc        5021
Gly Leu Glu Pro Glu Lys Leu Asn Met Glu Glu Val Phe Gly Ile Ser
                470                 475                 480 ctt caa agg gtt caa ccc ttg ttg gtg cac ccg agg cca agg tta gcc        5069
Leu Gln Arg Val Gln Pro Leu Leu Val His Pro Arg Pro Arg Leu Ala
            485                 490                 495 cgt cac gta tac gga acg ggt taaggaaata aactgtctgt tgtaagatg            5120
Arg His Val Tyr Gly Thr Gly
            500 aatctgtttg aatttatgta ttaaatagtt atgctaagaa ctattttac aaataaaagt       5180 atattggttt gattgttctc gcttagcctt tgctaaatct tagatagatg agttgtataa      5240 cacatcatca ttaactcaca tcacgtggta acgatttgtt tttgagttaa aattttaaa       5300 gaaaggaaag aaagagaaag taaatataaa aaaatttgtg ttcccgagaa gttttttacg      5360 aaggaagagg ggagaaagag agagaatttt agagaaattt tgagtatttt acaacaaaaa     5420 tcatcctctc attttggga tgatttggag gatcttttt ctttcttttc cttcgtccac       5480 ttcacctccc tttctttcca aaaaaatctc ggaaacatag cgtaatgata aacaaaaacc     5540 aataaaaatg agcaggagca aaccctagaa ggacgaaatc ttgaaaattt attctaagat     5600 ttttaaaaaa aacttggcag ttggaaaggg cggcggat                             5638

<210> SEQ ID NO 81
<211> LENGTH: 20
<212> TYPE: DNA
<213> ORGANISM: Artificial
<220> FEATURE:
<223> OTHER INFORMATION: forward primer Ci5a18F1

<400> SEQUENCE: 81 catctgttt ctgccaaagc                                                   20

<210> SEQ ID NO 82
<211> LENGTH: 19
<212> TYPE: DNA
<213> ORGANISM: Artificial
<220> FEATURE:
<223> OTHER INFORMATION: reverse primer Ci5a18R1

<400> SEQUENCE: 82
ggattaggaa acgaccagg                                                   19

<210> SEQ ID NO 83
<211> LENGTH: 53
<212> TYPE: DNA
<213> ORGANISM: Artificial
<220> FEATURE:
<223> OTHER INFORMATION: Primer HANS-F3Hpro500-Fd

<400> SEQUENCE: 83
ccaagcttgg cgcgccgcgg ccgcatttaa attactgttc gaacctacaa agg             53
```

```
<210> SEQ ID NO 84
<211> LENGTH: 39
<212> TYPE: DNA
<213> ORGANISM: Artificial
<220> FEATURE:
<223> OTHER INFORMATION: Primer MX-F3Hpro-Rv

<400> SEQUENCE: 84
tttctagaac gcgtttttta tttttcttc acacacttg                    39

<210> SEQ ID NO 85
<211> LENGTH: 53
<212> TYPE: DNA
<213> ORGANISM: Artificial
<220> FEATURE:
<223> OTHER INFORMATION: Primer HAPS-RhCHSpro3k-Fd

<400> SEQUENCE: 85
ccaagcttgg cgcgccttaa ttaaatttaa atcagcaaga gttgaagaaa tag     53

<210> SEQ ID NO 86
<211> LENGTH: 33
<212> TYPE: DNA
<213> ORGANISM: Artificial
<220> FEATURE:
<223> OTHER INFORMATION: Primer NS-RhCHSpro3k-Rv

<400> SEQUENCE: 86
aaagctagca ctagtcatct cggagaaggg tcg                         33

<210> SEQ ID NO 87
<211> LENGTH: 531
<212> TYPE: DNA
<213> ORGANISM: Chrysanthemum
<220> FEATURE:
<221> NAME/KEY: misc_feature
<223> OTHER INFORMATION: CmF3Hpro500
<220> FEATURE:
<221> NAME/KEY: primer_bind
<222> LOCATION: (1)..(21)
<220> FEATURE:
<221> NAME/KEY: primer_bind
<222> LOCATION: (507)..(531)

<400> SEQUENCE: 87
tactgttcga acctacaaag gaatatcaat acgagggctc aattattgtc tcggattcaa    60
tgaattcaca aggtaaataa acgcggtact cttttcattg gtccttcgtt ttatttgttt   120
gacaattaat tgggatggct ggcgtgtata attctcaata catgtctgat ttaatatgtg   180
attggttgac attcatgtga aattaatata ctcattttat gattacaaag acccacgatg   240
tataattaat tccaatcttg tggaatggga tccattgtga accggtgcat gattgttacg   300
gtggggatta cttttgattg gttcagcatt atcatataac ccccgttcaa cggatgcatg   360
ctacattggt acgtatacat atacgattca cgtgtggtag ttgataacta gcgcgatacg   420
cccccacccc atatttcttc aattttctct acaaatacccc atgccaacct tacgaaacac   480
tcattcccct ctactcatag acgcaccaag tgtgtgaaga aaaataaaa a              531
```

METHOD FOR PRODUCTION OF CHRYSANTHEMUM PLANT HAVING DELPHINIDIN-CONTAINING PETALS

CROSS REFERENCE TO RELATED APPLICATIONS

This application is the National Stage of International Application No. PCT/JP2010/053904 filed Mar. 9, 2010, and claims benefit of Japanese Patent Application No. 2009-107054 filed Apr. 24, 2009, which are herein incorporated by reference in their entirety.

REFERENCE TO A SEQUENCE LISTING

A Sequence Listing containing SEQ ID NOS: 1-87 is incorporated herein by reference.

TECHNICAL FIELD

The present invention relates to a method for producing a chrysanthemum plant containing delphinidin in the petals thereof by using the transcriptional regulatory region of chrysanthemum-derived flavanone 3-hydroxylase (F3H) gene, a nucleic acid of that regulatory region, an expression vector or expression cassette containing that nucleic acid, and a chrysanthemum plant, progeny or vegetative proliferation product thereof, or a part or tissue thereof, and particularly a petal or cut flower thereof, in which that regulatory region has been introduced.

BACKGROUND ART

The use of genetic transformation technology makes it possible to impart new traits to plants by expressing a useful gene in a target plant. A wide range of genetically modified plants produced in this manner have already been cultivated. Since regulation of gene expression is mainly controlled at the level of transcription, transcriptional regulation is the most important in terms of regulating the expression of genes. Namely, expressing a gene at a suitable time, in a suitable tissue and at a suitable strength is important for producing an industrially useful genetically modified plant. In many cases, transcription is control by a DNA sequence on the 5' untranslated region of a open reading frame. A region of DNA that determines the starting site of gene transcription and directly regulates the frequency thereof is referred to as a promoter. A promoter is located in a start codon consisting of several tens of base pairs (bp) on the 5'-untranslated region, and frequently contains a TATA box and the like. A cis element that binds various transcriptional regulatory factors is also present on the 5'-untranslated region, and the presence thereof serves to control the timing of transcription, the tissue in which transcription takes place and transcriptional strength. Transcriptional regulatory factors are classified into many families according to their amino acid sequence. For example, examples of well-known families of transcriptional regulatory factors include Myb transcriptional regulatory factor and bHLH (basic helix loop helix) regulatory factor. In actuality, the terms transcriptional regulatory factor and promoter are frequently used with the same meaning.

Anthocyanins, which compose the main components of flower color, are a member of secondary metabolites generically referred to as flavonoids. The color of anthocyanins is dependent on their color. Namely, the color becomes blue as the number of hydroxyl groups of the B ring of anthocyanidins, which is the chromophore of anthocyanins, increases. In addition, as the number of aromatic acyl groups (such as coumaroyl groups or caffeolyl groups) that modify the anthocyanin increases (namely, the wavelength of maximum absorbance shifts to a longer wavelength), the color of the anthocyanin becomes blue and the stability of the anthocyanin is known to increase (see Non-Patent Document 1).

Considerable research has been conducted on those enzymes and genes that encode those enzymes involved in the biosynthesis of anthocyanins (see, Non-Patent Document 1). For example, an enzyme gene that catalyzes a reaction by which an aromatic acyl group is transferred to anthocyanin is obtained from Japanese gentian, lavender and petunias (see Patent Document 1 and Patent Document 2). An enzyme gene involved in the synthesis of anthocyanin that accumulates in the leaves of red perilla (malonylshisonin, 3-O-(6-O-(E)-p-coumaroyl-β-D-glucopyranosyl)-5-O-(6-O-malonyl-β-D-glucopyranosyl)-cyanidin) (see Non-Patent Document 2) has previously been reported in hydroxycinnamoyl CoA: anthocyanin-3-glucoside-aromatic acyl group transferase (3AT) gene (or more simply referred to as "shiso (perilla) anthocyanin-3-acyltransferase (3AT) gene") (see Patent Document 1). Moreover, findings have also been obtained regarding the transcriptional regulation (control) of biosynthase genes of anthocyanins. Cis element sequences bound by Myb transcriptional regulatory factor and bHLH transcriptional regulatory factor are present in the transcriptional regulatory region located on the 5'-region of the start codons of these genes. Myb transcriptional regulatory factor and bHLH transcriptional regulatory factor are known to control synthesis of anthocyanins in petunias, corn and perilla (see Non-Patent Document 1).

Promoters (also referred to as transcriptional regulatory regions) responsible for gene transcription in plants consist of so-called constitutive promoters, which function in any tissue and at any time such as in the developmental stage, organ/tissue-specific promoters, which only function in specific organs and tissues, and time-specific promoters, which only express at a specific time of the developmental stage. Constitutive promoters are frequently used as promoters for expressing useful genes in genetically modified plants. Typical examples of constitutive promoters include cauliflower mosaic virus 35S promoter (also abbreviated as CaMV35S promoter) and promoters construction on the basis thereof (see Non-Patent Document 3), and Mac1 promoter (see Non-Patent Document 4). In plants, however, many genes are only expressed in specific tissues or organs or are expressed time-specifically. This suggests that tissue/organ-specific or time-specific expression of genes is necessary for plants. There are examples of genetic recombination of plants that utilize such tissue/organ-specific or time-specific transcriptional regulatory regions. For example, there are examples of protein being accumulated in seeds by using a seed-specific transcriptional regulatory region.

However, although plants produce flowers of various colors, there are few species capable of producing flowers of all colors due to genetic restrictions on that species. For example, there are no varieties of rose or carnation in nature that are capable of producing blue or purple flowers. This is because roses and carnations lack the flavonoid 3',5'-hydroxylase gene required to synthesize the anthocyanidin, delphinidin, which is synthesized by many species that produce blue and purple flowers. By transformation with the flavonoid 3',5'-hydroxylase gene of petunia or pansy, for example, which are specifies capable of producing blue and purple flowers, into these species, these species can be made to produce blue flowers. In the case of carnations, the transcriptional regulatory region of chalcone synthase gene derived from common snapdragon or petunia is used to transcribe flavonid 3',5'-hydroxylase gene derived from common snapdragon or petunia. Examples of plasmids containing the transcriptional regulatory region of chalcone synthase gene derived from common snapdragon or petunia include plasmids pCGP485 and pCGP653 described in Patent Document 3, and examples of plasmids containing a constitutive transcriptional regulatory region include plasmid PCGP628 (containing a Mac1 promoter) and plasmid pSPB130 (containing a CaMV35S promoter to which is added E12 enhancer) described in Patent Document 4.

However, it is difficult to predict how strongly such promoters function in recombinant plants to be able to bring about a target phenotype. In addition, since repeatedly using the same promoter to express a plurality of foreign genes may cause gene silencing, it is thought that this should be avoided (see Non-Patent Document 5).

Thus, although several promoters have been used to change flower color, a useful promoter corresponding to the host plant and the objective is needed in order to further change to a different flower color.

In particular, chrysanthemum plants (also simply referred to as chrysanthemums) account for about 30% of all wholesale flower sales throughout Japan (Summary of 2007 Flowering Plant Wholesale Market Survey Results, Ministry of Agriculture, Forestry and Fisheries), making these plants an important product when compared with roses accounting for roughly 9% and carnations accounting for roughly 7%. Although chrysanthemums come in flower colors including white, yellow, orange, red, pink and purplish red, there are no existing varieties or closely related wild varieties that produce bluish flowers such as those having a purple or blue color.

Thus, one objective of the selective breeding of bluish flowers is to stimulate new demand. Chrysanthemum flower color is expressed due to a combination of anthocyanins and carotenoids. Anthocyanins are able to express various colors due to differences in the structure of the anthocyanidin serving as the basic backbone, and differences in modification by sugars and organic acids. However, there are known to be two types of anthocyanins that govern chrysanthemum flower color in which cyanidin at position 3 is modified by glucose and malonic acid (cyanidin 3-0-(6"-0-monomalonyl-β-glucopyranoside and 3-0-(3",6"-0-dimalonyl-β-glucopyranoside) (see Non-Patent Document 6). In addition, these structures are comparatively simple (see FIG. 1). This causes the range of flower color attributable to anthocyanins in chrysanthemums to be extremely narrow. However, although the expression of bluish color is primarily the result of anthocyanins, since there is no gene that encodes the key enzyme of flavonoid 3',5'-hydroxylase (F3'5'H) in chrysanthemums, delphinidin-based anthocyanin, which produces blue color, is not biosynthesized in chrysanthemums (see FIG. 1). Therefore, the development of a technology has been sought for controlling the expression of chrysanthemum anthocyanins using genetic engineering techniques in order to be able to produce a chrysanthemum that produces bluish flowers by modifying anthocyanin-based pigment that accumulates in chrysanthemum petals.

As was previously described, although chrysanthemums are the most important flowering plant in Japan, since they are hexaploidal resulting in high ploidy and have a large genome size, in addition to having low transformation efficiency, since they may also cause silencing (deactivation) of transgenes, it is not easy to obtain genetically modified chrysanthemums capable of stable transgene expression. In chrysanthemums transformed with β-glucuronidase (GUS) gene coupled to CaMV35S promoter, the activity of the GUS gene is roughly one-tenth that of tobacco transformed with the same gene, and that activity has been reported to decrease in nearly all individuals after 12 months have elapsed following transformation (see Non-Patent Document 7). Although a promoter of a chlorophyll a/b-bound protein that favorably functions in chrysanthemums has been reported to have been obtained in order to stably express an exogenous gene in chrysanthemums, this promoter is not suitable for expressing genes in flower petals in which there is little chlorophyll present (see Non-Patent Document 8). In addition, when GUS gene coupled to tobacco elongation factor 1 (EF1α) promoter is transformed into chrysanthemums, GUS gene has been reported to be expressed in leaves and petals even after the passage of 20 months or more (see Non-Patent Document 9). Moreover, there are also examples of flower life being prolonged by expressing a mutant ethylene receptor gene in chrysanthemums (see Non-Patent Document 10), flower form being changed by suppressing expression of chrysanthemum AGAMOUS gene (see Non-Patent Document 11), and expression of exogenous genes being increased in chrysanthemums (see Non-Patent Document 12) by using a translation enhancer of tobacco alcohol dehydrogenase (see Patent Document 7).

On the other hand, although there have been examples of successful alteration of chrysanthemum flower color by genetic recombination, including a report of having changed pink flowers to white flowers by suppressing the chalcone synthase (CHS) gene by co-suppression (see Non-Patent Document 13), and a report of having changed white flowers to yellow flowers by suppressing carotenoid cleavage dioxygenase (CCD4a) by RNAi (see Non-Patent Document 14), all of these methods involve alteration of flower color by suppressing expression of endogenous genes, and there have been no successful examples of altering flower color by over-expression of exogenous genes as well as no examples of having realized a change in anthocyanin structure or an accompanying change in flower color.

Although attempts to alter flower color by over-expression of an exogenous gene have been reported that involve transformation with a gene encoding F3'5'H, which is an enzyme required for synthesis of delphinidin (see Patent Document 5 and Non-Patent Document 15), the delphinidin produced due to the action of the transfected F3'5'H gene accumulates in ray petals, and there are no reports of the production of bluish chrysanthemums. In chrysanthemums, even if F3'5'H is expressed with CaMV35S promoter, production of delphinidin is not observed (see Non-Patent Document 15). In addition, expression of a gene expressed with CaMV35S promoter is unsuitable for stable expression, and for example, ends up dissipating accompanying growth of the chrysanthemum transformant (see Non-Patent Document 7). Potato Lhca3.St.1 promoter (see Non-Patent Document 16), chrysanthemum UEP1 promoter (see Non-Patent Document 17) and tobacco EF1α promoter (see Patent Document 6 and Non-Patent Document 9), for example, have been developed for use as promoters enabling efficient and stable expression of exogenous genes in the ray petals of chrysanthemums. However, there have been no reports describing alteration of chrysanthemum flower color by over-expression of an exogenous gene using these promoters. On the basis of the above, in order to produce chrysanthemums in which flower color has been altered by genetic recombination, it is necessary to establish a technology for controlling the expression of flavonoid biosynthesis genes, including the development of a promoter suitable for chrysanthemums.

Although gene expression is mainly controlled by transcriptional regulatory regions, sequences are also known that improve translation of mRNA. For example, the omega sequence derived from tobacco mosaic virus is known to increase the translation efficiency of heterologous genes coupled to the omega sequence both in vitro and in vivo (see Non-Patent Document 18). In addition, a sequence (ADH200) present in the 5'-untranslated region of tobacco alcohol dehydrogenase (NtADH5'UTR) is known to contribute to improved stability of the expression of heterologous genes (see Patent Document 7). In addition, in the case of coupling a 94 bp translation enhancer (ADHNF, see Patent Document 8) present downstream from this sequence to the 3'-side of CaMV35S promoter and further transformation with an expression cassette coupled with GUS gene, this sequence has been reported to contribute to increased translation efficiency in chrysanthemums (see Non-Patent Document 12). However, there are no examples of this sequence being used to change flower color by altering the structure and composition of flavonoids. Since it is necessary to express a heterologous gene in epidermal cells in which flavonoids and anthocyanins primarily accumulate in order to alter flower color, it is difficult to infer from conventional results whether or not NtADH5'UTR (ADH200 or translation enhancer ADHNF) is effective for altering flower color.

PRIOR ART DOCUMENTS

Patent Documents

Patent Document 1: WO 96/25500
Patent Document 2: WO 01/72984
Patent Document 3: WO 94/28140
Patent Document 4: WO 05/17147
Patent Document 5: U.S. Pat. No. 5,948,955
Patent Document 6: Japanese Unexamined Patent Publication No. 2004-65096
Patent Document 7: U.S. Pat. No. 6,573,429
Patent Document 8: Japanese Unexamined Patent Publication No. 2003-79372

Non-Patent Documents

Non-Patent Document 1: Plant J., 54, 737-749, 2008
Non-Patent Document 2: Agricultural and Biological Chemistry, 53, 797-800, 1989
Non-Patent Document 3: Plant Cell Physiology, 37, 49-59, 1996
Non-Patent Document 4: Plant Molecular Biology, 15, 373-381, 1990
Non-Patent Document 5: Annals of Botany, 79, 3-12,
Non-Patent Document 6: Journal of Horticultural Science & Biotechnology, 81, 728-734, 2006
Non-Patent Document 7: Plant Biotechnology, 17, 241-245, 2000
Non-Patent Document 8: Breeding Science, 54, 51-58, 2004
Non-Patent Document 9: Japan Agricultural Research Quarterly, 39, 269-274, 2005
Non-Patent Document 10: Postharvest Biology and Technology, 37, 101-110, 2005
Non-Patent Document 11: Plant Biotechnology, 25, 55-59, 2008
Non-Patent Document 12: Plant Biotechnology, 25, 69-75, 2008
Non-Patent Document 13: Bio/Technology, 12, 268, 1994
Non-Patent Document 14: Plant Physiology, 142, 1193, 2006
Non-Patent Document 15: J. Plant Biol., 50, 626, 2007
Non-Patent Document 16: Mol. Breed., 8, 335, 2001
Non-Patent Document 17: Transgenic Res., 11, 437, 2002
Non-Patent Document 18: Nucleic Acids Research, 15, 3257-3273, 1987

SUMMARY OF THE INVENTION

Problems to be Solved by the Invention

An object to be solved by the present invention is to provide a method for producing a chrysanthemum plant containing delphinidin in the petals thereof by using the transcriptional regulatory region of chrysanthemum-derived flavanone 3-hydroxylase (F3H) gene, and a chrysanthemum plant, progeny or vegetative proliferation product thereof, or a part or tissue thereof, and particularly a petal or cut flower thereof, transformed with that regulatory region.

Means for Solving the Problems

As a result of conducting extensive studies to solve the aforementioned problems, the inventors of the present invention found that when flavonoid 3',5'-hydroxylase (F3'5'H) gene is expressed in chrysanthemum using a transcriptional regulatory region of flavanone 3-hydroxylase (F3H) derived from chrysanthemum, a large amount of delphinidin accumulates in the petals thereof, flower color changes, and flower color changes further due to an even larger accumulation of delphinidin as a result of adding a translational enhancer derived from tobacco alcohol dehydrogenase gene, and confirmed the usefulness thereof through experimentation, thereby leading to completion of the present invention.

Namely, the present invention is as described below.

[1] A method for producing a chrysanthemum plant containing delphinidin in the petals thereof comprising the step of expressing flavonoid 3',5'-hydroxylase (F3'5'H) in a chrysanthemum plant using as a transcriptional regulatory region a nucleic acid selected from the group consisting of:

(1) a nucleic acid containing the nucleotide sequence indicated in SEQ ID NO. 34 or SEQ ID NO. 87;

(2) a nucleic acid able to function as a transcriptional regulatory region of flavanone 3-hydroxylase (F3H) gene derived from chrysanthemum, and containing a nucleotide sequence in which the nucleotide sequence indicated in SEQ ID NO. 34 or SEQ ID NO. 87 has been modified by addition, deletion and/or substitution of one or several nucleotides;

(3) a nucleic acid able to function as a transcriptional regulatory region of flavanone 3-hydroxylase (F3H) gene derived from chrysanthemum, and able to hybridize under highly stringent conditions with a nucleic acid composed of a nucleotide sequence complementary to the nucleotide sequence indicated in SEQ ID NO. 34 or SEQ ID NO. 87; and, (4) a nucleic acid able to function as a transcriptional regulatory region of flavanone 3-hydroxylase (F3H) gene derived from chrysanthemum, and having sequence identity of at least 90% with the nucleotide sequence indicated in SEQ ID NO. 34 or SEQ ID NO. 87.

[2] The method described in [1] above, wherein the flavonoid 3',5'-hydroxylase (F3'5'H) is derived from bellflower (campanula), cineraria, verbena and pansy #40.

[3] The method described in [1] or [2] above, wherein a translational enhancer derived from tobacco alcohol dehydrogenase gene is further used in addition to the transcriptional regulatory region.

[4] The method described in any of [1] to [3] above, wherein an expression vector or expression cassette is used in which the translational enhancer is coupled directly to a start codon of the F3'5'H gene.

[5] The method described in any of [1] to [4] above, wherein the content of delphinidin in the petals is 25% by weight or more of the total weight of anthocyanidins.

[6] A chrysanthemum plant, progeny thereof, or vegetative proliferation product, part or tissue thereof, containing the nucleic acid described in [1] above or produced according to the method described in any of [1] to [5] above.

[7] The chrysanthemum plant, progeny thereof, or vegetative proliferation product, part of tissue thereof, described in [6] above, which is a cut flower.

[8] A cut flower processed product using the cut flower described in [7] above.

Effects of the Invention

According to the present invention, it was determined that when flavonoid 3',5'-hydroxylase (F3'5'H) gene is expressed in chrysanthemum using the transcriptional regulatory region of flavanone 3-hydroxylase (F3H) derived from chrysanthemum, more delphinidin accumulates in the flower petals than in the case of using another promoter, and when the flower color becomes bluer, an even larger amount of delphinidin accumulates as a result of adding a translational enhancer derived from tobacco alcohol dehydrogenase gene, thereby causing the flower color to become even bluer.

EMBODIMENTS OF THE INVENTION

Figure 1:
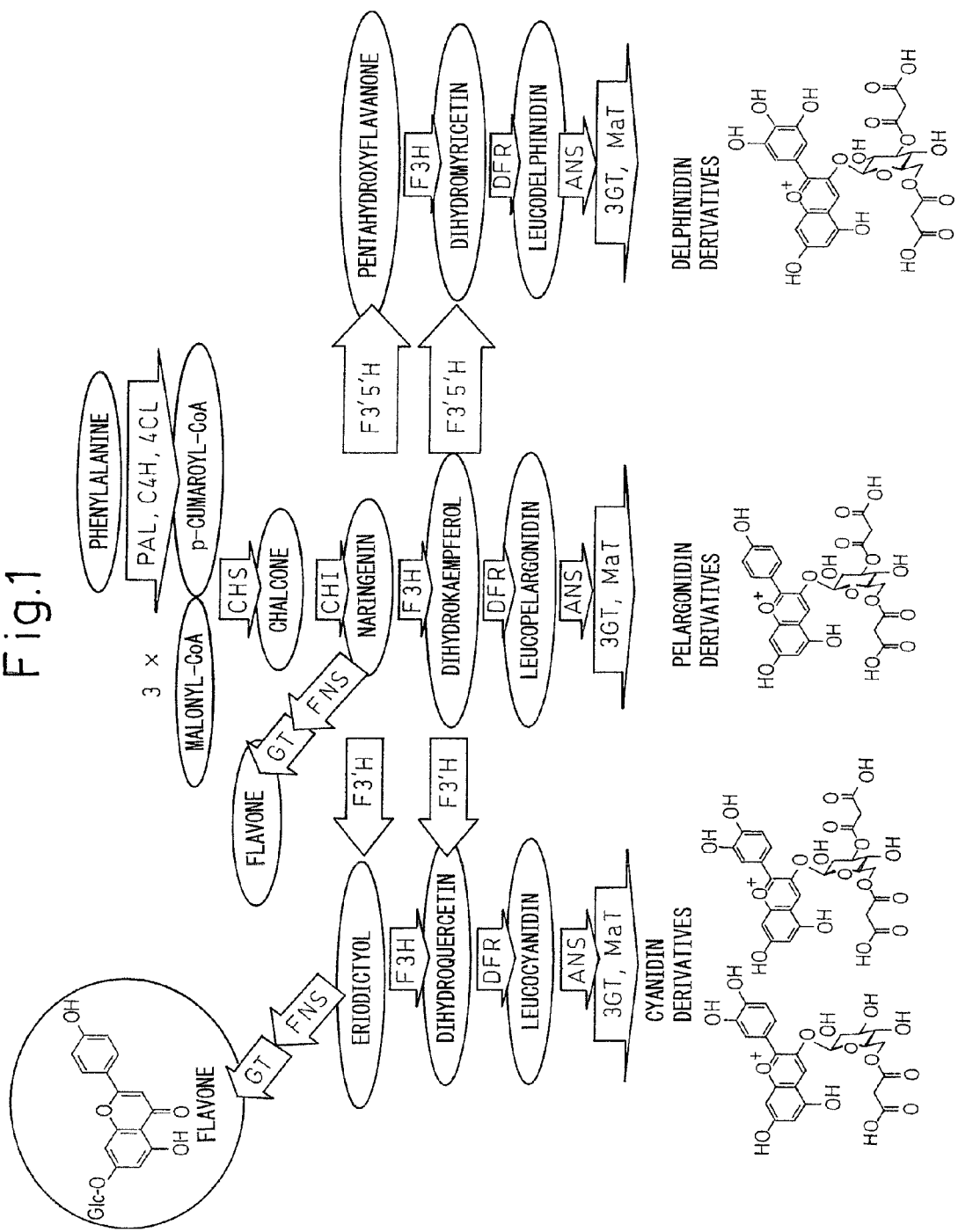
FIG. 1 is a schematic diagram of the flavonoid biosynthesis pathway in transformed chrysanthemum transformed with F3'5'H gene.
Figure 2:
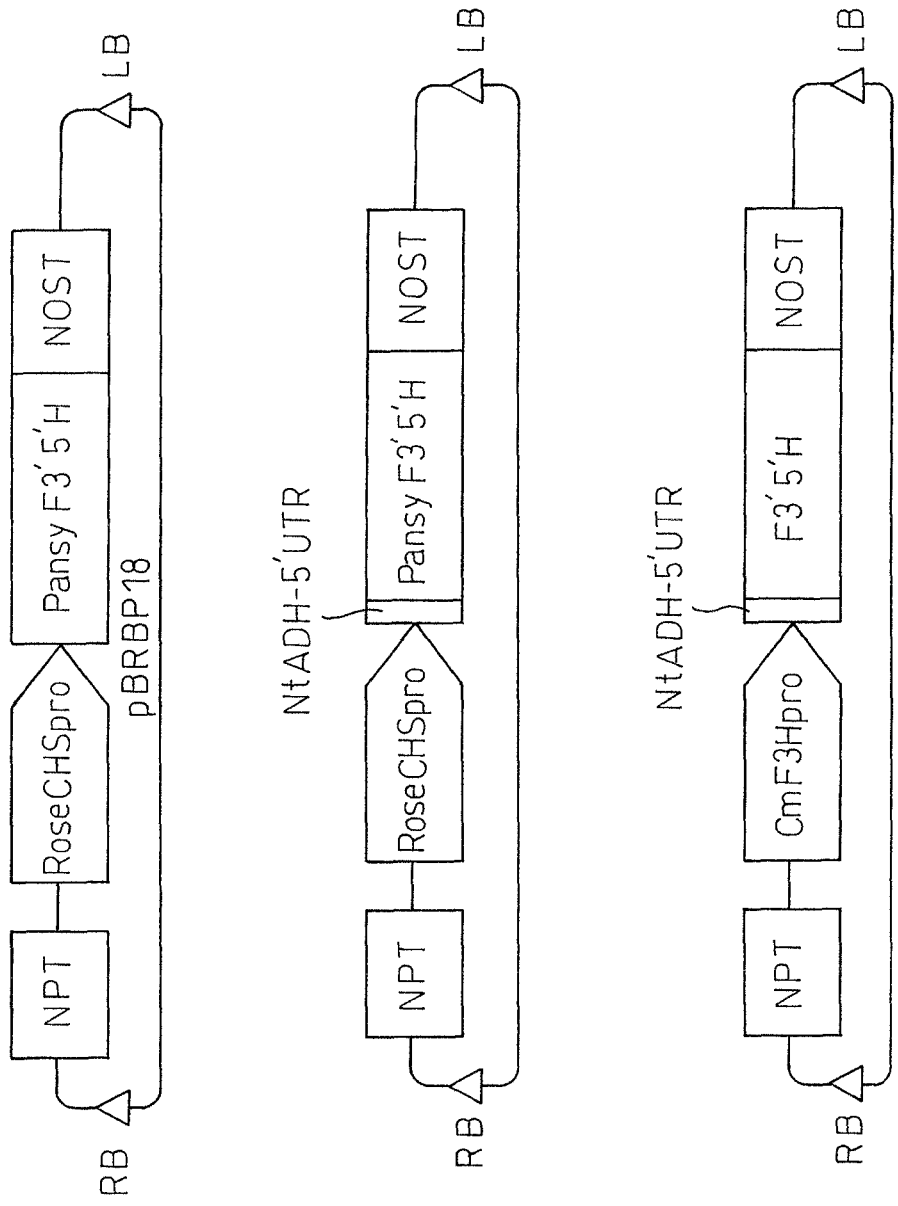
FIG. 2 is a schematic diagram of a binary vector for introducing F3'5'H gene.

The present invention relates to a method for producing a chrysanthemum plant containing delphinidin in the petals thereof, comprising transforming chrysanthemum with a vector containing a gene cassette that causes expression of flavonoid 3',5'-dehydroxylase (F3'5'H) by the 5'-region of a gene that encodes chrysanthemum flavanone 3-hydroxylase (F3H) (also referred to as "CmF3Hpro" or "chrysF3H5'"). The gene cassette preferably contains a translational enhancer derived from tobacco alcohol dehydrogenase gene (see bottom of FIG. 2). The delphinidin content in the flower petals is preferably 25% by weight or more of the total weight of anthocyanidins, and the color of the flower petals is altered towards blue. The present invention also relates to a chrysanthemum plant, progeny thereof, or vegetative proliferation product, part or tissue thereof, produced according to that method or containing CmF3Hpro. The part or tissue is preferably a flower petal or cut flower.

In the present description, an "expression cassette" refers to a DNA fragment in which a promoter and a terminator are coupled to arbitrary nucleic acids.

Figure 3:
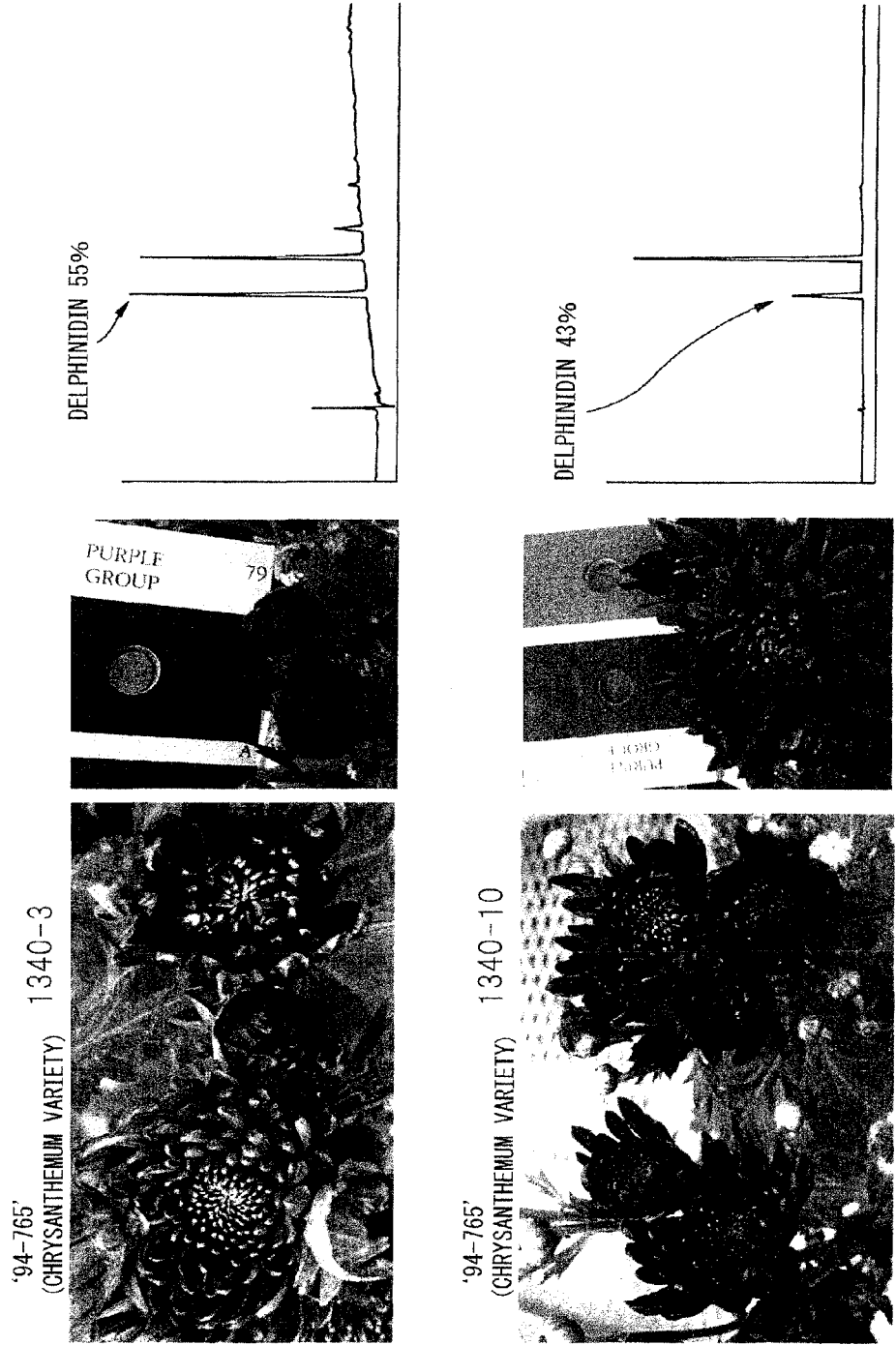
FIG. 3 indicates the flower color and ratio of delphinidin content in transformed individuals transformed with chrysanthemum F3Hpro::ADHNF-bellflower F3'5'H::NOSter.

According to the present invention, since F3'5'H gene is expressed in ray petals of chrysanthemum, and that enzyme protein is synthesized and functions, a chrysanthemum having a bluish flower color can be produced by allowing delphinidin-based anthocyanin to be synthesized and accumulate. Although accumulation of delphinidin (max. 5.4%) was confirmed in the case of using RoseCHSpro (rose chalcone synthase (CHS) gene promoter), R. rugosa DFRpro (Rugosa rose dihydroflavonol-4-reductase (DFR) gene promoter), R. rugosa F3Hpro (R. rugosa flavanone 3-hydroxylase (F3H)) or Viola F3'5'H#40pro (pansy F3'5'H gene promoter) for the promoter contained in the gene cassette used to express F3'5'H (see Table 1), this did not lead to flower color becoming bluish. Therefore, as a result of repeatedly conducting expression experiments on F3'5'H using various types of promoters in order to discover an effective promoter for enhancing accumulation of delphinidin in chrysanthemum flower petals and making flower color bluish, CmF3Hpro was determined to be an effective promoter. The use of CmF3Hpro made it possible to improve accumulation of delphinidin in comparison with the case of using other promoters (see Table 1, mean: 31.4%, max.: 80.5%), and led to the attaining of bluish flower color (see FIG. 3, RHS color chart 79A, 77A, 72A and 72B). In addition, within the F3'5'H gene expressed by CmF3Hpro, F3'5'H derived from bellflower (delphinidin accumulation rate: max. 81%), cineraria (delphinidin accumulation rate: max. 36%), verbena and pansy (delphinidin accumulation rate: max. 27% to 28%) were found to have the ability to change chrysanthemum flower color to purple. Moreover, transformation with a gene cassette directly coupled with tobacco ADH translational enhancer (see Patent Document 8) was successful in altering flower color by enabling anthocyanin having delphinidin for the basic backbone thereof to be efficiently accumulated in ray petals of chrysanthemum (see Table 1, FIG. 3). Furthermore, direct coupling refers to coupling without containing a surplus nucleic acid sequence between one polynucleotide and another polynucleotide.

An example of a transcriptional regulatory region according to the present invention is a nucleic acid composed of a nucleotide sequence indicated in SEQ ID NO. 34 or SEQ ID NO. 87. However, a promoter composed of a base sequence in which several (1, 2, 3, 4, 5, 6, 7, 8, 9 or 10) nucleotides has been added, deleted and/or substituted in a nucleic acid composed of a nucleotide sequence indicated in SEQ ID NO. 34 or SEQ ID NO. 87 is also thought to maintain activity similar to that of the original promoter. Thus, the transcriptional regulatory region according to the present invention can also be a nucleic acid composed of a nucleotide sequence in which one or several nucleotides have been added, deleted and/or substituted in the nucleotide sequence indicated in SEQ ID NO. 34 or SEQ ID NO. 87 provided the nucleic acid is able to function as a transcriptional regulatory region of flavanone 3-hydroxylase (F3H) gene derived from chrysanthemum.

The transcriptional regulatory region according to the present invention can also be a nucleic acid able to function as a transcriptional regulatory region of flavanone 3-hydroxylase (F3H) gene derived from chrysanthemum and able to hybridize under highly stringent conditions with the nucleotide sequence indicated in SEQ ID NO. 34 or SEQ ID NO. 87, or a nucleic acid able to function as a transcriptional regulatory region of flavanone 3-hydroxylase (F3H) gene derived from chrysanthemum and has sequence identity of at least 90% with the nucleotide sequence indicated in SEQ ID NO. 34 or SEQ ID NO. 87.

Examples of these nucleic acids include nucleic acids composed of nucleotide sequences having sequence identity with the nucleotide sequence indicated in SEQ ID NO. 34 of preferably about 70% or more, more preferably about 80%, 81%, 82%, 83%, 84%, 85%, 86%, 87%, 88%, 89%, 90%, 91%, 92%, 93%, 94%, 95%, 96%, 97% or 98%, and most preferably about 99%.

Here, stringent conditions refer to hybridization conditions easily determined by a person with ordinary skill in the art that determined empirically typically dependent on probe length, washing temperature and salt concentration. In general, the temperature for suitable annealing becomes higher the longer the probe, and the temperature becomes lower the shorter the probe. Hybridization is generally dependent on the ability of denatured DNA to anneal in the case a complementary strand is present in an environment at a temperature close to or below the melting temperature thereof. More specifically, an example of lowly stringent conditions consists of washing and so forth in 0.1% SDS solution at 5×SSC under temperature conditions of 37° C. to 42° C. in the filter washing stage following hybridization. In addition, an example of highly stringent conditions consists of washing and so forth in 0.1% SDS at 0.1×SSC and 65° C. in the washing stage. The use of more highly stringent conditions makes it possible to obtain polynucleotides having higher homology or identity.

In the present invention, the flavonoid 3',5'-hydroxylase (F3'5'H) gene is preferably derived from bellflower (campanula), cineraria, verbena or pansy #40. In the present invention, a translation enhancer derived from tobacco alcohol dehydrogenase is preferably further used in addition to the transcriptional regulatory region. In addition, the translation enhancer is preferably directly coupled to a start codon of the F3'5'H gene in a gene cassette of an expression vector.

In the method of the present invention, the delphinidin content in the flower petals is preferably 25% by weight or more of the total weight of anthocyanidins.

The present invention is a chrysanthemum plant, progeny thereof, or vegetative proliferation product, part or tissue thereof, produced according to the method of the present invention or transformed with the aforementioned nucleic acid, and is preferably a flower petal or cut flower.

The present invention also relates to a processed product that uses the aforementioned cut flower (cut flower processed product). Here, a cut flower processed product includes, but is not limited to, a pressed flower, preserved flower, dry flower or resin-sealed product obtained by using the cut flower.

EXAMPLES

The following provides a detailed explanation of the present invention through examples thereof.

Molecular biological techniques were carried out in accordance with Molecular Cloning (Sambrook and Russell, 2001) unless specifically indicated otherwise.

The following Reference Examples 1 to 9 are examples of using a promoter other than the 5'-region of a gene encoding flavanone 3-hydroxylase (F3H) of chrysanthemum (CmF3Hpro), while on the other hand, Examples 1 to 10 are examples relating to the 5'-region of a gene encoding flavanone 3-hydroxylase (F3H) of chrysanthemum (CmF3Hpro).

Reference Example 1

Expression of F3'5'H Gene by Tobacco EF1α Promoter pBIEF1α described in Patent Document 6 was digested with restrictases HindIII and BamHI to obtain a roughly 1.2 kb DNA fragment containing a promoter sequence of tobacco EF1α. This DNA fragment was inserted into the 5'-side of iris DFR cDNA of pSPB909 described in Patent Document 4 to obtain a plasmid pSLF339. A plasmid pSLF340 was similarly constructed in which petunia DFR cDNA (described in International Publication WO 96/36716) was inserted instead of iris DFR cDNA.

A plasmid obtained by inserting a BP40 fragment of pansy F3'5'H gene, excised by partial digestion with BamHI and XhoI from pCGP1961 described in Patent Document 4, into BamHI and SalI sites of pSPB176 (described in Plant Science, 163, 253-263, 2002) was designated pSPB575. The promoter portion of this plasmid was replaced with the promoter of the aforementioned tobacco EF1α using HindIII and BamHI to obtain pSLF338. A fragment containing iris DFR cDNA was inserted into pSLF339 digested with AscI at this AscI site. The resulting plasmid was designated pSLF346. This plasmid pSLF346 is designed to express pansy F3'5'H and iris DFR genes in plants under the control of the promoter of tobacco EF1α.

Plasmid pLHF8 containing lavender F3'5'H cDNA is described in International Publication WO 04/20637. Plasmid pSPB2772 was obtained by coupling this plasmid to the DNA fragment having the higher molecular weight among a DNA fragment obtained by digesting this plasmid with BamHI and XhoI and a DNA fragment of pSPB176 obtained by digesting with BamHI and SalI. In this plasmid, lavender-derived F3'5'H cDNA is coupled to CaMV35S promoter to which has been added E12 enhancer. This promoter portion was replaced with the aforementioned promoter of tobacco EF1α using HindIII and BamHI to obtain plasmid pSPB2778. A fragment containing petunia DFR cDNA within pSFL340 digested with AscI was inserted into this AscI site. The resulting plasmid was designated pSPB2780. This plasmid pSPB2780 is designed so as to express lavender F3'5'H and petunia DFR genes in plants under the control of tobacco EF1α promoter.

Plasmid pSPB2777 was obtained by replacing the promoter portion of plasmid pSPB748 described in Plant Biotechnol., 23, 5-11 (2006) (in which butterfly pea-derived F3'5'H cDNA is coupled to CaMV35S promoter to which has been added E12 enhancer) with the aforementioned promoter of tobacco EF1α using HindIII and BamHI. A fragment of pSLF340 digested with AscI containing petunia DFR cDNA was inserted into this AscI site. The resulting plasmid was designated pSPB2779. This plasmid pSPB2779 is designed to express butterfly pea F3'5'H and petunia DFR genes in plants under the control of the promoter of tobacco EF1α.

Each of the aforementioned plasmids pSFL346, pSPB2780 and pSPB2779 were transformed into Agrobacterium and then transfected into chrysanthemum variety 94-765 using this transformed Agrobacterium. Although anthocyanidins in flower petals of the transformed chrysanthemum were analyzed, delphinidin was not detected.

Reference Example 2

Chrysanthemum Transfected with Cineraria F3'5'H Gene Promoter

RNA was extracted based on an established method from the petals of a bud of blue Cineraria Senetti (Suntory Flowers Ltd.). A cDNA library was produced using the ZAP-cDNA® Library Construction Kit (Stratagene Corp., Catalog No. 200450) in accordance with the method recommended by the manufacturer using poly-A+RNA prepared from this RNA. This cDNA library was then screened using butterfly pea F3'5'H cDNA (Clitoria ternatea, see Plant Biotechnology, 23, 5-11 (2006)) labeled with the DIG System (Roche Applied Science) according to the method recommended by the manufacturer. Forty eight phages indicating signal were isolated. Plasmids were obtained from these phages by in vivo excision according to the method recommended by the manufacturer (Stratagene).

The nucleotide sequences of the cDNA portions contained in these plasmids were determined, a Blast search was made of DNA databases, numerous genes were obtained that demonstrated homology with cytochrome P450, and these genes were able to be classified into 8 types. Among these, the entire nucleotide sequence of Ci5a18 (SEQ ID NO. 77), which was presumed to be classified as CYP75B, was determined. A pBluescript SKII-plasmid containing this sequence was designated pSPB2774.

Chromosomal DNA was extracted from a leaf of the same Cineraria, and a chromosome library was produced using the λBlueSTAR™ Xho I Half-Site Arms Kit (Novagen, on the Internet at merckbiosciences.com/product/69242). The resulting 200,000 plaques were screened using a Ci5a18 cDNA fragment labeled with DIG. This cDNA fragment was amplified using Ci5a18 as template and using primers Ci5a18F1 (SEQ ID NO. 81: 5'-CATCTGTTTTCTGC-CAAAGC-3') and Ci5a18R1 (SEQ ID NO. 82: 5'-GGATT-AGGAAACGACCAGG-3'). Four plaques were ultimately obtained from the resulting 17 plaques, and these were converted to plasmids by in vivo excision. When their DNA nucleotide sequences were determined, they were found to contain the same sequences. Among these, a clone designated gCi01-pBluestar was used in subsequent experiments. The cloned nucleotide sequence of gCi01-pBluestar is shown in SEQ ID NO. 79. This sequence was expected to contain a 5'-untranslated containing a sequence having promoter activity of cineraria F3'5'H, a translated region, and a 3'-untranslated region.

A roughly 5.7 kb DNA fragment excised from gCi01-pBluestar with PvuI and EcoRV (SEQ ID NO. 80) was blunted using a DNA blunting kit (Takara). This DNA fragment was then cloned into the SmaI site of pBinPLUS and designated pSPB3130. This binary vector had an nptII gene able to be used to screen the T-DNA region with kanamycin.

pSPB3130 was transformed into chrysanthemum variety 94-765 using an *Agrobacterium* method. Although anthocyanidins in the petals of the transformed chrysanthemum were analyzed, delphinidin was not detected and flower color did not change.

Reference Example 3

Production of Delphinidin Using Rose Chalcone Synthase Gene Promoter

A binary vector was constructed in which pansy-derived F3'5'H BP#18 gene was coupled to a rose-derived chalcone synthase promoter described in PCT International Patent Publication No. PCT/AU03/01111, and this binary vector was designated pBRBP18. The gene contained in this binary vector was transformed into chrysanthemum variety 94-765 as described in Reference Examples 1 and 2. When anthocyanidins in the flower petals of the transformed chrysanthemum were analyzed, although a maximum of 5.4% of delphinidin was detected with respect to all anthocyanidins, there was no change in flower color observed.

In addition, pSPB3325 (rose CHSpro::pansy #18+rose CHSp:: chrysanthemum F3'H IR) described in the ninth row from the top in Table 1 is an example of the production of delphinidin using rose chalcone synthase gene promoter, and delphinidin production in this example reached a maximum of 3.6%.

Reference Example 4

Production of Delphinidin Using Pansy F3'5'H Gene Promoter (1) Cloning of Perilla Anthocyanin 3-Acyl Transferase Chromosome Gene There are known to be red varieties of perilla in which anthocyanins accumulate in the leaves and green varieties in which they do not. Chromosomal DNA from the leaves of the former was prepared using a reported method (Plant Mol. Biol., December 1997, 35(6), 915-927). This chromosomal DNA was partially decomposed with Sau3AI (Toyobo), and a fraction containing a 10 kb to 15 kb DNA fragment was recovered using a sucrose density gradient method. This fragment was then inserted into the BamHI site of EMBL3 (Promega), a type of lambda phage vector, using a known method to prepare a genomic DNA library. The resulting library was screened using pSAT208 (see Plant Cell Physiol., April 2000, 41(4), 495-502), which is cDNA of anthocyanin 3-acyl transferase derived from perilla, as a probe. Screening of the library was in accordance with a previously reported method (Plant Cell Physiol., July 1996, 37(5), 711-716). Plaques that hybridized with the probe were blunted and cultured, and DNA was prepared from the resulting phage.

(2) Determination of Nucleotide Sequence of Perilla Anthocyanin 3-Acyl Transferase Chromosome Gene 10 μg of the DNA obtained above were digested with XbaI and isolated with 0.7% agarose gel followed by blotting onto Hybond-N (Amersham). When this film was hybridized in the same manner as previously described, a roughly 6.8 kb DNA fragment was found to hybridize with the probe. After digesting 20 μg of the same DNA with XbaI and isolating with 0.7% agarose gel, a roughly 6.8 kb DNA fragment was purified using a GeneClean Kit and coupled with pBluescript SKII-digested with XbaI. The resulting plasmid was designated pSPB513. The DNA sequence derived from perilla contained in this plasmid was determined by primer walking. The nucleotide sequence thereof is shown in SEQ ID NO. 4. This sequence contains a region that demonstrates high homology with anthocyanin 3-acyltransferase cDNA in the form of pSAT208, the amino acid sequence (SEQ ID NO. 6) of protein encoded by this region was observed to demonstrate substitution of 19 amino acid residues and deletion of 2 amino acid residues in comparison with the amino acid sequence encoded by pSAT208, and there were no introns observed. In addition, the sequence of the region demonstrating high homology with pSAT208 contained a 3438 bp sequence upstream from ATG that was thought to be the start codon, and a 2052 bp sequence downstream from TAA that was thought to be the stop codon thereof. A different open reading frame (ORF, SEQ ID NO. 5), which was not anthocyanin 3-acyltransferase, was present in the aforementioned 3438 bp sequence. The following experiment was conducted to amplify the transcriptional regulatory region of shiso (perilla) anthocyanin 3-acyl transferase gene, excluding this portion.

(3) Amplification of Transcriptional Regulatory Region of Shiso Anthocyanin 3-Acyltransferase Gene PCR (25 cycles of a reaction consisting of holding for 1 minute at 95° C., 1 minute at 52° C., 2 minutes at 72° C. and 1 minute at 95° C.) was carried out using 1 ng of pSPB513 as template and two types of primers (5'-AAGCTTAACTATTATGATCCCACAGAG-3' (SEQ ID NO. 7, underline indicates HindIII recognition sequence) and 5'-GGATCCGGCGGTGTTGAACGTAGC-3' (SEQ ID NO. 8, underline indicates BamHI recognition sequence)). The amplified roughly 1.1 kb DNA fragment was digested with HindIII and BamHI.

The plasmid pSPB567 described in Patent Document 4 (in which pansy-derived flavonoid 3',5'-hydroxylase gene is coupled to the 3'-side of cauliflower mosaic 35S promoter to which has been added E12 enhancer, and in which a nopaline synthase terminator is further coupled to the 3'-side thereof) was digested with PacI, and a DNA fragment containing pansy-derived flavonoid 3',5'-hydroxylase gene was cloned into the PacI site of pBin+. A plasmid in which the cauliflower mosaic 35S promoter to which E12 enhancer was added is present close to the AscI site of pBin+ in the resulting plasmid was designated pSPB575. This plasmid was then digested with HindIII and BamHI, and a DNA fragment obtained by digesting a roughly 1.1 kb DNA fragment containing the transcriptional regulatory region of perilla anthocyanin 3-acyltransferase with HindIII and BamHI was inserted therein. The resulting plasmid was designated pSFL205.

Plasmid pSFL205 was digested with HindIII and SacI, and a roughly 100 bp DNA fragment was recovered. This DNA fragment, a roughly 4 kb DNA fragment obtained by digesting pSPB513 with SacI and XbaI, and a plasmid pBin+(see Transgenic Research, 4, 288-290, 1995) digested with HindIII and XbaI were coupled to obtain plasmid pSPB3311. This plasmid pSPB3311 is a binary vector that contains the nucleotide sequence indicated in SEQ ID NO. 2, and contains the transcriptional regulatory region of perilla anthocyanin 3-acyltransferase gene and an untranslated region of the 3'-side thereof.

(4) Construction of pSPB3323

The transcriptional regulatory region of pansy flavonoid 3',5'-hydroxylase gene BP#40 (see WO 04/020637) was amplified as described below using the Takara LA PCR™ In Vitro Cloning Kit.

Chromosomal DNA was prepared from a pansy leaf using the DNA Easy Plant Kit (Qiagen). 3 µg of the chromosomal DNA were digested with restriction enzyme HindIII. The digested DNA was coupled with HindIII terminal DNA (included in Takara LA PCR™ In Vitro Cloning Kit) by reacting for 40 minutes at 16° C. using Ligation High (Takara). After diluting 4 µl of the reaction mixture with 10 µl of water and denaturing the coupled DNA by treating for 10 minutes at 94° C., the reaction mixture was cooled in ice. 5 pmol of primer C1 (5'-GTACATATTGTCGTTAGAACGCG-TAATACGACTCA-3', SEQ ID NO. 9, included in the kit as a partial sequence of HindIII cassette sequence) and 5 pmol of primer BP40-i5 (5'-AGGTGCATGATCGGACCATACTTC-3', SEQ ID NO. 10, equivalent to complementary strand of translated region of BP#40) were then added followed by repeating 30 cycles of a reaction in 25 µl of the reaction mixture consisting of 20 seconds at 98° C. and 15 minutes at 68° C. in accordance with the kit protocol. The reaction mixture was then diluted 10-fold with water. After reacting for 5 minutes at 98° C. in 25 of a reaction mixture containing 5 pmol of primer C2 (5'-CGTTAGAACGCGTAATAC-GACTCACTATAGGGAGA-3', SEQ ID NO. 11, included in kit as partial sequence of HindIII cassette sequence) and 5 pmol of primer BP40-i7 (5'-GACCATACTTCTTAGC-GAGTTTGGC-3', SEQ ID NO. 12) using 0.5 µl of this dilution as template, 30 cycles of a reaction were repeated consisting of reacting for 20 seconds at 98° C. and 15 minutes at 68° C.

The resulting DNA fragment was ligated into plasmid pCR2.1 (Invitrogen). When the nucleotide sequence of the resulting DNA was determined, the sequence was observed to have locations that did not coincide with the cDNA nucleotide sequence of BP#40. This is thought to be due to the occurrence of an error during PCR. The following procedure was carried out for the purpose of amplifying an error-free sequence.

In order to amplify a roughly 2 kb 5'-untranslated region and a 200 bp translated region of BP#40, PCR was carried out in 25 µl of a reaction mixture using 200 ng of pansy genomic DNA as template and using 50 pmol of primer BP40-i7 (SEQ ID NO. 12) and 50 pmol of primer BP40 pro-F (5'-ACT-CAAACAAGCATCTCGCCATAGG-3', SEQ ID NO. 3, sequence in 5'-untranslated region of BP#40 gene). After treating for 5 minutes at 98° C., a reaction consisting of 20 seconds at 98° C. and 15 minutes at 68° C. was repeated for 30 cycles. The amplified DNA fragment was inserted into pCR2.1. This DNA fragment contained a roughly 2.1 kbp 5'-untranslated region and a 200 bp translated region. This plasmid was designated pSFL614. The nucleotide sequence of plasmid pSFL614 is shown in SEQ ID NO. 14.

The roughly 2.1 bp 5'-untranslated region (BP40pro, SEQ ID NO. 15) contained in pSFL614 was used to transcribe BP#40 gene. At this time, the BamHI site was changed to NheI. After using 1 ng of pSFL614 as template, adding 50 pmol of primer BP40pro-HindIII-F (5'-AAG CTT GTG ATC GAC ATC TCT CTC C-3', SEQ ID NO. 16), 50 pmol of primer BP40pro-NehI-R (5'-CGA GGC TAG CTA AAC ACT TAT-3', SEQ ID NO. 17), and holding for 5 minutes at 98° C. in 25 µl of the reaction mixture, a reaction consisting of 20 seconds at 98° C. and 15 minutes at 68° C. was repeated for 25 cycles. The amplified DNA fragment was cloned into pCR2.1. This sequence was determined to be free of errors attributable to PCR by confirming the nucleotide sequence thereof. This plasmid was then digested with HindIII and NheI to obtain a 470 bp DNA fragment. This DNA fragment was designated fragment A.

After using 1 ng of pSLF614 as template, adding 50 pmol of primer BP40pro-NehI-F (5'-TTT AGC TAG CCT CGA AGT TG-3', SEQ ID NO. 18) and 50 pmol of primer BP40pro-BamHI-R (5'-GGA TCC CTA TGT TGA GAA AAA GGG ACT-3', SEQ ID NO. 19) and Ex-Taq DNA polymerase, and holding for 5 minutes at 98° C. in 25 µl of the reaction mixture, a reaction consisting of 20 seconds at 98° C. and 15 minutes at 68° C. was repeated for 25 cycles. The amplified DNA fragment was cloned into pCR2.1. This sequence was determined to be free of errors attributable to PCR by confirming the nucleotide sequence thereof. This plasmid was then digested with HindIII and NheI to obtain a 630 bp DNA fragment. This DNA fragment was designated fragment B.

The larger fragment of DNA fragments formed by digesting plasmid pSPB567 described in Patent Document 4 with HindIII and NheI was recovered, and coupled with the aforementioned fragment A and fragment B to obtain pSFL620.

After digesting pSFL620 with PacI, a roughly 3.2 kb DNA fragment was recovered. This DNA fragment was inserted into the PacI site of pBin+. The resulting plasmid was designated pSBP3317. A fragment obtained by digesting the aforementioned pSPB3311 with AscI and XbaI was cloned into the AscI and XbaI sites of pSBP3317, and the resulting plasmid was designated pSPB3323.

(5) Expression of Perilla Anthocyanin 3-Acyl Transferase Genomic Gene and Pansy F3'5'H Gene in Chrysanthemum The pSPB3323 prepared in (4) above was introduced into *Agrobacterium* and chrysanthemum variety 94-765 (Seikoen, not sold) was transformed according to a known method using this *Agrobacterium*. Six transformed strains were acquired.

Anthocyanidins extracted according to the method described below were analyzed. Ray petals were frozen and then crushed followed by extracting 50 mg to 100 mg of the crushed petal with 500 μL of 1% hydrogen chloride-methanol, adding 500 μL of 4 N hydrochloric acid (HCl) to this extract and mixing, and hydrolyzing for 1 hour at 100° C. After cooling the solution following hydrolysis, 1 ml of 0.05 M trifluoroacetic acid (TFA) was added and mixed therein. Next, this solution was added to Sep-Pak C18 (Millipore) to adsorb the hydrolysis product. The Sep-Pak C18 was preliminarily washed with 80% acetonitrile (MeCN) and equilibrated with 0.05 M TFA. After washing the hydrolysis product adsorbed to the Sep-Pak C18 with 0.05 M TFA, the hydrolysis product was further washed with 20% MeCN and 0.05 M TFA followed by eluting the hydrolysis product with 80% MeCN and 0.05 M TFA to obtain an analysis sample.

The analysis sample was analyzed under the following conditions using high-performance liquid chromatography. An Inertsil ODS-2 column (particle diameter: 5 μm, 4.6×250 mm, GL Sciences) was used for the column, the flow rate was 0.8 ml/min, the mobile phase contained 1.5% phosphoric acid, and isocratic elution was carried out for 20 minutes using a linear concentration gradient from 5% acetic acid and 6.25% acetonitrile to 20% acetic acid and 25% acetonitrile, followed by eluting for 5 minutes with 25% acetonitrile containing 1.5% phosphoric acid and 20% acetic acid. Detection was carried out using the Agilent 1100 Series Diode Array Detector (GL Sciences) over a wavelength region of 250 nm to 600 nm, and the abundance ratios of each of the anthocyanidins was determined according to the area of optical absorbance at 530 nm.

As a result of analysis, delphinidin was detected at ratios of 0.9%, 0.8%, 1.4% and 0.6% of the total amount of anthocyanidins in transformants consisting of analyzed strains 1300-3, 1300-4, 1300-5 and 1300-6, respectively. Although this suggests that BP#40 transcriptional regulatory region of pansy governs transcription of BP#40, this did not lead to a change in flower color.

Reference Example 5

Production of Delphinidin in Chrysanthemum Using Rugosa Rose DFR Promoter

A Rugosa rose Genomic DNA library was prepared in the manner described below using the λBlueSTAR™ Xho I Half-Site Arms Kit (Novagen, on the Internet at merckbiosciences.com/product/69242). Chromosomal DNA was prepared from a young leaf of Rugosa rose using Nucleon Phytopure™ (Tepnel Life Sciences). Roughly 100 μg of chromosomal DNA was digested with restriction enzyme Sau3AI.

This DNA fragment was then partially filled in with DNA polymerase I Klenow fragment (Toyobo) in the presence of dGTP and dATP, and fractionated by sucrose density gradient centrifugation. DNA of about 13 kb was recovered and concentrated by ethanol precipitation. Roughly 180 ng of DNA were ligated for 15 hours at 4° C. with 1 μL of the λBlueSTAR™ Xho I Half-Site Arms Kit, followed by carrying out in vitro packaging to obtain a genomic library.

This library was screened using cultivated rose DFR cDNA (Plant and Cell Physiology, 36, 1023-1031, 1995) to obtain plaque indicating a signal. Plasmid pSFK710 was obtained by in vivo excision from this plaque using the method recommended by the manufacturer (Novagen). This plasmid contained a DNA sequence that closely coincided with the aforementioned cultivated rose DFR cDNA.

By carrying out PCR so as to obtain a 5'-untranslated region of a DFR translated sequence from this plasmid and facilitate coupling with heterologous genes, one of the EcoRI recognition sequences was mutated to an NheI recognition sequence followed by the addition of HindIII and BamHI recognition sequences. First, PCR was carried out in 50 μL of the reaction mixture using pSLF710 as template, using 25 pmol each of primers DFRproHindIIIF (5'-TAATAAGCT-TACAGTGTAATTATC-3', SEQ ID NO. 20) and DFRproN-heIR (5'-TTATGCTAGCGTGTCAAGACCAC-3', SEQ ID NO. 21), and using enzyme ExTaq DNA Polymerase (Toyobo). The PCR reaction conditions consisted of reacting for 5 minutes at 94° C. followed by repeating 30 cycles of a reaction of which one cycle consists of reacting for 30 seconds at 94° C., 30 seconds at 50° C. and 30 seconds at 72° C., and finally holding for 7 minutes at 72° C. As a result, a roughly 350 bp DNA fragment A was obtained. Similarly, a PCR reaction was carried out in 50 μL of the reaction mixture using pSFL710 as template, using 25 pmol each of primers DFRproNheIF (5'-ACACGCTAGCATAAGTCTGTTG-3', SEQ ID NO. 22) and DFRproBamHI-R (5'-GCTTGGG-GATCCATCTTAGG-3', SEQ ID NO. 23), and using enzyme ExTaq DNA Polymerase (Toyobo). The PCR reaction conditions consisted of reacting for 5 minutes at 94° C. followed by repeating 30 cycles of a reaction of which one cycle consists of reacting for 30 seconds at 94° C., 30 seconds at 50° C. and 30 seconds at 72° C., and finally holding for 7 minutes at 72° C. As a result, a 600 bp DNA fragment B was obtained.

The pSPB567 described in Patent Document 4 (plasmid pUC containing CaMV35S promoter to which has been added E12 enhancer, pansy F3'5'HBP#40 and nopaline synthase terminator) was digested with BamHI and then partially digested with HindIII to couple fragment A with a fragment digested with HindIII and NheI and couple fragment B with a fragment digested with NheI and BamHI and obtain plasmid pSLF721 (containing an expression cassette of R. rugosa DFR 5':BPF3'5'H#40:nos3'. An expression cassette obtained by digesting this plasmid with PacI was introduced into the PacI site of pBinPLUS to obtain pSLF724. This plasmid was then transfected into *Agrobacterium tumefaciens* strain EHA105.

A recombinant chrysanthemum was obtained from variety 94-765 using this transformed *Agrobacterium*. The resulting strain produced delphinidin in the flower petals thereof at about 0.6% of the total amount of anthocyanidins.

In addition, other reference examples using Rugosa rose DFR promoter are shown in the second row from the top (pSPB3316 (Rugosa rose DFRpro:pansy #40+rose ANSpro: torenia 5GT, non-delphinidin-producing strain) and in the fifth row from the top (Rugosa rose DFRpro:pansy #40+ Japanese gentian 3'GTpro::torenia MT, maximum delphinidin production level: 0.9%) of Table 1. Neither of these reference examples resulted in a change in flower color.

Reference Example 6

Production of Delphinidin in Chrysanthemum Using Rugosa Rose F3H Promoter

The Rugosa rose genomic DNA library produced in Reference Example 5 was screened with torenia flavanone 3-hydroxylase (F3H) cDNA (NCBI No. AB211958) to obtain plaques indicating signals. One of these plaques was converted to a plasmid in the same manner as Reference Example 5. This was then digested with restriction enzyme SpeI to recover a 2.6 kb DNA fragment, and plasmid pSPB804 was obtained by sub-cloning this DNA fragment to the SpeI site of pBluescript SKII-(Stratagene). This plasmid had a nucleotide sequence that demonstrates homology with F3H.

In order to amplify the 5'-untranslated region of F3H, PCR was carried out in 50 µL of a reaction mixture by using 1 ng of pSPB804 as template, using primer RrF3H-F (5'-AAGCT-TCTAGTTAGACAAAAAGCTA-3', SEQ ID NO. 24) and primer RrF3H (5'-GGATCCTCTCTTGATATTTCCGTTC-3', SEQ ID NO. 25), and using Ex-Taq DNA Polymerase (Toyobo). PCR reaction conditions consisted of reacting for 5 minutes at 94° C., repeating 30 cycles of reaction of which one cycle consisted of 30 seconds at 94° C., 30 seconds at 50° C. and 30 seconds at 72° C., and finally holding for 7 minutes at 72° C. The resulting DNA fragment was inserted into pCR-TOPO (Invitrogen) to obtain plasmid pSPB811. A roughly 2.1 kb F3H 5'-untranslated region was able to be recovered from this plasmid using HindIII and BamHI. Plasmid pSFL814 (containing R. rugosa F3H 5':BFP3'5'#40:nos 3') was obtained by substituting the promoter portion of pSPB567 with the roughly 1.2 kb 5'-untranslated region of F3H using HindIII and BamHI as described in Reference Example 5. This plasmid was intoduced into *Agrobacterium tumefaciens* strain EHA105.

Although three strains of recombinant chrysanthemum were obtained from variety 94-765 using this transformed *Agrobacterium*, there were no strains in which production of delphinidin was observed in the flower petals (see Table 1).

Reference Example 7

Production of pBINPLUS Rugosa Rose
F3Hpro:ADHNF-Pansy-F3'5'H#40::NOSter

A DNA fragment amplified by PCR using pSLF814 (Reference Example 6) as template and using ADH-BP40-Fd (5'-CAAGAAAAATAAATGGCAATTCTAGTCACCGAC-3', SEQ ID NO. 26) and NcoI-BP40-Rv (5'-CTCGAGCG-TACGTGAGCATC-3', SEQ ID NO. 27) as primers, and a DNA fragment amplified by PCR using pB1221 ADH-221 as template and using BamHI-ADH-Fd (5'-CGCGGATC-CGTCTATTTAACTCAGTATTC-3', SEQ ID NO. 28) and BP40-ADH-Rv (5'-TAGAATTGCCATTTATTTTTCT-TGATTTCCTTCAC-3', SEQ ID NO. 29) as primers were mixed, and a DNA fragment in which tobacco ADH-5'UTR 94 bp was directly coupled to the start codon of pansy F3'5'H#40 was obtained by PCR using this mixture of DNA fragments as template and using BamHI-ADH-Fd (5'-CGCGGATCCGTCTATTTAACTCAGTATTC-3', SEQ ID NO. 30) and NcoI-BP40-Rv (5'-CTCGAGCGTACGTGAG-CATC-3', SEQ ID NO. 31) as primers.

After TA-cloning this DNA fragment to pCR2.1, a roughly 600 bp DNA fragment obtained by digesting with BamHI and NcoI and a binary vector fragment obtained by digesting pSFL814 with BamHI and NcoI were ligated to obtain pBinPLUS Rugosa rose F3Hpro:ADHNF-pansy-F3'5'H#40:: Noster. This plasmid was introduced into *Agrobacterium tumefaciens* strain EHA105.

There were no individuals in which delphinidin was detected among four strains of transformants derived from chrysanthemum variety 94-765 obtained by using this transformed *Agrobacterium* (see Table 1).

Reference Example 8

Production of pBIN19 Rose
CHSpro:ADH-pansy-F3'5'H#18::NOSter

A DNA fragment amplified by PCR using pB1221 ADH221 as template and using ADH KpnI Forward (5'-CGGTACCGTCTATTTAACTCAGTATTC-3', SEQ ID NO. 32) and GUS19R (5'-TTTCTACAGGACGTAACAT-AAGGGA-3', SEQ ID NO. 33) as primers was digested with KpnI and SmaI to obtain a roughly 110 bp tobacco ADH-5'UTR DNA fragment. This DNA fragment was ligated with a binary vector DNA fragment obtained by digesting pBRBP18 (having an expression cassette of rose CHSpro:: pansy-F3'5'H#18::NOSter inserted into pBIN19) with KpnI and SmaI to obtain pBIN19 rose CHSpro::ADH-pansy-F3'5'H#18:NOSter. In this plasmid, a 38 bp spacer is present between tobacco ADH-5'UTR and pansy F3'5'H#18. This plasmid was introduced into *Agrobacterium tumefaciens* strain EHA105.

30 strains of recombinant chrysanthemum derived from chrysanthemum variety 94-765 were obtained using this transformed *Agrobacterium*. Delphinidin was detected in the petals of five of these strains and delphinidin content reached 1.9%. However, there were no changes in flower color observed.

Reference Example 9

Production of pBI121-rose
CHSpro::ADHNF-pansy-F3'5'H#40::NOSter

A DNA fragment obtained by PCR using pBRBP18 (Reference Example 3) as template, using HAPS-RhCHSpro3k-Fd (5'-CCAAGCTTGGCGCGCCTTAATTAAATT-TAAATCAGCAAGAGTTGAAGAAATAG-3', SEQ ID NO. 85) and NS-RhCHSpro3k-Rv (5'-AAAGCTAGCACTAGT-CATCTCGGAGAAGGGTCG-3', SEQ ID NO. 86) as primers, and using Pyrobest Polymerase (Takara), and a binary vector fragment obtained by digesting with HindIII and NheI and digesting pBI121 ADHNF with HindIII and XbaI were ligated, and the resulting binary vector was designated pBI121-RhCHSp-GUS-NOSt.

An ADHNF-pansy-F3'5'H#40 DNA fragment obtained by digesting the pCR-ADHBP40-SpeSac obtained in Example 10 with SpeI and EcoICRI was ligated to a binary vector fragment obtained by digesting pBI121-RhCHSp-GUS-NOSt with SpeI and EcoICRI to obtain pBI121-rose CHSpro::ADHNF-pansy-F3'5'H#40:: NOSter, which was used to transform *Agrobacterium tumefaciens* strain EHA105.

Although 19 strains of recombinant chrysanthemum derived from chrysanthemum variety 94-765 were obtained using this transformed *Agrobacterium*, there were no individuals in which delphinidin was detected.

Example 1

Cloning of the Promoter Region of Chrysanthemum
Flavanone 3-Hydroxylase Gene

The cloned promoter region of the chrysanthemum flavanone 3-hydroxylase gene, F3Hpro1K, has the nucleic acid sequence depicted in SEQ ID NO: 34. A promoter region having a different length was amplified in the manner described below. This portion of the chrysanthemum flavanone 3-hydroxylase gene, F3Hpro500, has the nucleic acid sequence depicted in SEQ ID NO: 87.

A DNA fragment amplified by PCR using pBluescript SK-gF3H9 as template and using HANS-F3Hpro-500Fd (5'-CCAAGCTTGGCGCGCCGCGGCCGCATTTAAAT TACTGTTCGAACCTACAAAGG-3', SEQ ID NO. 83, underline indicates sequence that anneals with DNA containing F3H promoter region) and MX-F3Hpro-Rv (5'-TTTCTA-GAACGCGTTTTTTATTTTTTCTTCACACACTTG-3', SEQ ID NO. 84, underline indicates sequence that anneals with DNA containing F3H promoter region) as primers was cloned into pCR2.1 to obtain pCR HANS-CmF3Hpro500-X. In addition, a binary vector fragment obtained by digesting pBI121 ADHNF with HindIII and XbaI and a roughly 500 bp chrysanthemum F3H promoter DNA fragment obtained by digesting pCR HANS-CmF3Hpro500-X with HindIII and XbaI were ligated to obtain pBI121 HANS-CmF3Hp500-X.

Example 2

Production of pBI121 Chrysanthemum F3Hpro1k::ADHNF-Bellflower F3'5'H::NOSter

Two types of primers consisting of CamF1 (5'-GT-GAAGCCACCATGTCTATAG-3', SEQ ID NO. 49) and CamR1 (5'-GCATTTGCCTAGACAGTGTAAG-3', SEQ ID NO. 50) were synthesized based on the translated sequence of F3'5'H cDNA (Accession No. D14590) of bellflower (Campanula medium) registered in the GenBank DNA database. RNA was extracted from the flower petals of commercially available bellflower buds using the RNeasy Mini Plant Kit (Qiagen), and 1st strand DNA was synthesized using an RT-PCR kit. PCR was carried out using primers by using this 1st strand DNA as template. The resulting DNA fragment was cloned into pCR-TOPO II. The nucleotide sequence of the resulting clone #4 (designated as pSPB2561) was determined to be SEQ ID NO. 51.

Figure 4:
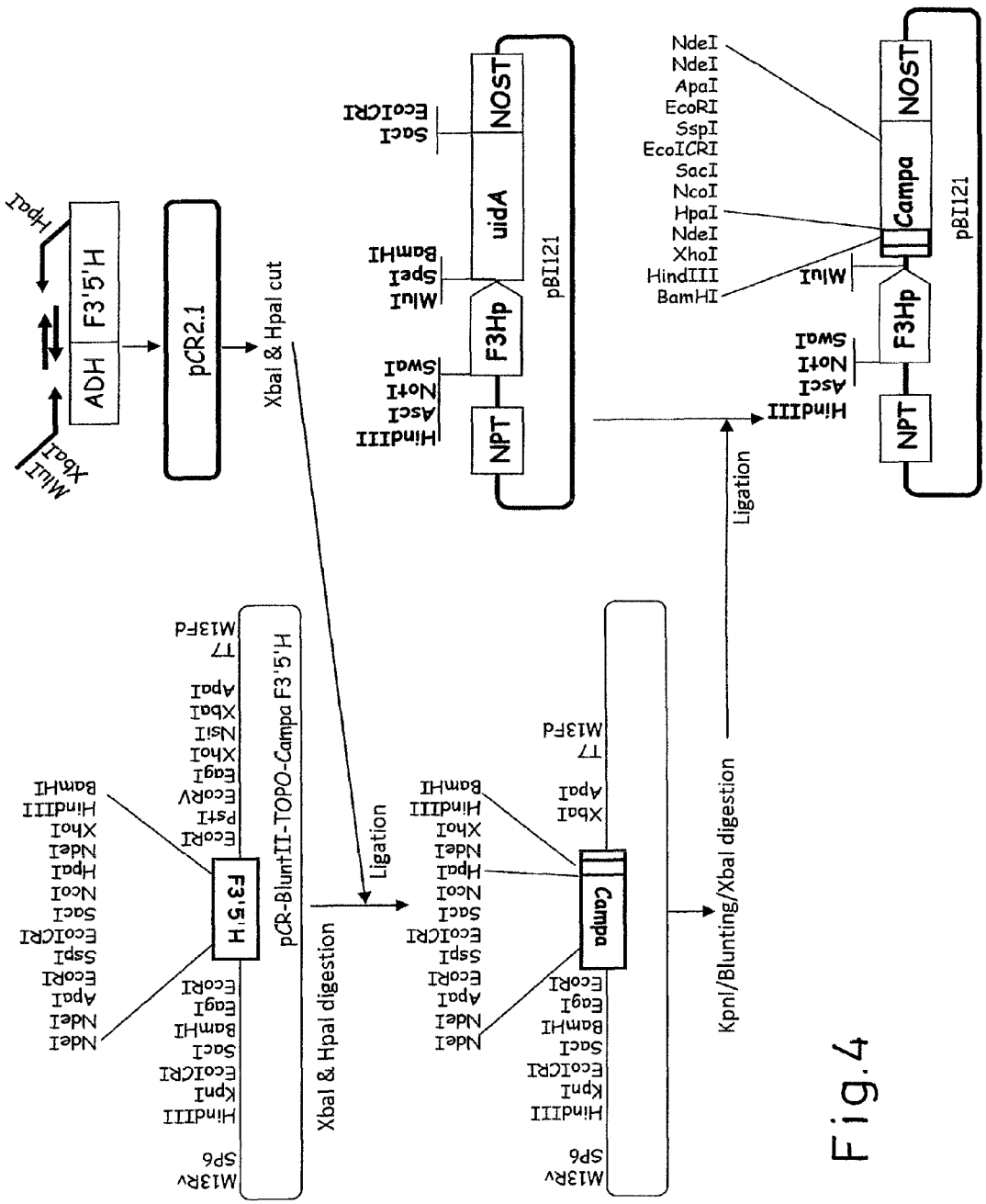
FIG. 4 indicates the construction process of pBI121 chrysanthemum F3Hpro1k::ADHNF-bellflower F3'5'H::NOSter.

A vector obtained by coupling tobacco ADH-5'UTR 94 bp and F3'5'H gene was constructed in the manner described below (FIG. 4). Furthermore, the same procedure was also carried out in the subsequently described examples.

Two types of DNA fragments consisting of a DNA fragment amplified by PCR using pSPB2561 as template and using ADH-Campa-Fd (5'-CAAGAAAAATAAATGTC-TATAGACATAACCATTC-3', SEQ ID NO. 53) and HpaI-Campa-Rv (5'-GTTAACATCTCTGGCACCACC-3', SEQ ID NO. 54) as primers and a DNA fragment amplified by PCR using pBI121 ADH-221 as template and using XbaI-ADH-Fd (SEQ ID NO. 42) and Campa-ADH-Rv (5'-GTCTATA-GACATTTATTTTTCTTGATTTCCTTCAC-3', SEQ ID NO. 55) as primers, were synthesized, and a DNA fragment in which tobacco ADH-5'UTR 94 bp is directly coupled to the start codon of bellflower F3'5'H was obtained by PCR using these two types of DNA fragments as templates and using XbaI-ADH-Fd (SEQ ID NO. 42) and HpaI-Campa-Rv (5'-GTTAAC ATCTCTGGCACCACC-3', SEQ ID NO. 56) as primers. This DNA fragment was then TA-cloned into pCR2.1 followed by digesting with XbaI and HpaI, and the resulting roughly 650 bp fragment was ligated with a vector fragment obtained by digesting pSPB2561 with XbaI and HpaI to obtain pCR ADHNF-Campanula F3'5'H.

Next, pCR ADHNF-Campanula F3'5'H was digested with KpnI followed by blunting with Blunting High (Toyobo) and digesting with XbaI, and the resulting roughly 1.7 kb DNA fragment was ligated with a binary vector fragment obtained by digesting pBI121 HANS-CmF3Hp1k-S with SpeI and EcoICRI to obtain pBI121 chrysanthemum F3Hpro1k::ADHNF-bellflower F3'5'H::NOSter. This plasmid was introduced into *Agrobacterium tumefaciens* strain EHA105.

48 recombinant chrysanthemum strains of chrysanthemum variety 94-765 were obtained by using this transformed *Agrobacterium*. Delphinidin was detected in the flower petals of 30 of these strains, and the delphinidin content reached 80.5%.

pSPB3738 was constructed from pBI121 chrysanthemum F3Hpro1k::ADHNF-bellflower F3'5'H::NOSter. This plasmid was transfected into *Agrobacterium tumefaciens* strain AGL0, and this was then used to transform the chrysanthemum variety Sei Taitan (Seikoen). Among the resulting 26 strains of recombinant chrysanthemums, a change in flower color was observed in 6 strains, and delphinidin was able to be detected by thin layer chromatography.

Example 3

Production of pIG121-Hm-chrysanthemum F3Hpro1k::ADHNF-Lisianthus F3'5'H::NOSter

Eustoma F3'5'H gene (EgF3'5'H, GenBank AB078957) cloned into pBluescript SK- was digested with XhoI followed by blunting with Blunting High (Toyobo), and the roughly 1.9 kb EgF3'5'H DNA fragment obtained by further digesting with XbaI was ligated to a pIG121-Hm binary vector obtained by digesting with XbaI and EcoICRI to obtain pIG121-Hm 35S::EgF3'5'H.

Next, two types of DNA fragments consisting of a DNA fragment amplified by PCR using pBluescript SK-EgF3'5'H as template and using ADH-EgF3'5'H-Fd (5'-CAA-GAAAAATAAAT GGCTGTTGGAAATGGCGTT-3', SEQ ID NO. 40) and HpaI-EgF3'5'H-Rv (5'-GTTAACGCT-GAGCCTAGTGCC-3', SEQ ID NO. 41) as primers, and a DNA fragment amplified by PCR using pBI221 ADH-221 (Satoh, J. et al. (2004), J. Biosci. Bioengineer) as template and using XbaI-ADH-Fd (5'-ACGCGTTCTAGAGTCTATT-TAACTCAGTATTC-3', SEQ ID NO. 42) and EgF3'5'H-ADH-Rv (5'-TCCAACAGCCATTTATTTTTCT-TGATTTCCTTCAC-3', SEQ ID NO. 43) as primers, were mixed, and a DNA fragment in which tobacco ADH-5'UTR 94 bp (Satoh, J. et al. (2004), J. Biosci. Bioengineer) was directly coupled to the start codon of EgF3'5'H was obtained by PCR using the mixture of DNA fragments as template and using XbaI-ADH-Fd (SEQ ID NO. 42) and HpaI-EgF3'5'H-Rv (5'-GTTAACGCTGAGCCTAGTGCC-3', SEQ ID NO. 44) as primers. After cloning this DNA fragment into pCR2.1, a roughly 1.3 kb DNA fragment obtained by digesting with XbaI and HpaI and a binary vector fragment obtained by digesting pIG121-Hm 35S::EgF3'5'H with XbaI and HpaI were ligated to obtain pIG121-Hm 35S::ADHNF-EgF3'5'H. A roughly 1.2 kb EgF3'5'H DNA fragment obtained by digesting this pIG121-Hm 35S::EgF3'5'H with HindIII and XbaI, a roughly 15 kb binary vector DNA fragment, and a DNA fragment obtained by further digesting pCR HANS-CmF3Hp1k-MNS with HindIII and SpeI were ligated to obtain PIG121-Hm chrysanthemum F3Hpro1k::ADHNF-lisianthus F3'5'H::NOSter. This plasmid was introduced into *Agrobacterium tumefaciens* strain EHA105.

Five recombinant chrysanthemum strains derived from chrysanthemum variety 94-765 by using this transformed *Agrobacterium*. Delphinidin was detected in the flower petals of one of these strains, and the delphinidin content was 4.4%.

Example 4

Production of pBI121 Chrysanthemum F3Hpro1k::ADHNF-Lobelia F3'5'H::NOSter

F3'5'H gene derived from the flower petals of lobelia cloned into pBluescript SK- (LeF3'5'H1, GenBank ABS221077 and LeF3'5'H4, GenBank AB221078) was digested with KpnI followed by blunting with Blunting High (Toyobo), and a roughly 1.9 kb EgF3'5'H DNA fragment obtained by further digesting with XbaI was ligated to a pIG121-Hm binary vector fragment obtained by digesting XbaI and EcoICRI to obtain pIG121-Hm 35S::LeF3'S'H1 and pIG121-Hm 35S::LeF3'5'H4.

Next, two types of DNA fragments consisting of a DNA fragment amplified by PCR using pBluescript SK-LeF3'5'H1 or pBluescript SK-LeF3'5'H4 as template and using ADH-LeF3'5'H-Fd (5'-CAAGAAAATAAATGGACGCGA-CAWACATTGC-3', SEQ ID NO. 45) and HpaI-LeF3'5'H-Rv (5'-GTTAACATCTCGGGCAGCACC-3', SEQ ID NO. 46) as primers, and a DNA fragment amplified by PCR using pBI121 ADH-221 as template and using XbaI-ADH-Fd (SEQ ID NO. 42) and LeF3'5'H-ADH-Rv (5'-TGTCGCGTC-CATTTATTTTTCTTGATTTCCTTCAC-3', SEQ ID NO. 47) as primers, were mixed, and DNA fragments in which tobacco ADH-5'UTR 94 bp was directly coupled to the start codon of LeF3'5'H1 or LeF3'5'H4 were respectively obtained by using this mixture of DNA fragments as template and using XbaI-ADH-Fd (SEQ ID NO. 42) and HpaI-LeF3'5'H-Rv (5'-GTTAACATCTCGGGCAGCACC-3', SEQ ID NO. 48) as primers.

After respectively TA-cloning these DNA fragments into pCR2.1, a DNA fragment obtained by digesting with XbaI and HpaI and a binary vector fragment obtained by digesting pIG121-Hm 35S::LeF3'5'H1 or pIG12'-Hm 35S::LeF3'5'H4 with XbaI and HpaI were respectively ligated to obtain pIG121-Hm 35S:: ADHNF-LeF3'5'H1 and pIG121-Hm 35S::ADHNF-LeF3'5'H4. A roughly 2.6 kb ADHNF-LeF3'5'H1::NOSter DNA fragment obtained by digesting these binary vectors with XbaI and EcoRV was ligated with a binary vector fragment obtained by digesting pBI121 HANS-CmF3Hp1k-S with SpeI and EcoICRI to obtain pBI121 chrysanthemum F3Hpro1kpro::ADHNF-loberia F3'5'H1::NOSter and pBI121 chrysanthemum F3Hpro1kpro::ADHNF-eustoma F3'5'H4::NOSter.

Although 12 strains of recombinant chrysanthemum derived from chrysanthemum variety 94-765 were obtained by using *Agrobacterium* transformed with pBI121 chrysanthemum F3Hpro1kpro::ADHNF-loberia F3'5'H1::NOSter, there were no individuals obtained that contained delphinidin. In addition, although 34 strains of recombinant chrysanthemum derived from chrysanthemum variety 94-765 were obtained by using *Agrobacterium* transformed with pBI121 chrysanthemum F3Hpro1 kpro::ADHNF-loberia F3'5'H4::NOSter, there were also no individuals obtained that contained delphinidin.

Example 5

Production of pBINPLUS Chrysanthemum F3Hpro1k::ADHNF-Pansy-F3'5'H#40::NOSter pBinPLUS chrysanthemum F3Hpro1k::ADHNF-pansy F3'5'H#40:: NOSter was obtained by ligating a roughly 1.1 kb chrysanthemum F3H promoter DNA fragment obtained by digesting pCR HANS-CmF3Hp1k-BclI with AscI and BclI, and a binary vector fragment obtained by digesting pBin-PLUS Rugosa rose F3Hpro:: ADHNF-pansy F3'5'H#40:: NOSter with AscI and BamHI. This plasmid was introduced into *Agrobacterium tumefaciens* strain EHA105.

6 recombinant chrysanthemum strains derived from chrysanthemum variety 94-675 were obtained by using this transformed *Agrobacterium*. Delphinidin was detected in the flower petals of 4 of these strains, and the delphinidin content reached 26.8%.

Example 6

Production of pBI121 Chrysanthemum F3Hpro1k::ADHNF-Cineraria F3'5'H:NOSter and Transformation into Chrysanthemum Two types of DNA fragments consisting of a DNA fragment amplified by PCR using the cineraria F3'S'H (pSPB2774) obtained in Reference Example 2 as template and using ADH-ScF3'5'H-Fd (5'-CAAGAAAAATAAAT-GAGCATTCTAACCCTAATC-3', SEQ ID NO. 57) and NdeI-ScF3'5'H-Rv (5'-CATATGTTTAGCTCCA-GAATTTGG-3', SEQ ID NO. 58) as primers, and a DNA fragment amplified by PCR using pBI121 ADH-221 as template and using XbaI-ADH-Fd (SEQ ID NO. 42) and ScF3'5'H-ADH-Rv (5'-TAGAATGCTCATTTATTTTTCT-TGATTTCCTTCAC-3', SEQ ID NO. 59) as primers, were mixed, and a DNA fragment in which tobacco ADH-5'UTR 94 bp was directly coupled to the start codon of cineraria F3'S'H was obtained by PCR using this mixture of DNA fragments as template and using XbaI-ADH-Fd (SEQ ID NO. 42) and NdeI-ScF3'5'H-Rv (5'-CATATGTTTAGCTCCA-GAATTTGG-3', SEQ ID NO. 60) as primers. After TA-cloning this DNA fragment into pCR2.1, a DNA fragment obtained by digesting with XbaI and NdeI and a vector fragment obtained by digesting pSPB2774 with XbaI and NdeI were ligated to obtain pBluescript Sk⁻ ADHNF-cineraria F3'5'H.

Next, a roughly 1.7 kb DNA fragment obtained by digesting pBluescript Sk⁻ ADHNF-cineraria F3'5'H with XbaI and XhoI and a vector fragment obtained by digesting pCR2.1 with XbaI and XhoI were ligated to obtain pCR2.1 ADHNF-cineraria F3'5'H. pBI121 chrysanthemum F3Hpro1k::ADHNF-cineraria F3'5'H:: NOSter was then obtained by ligating a DNA fragment obtained by digesting this pCR2.1 ADHNF-cineraria F3'5'H with XbaI and EcoRV with a binary vector fragment obtained by digesting pBI121 HANS-CmF3Hp1k-S with SpeI and EcoICRI. This plasmid was introduced into *Agrobacterium* tumefaciens strain EHA105.

50 recombinant strains derived from Chrysanthemum variety 94-765 were obtained by using this transformed *Agrobacterium*. Delphinidin was detected in the flower petals of 37 of these strains, and the delphinidin content reached 36.2%.

Example 7

Production of pBI121 Chrysanthemum F3Hpro1k::ADHNF-Japanese gentian F3'5'H::NOSter Two types of DNA fragments consisting of a DNA fragment amplified by PCR using Japanese gentian F3'5'H cloned into pBluescript SK- (plasmid pG48 described in WO 2004/020637) as template and using ADH-Gentian-Fd (5'-CAA-GAAAAATAAATGTCACCCATTTACACCACCC-3', SEQ ID NO. 61) and SalI-Gentian F3'5'H-Rv (5'-GTCGACGC-TATTGCTAAGCC-3', SEQ ID NO. 62) as primers, and a DNA fragment amplified by PCR using pBI121 ADH-221 as template and using XbaI-ADH-Fd (SEQ ID NO. 42) and Gentian-ADH-Rv (5'-AATGGGTGACATTTATTTTTCT-TGATTTCCTTCAC-3', SEQ ID NO. 63) as primers, were mixed, and a DNA fragment in which tobacco ADH-5'UTR 94 bp was directly coupled to the start codon of Japanese gentian F3'5'H was obtained by using this mixture of DNA fragments as template and using XbaI-ADH-Fd (SEQ ID NO. 42) and SalI-Gentian F3'5'H-Rv (5'-GTCGACGCTAT-TGCTAAGCC-3', SEQ ID NO. 64) as primers. After TA-cloning this DNA fragment into pCR2.1, a roughly 400 bp DNA fragment obtained by digesting with XbaI and SalI and a vector fragment obtained by digesting pG48 with XbaI and SalI were ligated to obtain pBluescript SK-ADHNF-Japanese gentian F3'5'H.

Next, a roughly 1.8 kb DNA fragment obtained by digesting pBluescript SK-ADHNF-Japanese gentian F3'5'H with XbaI and XhoI and a vector fragment obtained by digesting pCR2.1 with XbaI and XhoI were ligated to obtain pCR2.1 ADHNF-Japanese gentian F3'5'H. pBI112 chrysanthemum F3Hpro1k::ADHNF Japanese gentian F3'5'H::NOSter was obtained by ligating a DNA fragment obtained by digesting this pCR2.1 ADHNF-Japanese gentian F3'5'H with XbaI and EcoRV and a binary vector fragment obtained by digesting pBI121 HANS-CmF3Hp1k-S with SpeI and EcoICRI. This plasmid was introduced into *Agrobacterium tumefaciens* strain EHA105.

Although 21 recombinant chrysanthemum strains derived from Chrysanthemum variety 94-765 were obtained by using this transformed *Agrobacterium*, there were no individuals obtained that contained delphinidin.

Example 8

Production of pBI121 Chrysanthemum F3Hpro1k::ADHNF-Verbena F3'5'H::NOSter

Two types of DNA fragments consisting of a DNA fragment amplified by PCR using verbena F3'5'H cloned into pBluescript SK- (pHVF7, Plant Biotechnology, 23, 5-11, 2006, DNA database accession no. ABA234898) as template and using ADH-Verbena-Fd (5'-CAAGAAAAATAAAT-GACGTTTTCAGAGCTTATAAAC-3', SEQ ID NO. 65) and NcoI-Verbena F3'5'H-Rv (5'-CCATGGAGTAAATCAG-CATCTC-3', SEQ ID NO. 66) as primers, and a DNA fragment amplified by PCR using pBI121 ADH-221 as template and using XbaI-ADH-Fd (SEQ ID NO. 42) and Verbena ADH-Rv (5'-TGAAAACGTCATTTATTTTTCT-TGATTTCCTTCAC-3', SEQ ID NO. 67) as primers, were mixed, and a DNA fragment in which tobacco ADH-5'UTR 94 bp was directly coupled to the start codon of verbena F3'5'H was obtained by PCR using the mixture of DNA fragments as template and using XbaI-ADH-Fd (SEQ ID NO. 42) and NcoI-Verbena F3'5'H-Rv (5'-CCATGGAGTAAAT-CAGCATCTC-3', SEQ ID NO. 68) as primers. After TA-cloning this DNA fragment into pCR2.1, pBluescript SK-ADHNF-verbena F3'5'H was obtained by ligating a roughly 700 b DNA fragment obtained by digesting with XbaI and NcoI and a vector fragment obtained by digesting pHVF7 with XbaI and NcoI.

Next, a 1.8 kb DNA fragment obtained by digesting pBluescript SK-ADHNF-verbena F3'5'H with XbaI and XhoI and a vector fragment obtained by digesting pCR2.1 with XbaI and XhoI were ligated to obtain pCR2.1 ADHNF-verbena F3'5'H. pBI121 chrysanthemum F3Hpro1k::ADHNF-verbena F3'5'H::NOSter was then obtained by ligating a DNA fragment obtained by digesting this pCR2.1 ADHNF-verbena F3'5'H with XbaI and EcoRV and a binary vector fragment obtained by digesting pBI121 HANS-CmF3Hk1k-S with SpeI and EcoICRI. This plasmid was introduced into *Agrobacterium tumefaciens* strain EHA105.

17 recombinant chrysanthemum strains derived from chrysanthemum variety 94-765 were obtained by using this transformed *Agrobacterium*. Delphinidin was detected in the flower petals of 11 of these strains, and the maximum delphinidin content was 28.4%.

Example 9

Production of pBI121 Chrysanthemum F3Hpro1k::ADHNF-Blue Snapdragon F3'5'H::NOSter A cDNA library was produced using mRNA obtained from the bud of a type of snapdragon (*Antirrhinum kelloggii*, blue snapdragon) using the Uni-ZAP XR Vector Kit (Stratagene) in accordance with the method recommended by the manufacturer. This library was screened according to the method described in Reference Example 2 to obtain two types of plasmids pSPB3145 and pSPB3146 respectively containing F3'5'H cDNA #1 (SEQ ID NO. 69) and F3'5'H cDNA #12 (SEQ ID NO. 71).

Two types of DNA fragments consisting of a DNA fragment amplified by PCR using pSPB3145 or pSPB3146 as template and using ADH-AkF3'5'H-Fd (5'-CAA-GAAAAATAAATGCAGATAATAATTCCGGTCC-3', SEQ ID NO. 73) and NsiI-AkF3'5'H-Rv (5'-ATGCATGTC-CTCTAACATGTATC-3', SEQ ID NO. 74) as primers, and a DNA fragment amplified by PCR using pBI121 ADH-221 as template and using XbaI-ADH-Fd (SEQ ID NO. 42) and AkF3'5'H-ADH-Rv (5'-TATTATCTGCATTTATTTTTCT-TGATTTCCTTCAC-3', SEQ ID NO. 75) as primers, were mixed, and a DNA fragment in which tobacco ADH-5'UTR 94 bp was directly coupled to the start codon of blue snapdragon (Ak)F3'5'H #1 or #12 was respectively obtained by PCR using the mixture of DNA fragments as template and using XbaI-ADH-Fd (SEQ ID NO. 42) and NsiI-AkF3'5'H-Rv (5'-ATGCATGTCCTCTAACATGTATC-3', SEQ ID NO. 76) as primers. After TA-cloning this DNA fragment to pCR2.1, pBluescript SK-ADHNF-AkF3'5'H #1 and #12 were obtained by respectively ligating a roughly 700 b DNA fragment obtained by digesting with XbaI and NsiI and a vector fragment obtained by digesting pSPB3145 (pBluescript SK-AkF3'S'H #1) and pSBP3146 (pBluescript SK-AkF3'S'H #12) with XbaI and NsiI.

Next, roughly 700 b DNA fragments obtained by digesting pBluescript SK-ADHNF-AkF3'S'H #1 and #12 with XbaI and XhoI were ligated with a vector fragment obtained by digesting pCR2.1 with XbaI and XhoI to obtain pCR2.1 ADHNF-AkF3'5'H #1 and #12. pBI121 chrysanthemum F3Hpro1k::ADHNF-AkF3'5'H#1::NOSter and pBI121 chrysanthemum F3Hpro1k::ADHNF-AkF3'5'H#12::NOSter were obtained by respectively ligating DNA fragments obtained by digesting these pCR2.1 ADHNF-AkF3'5'H #1 and #12 with XbaI and EcoRV with a binary vector fragment obtained by digesting pBI121 HANS-CmF3Hp1k-S with SpeI and EcoICRI. These plasmids were transfected into *Agrobacterium tumefaciens* strain EHA105.

1 strain of recombinant chrysanthemum derived from chrysanthemum variety 94-765 was obtained by using this transformed *Agrobacterium*. Delphinidin was detected in the flower petals of this strain, and the delphinidin content reached 2.9%.

Example 10

Production of pBI121 Chrysanthemum F3Hpro500::ADHNF-Cineraria F3'5'H::NOSter A binary vector DNA fragment obtained by digesting the pBI121 HANS-CmF3Hp500-X obtained in Example 1 with XbaI and EcoICRI and a DNA fragment of ADHNF-cineraria F3'5'H obtained by digesting the pCR2.1 ADHNF-cineraria F3'5'H obtained in Example 6 were ligated to obtain pBI121-chrysanthemum F3Hpro500::ADHNF-cineraria F3'5'H::NOSter, which was then introduced into *Agrobacterium tumefaciens* strain EHA105.

Seven stains of recombinant chrysanthemum derived from chrysanthemum variety Taihei were obtained by using this transformed *Agrobacterium*. Delphinidin was detected in 5 of those strains, and delphinidin content reached 25.5%.

INDUSTRIAL APPLICABILITY

According to the present invention, chrysanthemum flower color can be changed to blue by using the transcriptional regulatory region of chrysanthemum-derived flavanone 3-hydroxylase (F3H), expressing flavonoid 3'5'-hydroxylase (F3'5'H) in chrysanthemum, and allowing a large amount of delphinidin to accumulate in the flower petals. Although chrysanthemums come in flower colors including white, yellow, orange, red, pink and purplish red, since there are no existing varieties or closely related wild varieties that produce bluish flowers such as those having a purple or blue color, blue chrysanthemums produced according to the method of the present invention will lead to stimulation of new demand.

TABLE 1

Accumulation of Delphinidin in *Chrysanthemum* Transformants Introduced with Various F3'5'H Genes

| Gene Cassette 1 F3'5'H | | | | Gene Cassette 2 | | | No. of transformants | No. of individuals analyzed for aglycones | No. of individuals containing delphinidin | Delphinidin Content** Mean (%) | Maximum (%) | Example No. |
|---|---|---|---|---|---|---|---|---|---|---|---|---|
| Promoter | ADH enhancer* | F3'5'H gene origin | Terminator | Promoter | Gene | Terminator | | | | | | |
| Rugosa rose DFR | None | Pansy #40 | NOS | | | | 4 | 2 | 1 | 0.3 | 0.6 | Ref. Ex. 5 |
| Rugosa rose DFR | None | Pansy #40 | NOS | Rose ANS | *Torenia* 5GT | MAS | 2 | 1 | 0 | 0.0 | 0.0 | Ref. Ex. 5 |
| Rugosa rose F3H | None | Pansy #40 | NOS | | | | 3 | 3 | 0 | 0.0 | 0.0 | Ref. Ex. 6 |
| Rugosa rose F3H | 94 bp, direct coupled | Pansy #40 | NOS | | | | 4 | 2 | 0 | 0.0 | 0.0 | Ref. Ex. 7 |
| Rugosa rose DFR | None | Pansy #40 | NOS | Gentian 3GT | *Torenia* MT | MOS | 5 | 4 | 4 | 0.7 | 0.9 | Ref. Ex. 5 |
| Gerbera CHS | None | Pansy #18 | NOS | | | | 2 | 1 | 0 | 0.0 | 0.0 | Ref. Ex. 4 |
| Pansy #40 | None | Pansy #18 | NOS | *Perilla* 3AT | *Perilla* 3AT | *Perilla* 3AT | 6 | 6 | 4 | 0.6 | 1.4 | Ref. Ex. 4 |
| Rose CHS | None | Pansy #18 | NOS | | | | 11 | 10 | 5 | 1.3 | 5.4 | Ref. Ex. 3 |
| Rose CHS | None | Pansy #18 | NOS | Rose CHS | *Chrysanthemum* F3'H IR | NOS | 11 | 11 | 2 | 0.4 | 3.6 | Ref. Ex. 3 |
| Rose CHS | 94 bp, with spacer | Pansy #18 | NOS | | | | 30 | 29 | 5 | 0.2 | 1.9 | Ref. Ex. 8 |
| Rose CHS | 94 bp, direct coupled | Pansy #40 | NOS | | | | 19 | 19 | 0 | 0.0 | 0.0 | Ref. Ex. 9 |
| CaMV35S | 74 bp, with spacer | Pansy #40 | NOS | | | | 8 | 5 | 2 | 0.2 | 0.7 | Ex. 7 |
| CaMV35S | 74 bp, with spacer | Bellflower | NOS | | | | 11 | 9 | 9 | 1.5 | 6.9 | Ex. 4 |
| *Chrysanthemum* F3H1k | 94 bp, direct coupled | Gentian | NOS | | | | 21 | 19 | 0 | 0.0 | 0.0 | Ex. 4 |
| *Chrysanthemum* F3H1k | 94 bp, direct coupled | *Lobelia* #1 | NOS | | | | 12 | 11 | 0 | 0.0 | 0.0 | Ex. 9 |
| *Chrysanthemum* F3H1k | 94 bp, direct coupled | *Lobelia* #4 | NOS | | | | 34 | 20 | 0 | 0.0 | 0.0 | Ex. 3 |
| *Chrysanthemum* F3H1k | 94 bp, direct coupled | Blue snap-dragon | NOS | | | | 1 | 1 | 1 | 2.9 | 2.9 | Ex. 10 |
| *Chrysanthemum* F3H1k | 94 bp, direct coupled | *Eustoma* | NOS | | | | 5 | 5 | 1 | 0.9 | 4.4 | Ex. 5 |
| *Chrysanthemum* F3H1k | 94 bp, direct coupled | *Cineraria* | NOS | | | | 7 | 7 | 5 | 11.9 | 25.5 | Ex. 8 |
| *Chrysanthemum* F3H500 | 94 bp, direct coupled | Pansy #40 | NOS | | | | 6 | 5 | 4 | 14.9 | 26.8 | Ex. 6 |
| *Chrysanthemum* F3H1k | 94 bp, direct coupled | *Verbena* | NOS | | | | 17 | 12 | 11 | 8.9 | 28.4 | Ex. 2 |
| *Chrysanthemum* F3H1k | 94 bp, direct coupled | *Cineraria* | NOS | | | | 50 | 47 | 37 | 7.5 | 36.2 | |
| *Chrysanthemum* F3H1k | 94 bp, direct coupled | Bellflower | NOS | | | | 48 | 39 | 30 | 31.4 | 80.5 | |

*Length of 5'UTR of tobacco ADH gene and manner of coupling to start codon of F3'5'H gene
**Ratio of delphinidin to total anthocyanidins during hydrolysis of anthocyanin accumulated in ray petals (wt %) The number of transformants for which the delphinidin content was 0 was included when determining mean values.

The invention claimed is:

1. A method for producing a chrysanthemum plant containing delphinidin in the petals thereof comprising expressing flavonoid 3',5'-hydroxylase (F3'5'H) using a transcriptional regulatory region; wherein the chrysanthemum plant is transformed with an expression vector or expression cassette comprising a gene encoding F3'5'H and the transcriptional regulatory region; wherein the F3'5'H is derived from bellflower (campanula), cineraria, verbena, or pansy; and wherein the transcriptional regulatory region is
    a nucleic acid containing the nucleotide sequence indicated in SEQ ID NO: 34 or SEQ ID NO: 87.

2. The method according to claim 1, wherein a translation enhancer derived from tobacco alcohol dehydrogenase is further used in addition to the transcriptional regulatory region.

3. The method according to claim 2, wherein the translation enhancer is coupled directly to a start codon of the F3'5'H gene.

4. A chrysanthemum plant, or a progeny, a vegetative proliferation product, a part, or a tissue thereof, transformed by the method according to claim 1.

5. A chrysanthemum plant, or a progeny, a vegetative proliferation product, a part, or a tissue thereof according to claim 4, which is a cut flower.

6. A cut flower processed product made from the cut flower according to claim 5, wherein said cut flower processed product comprises a F3'5'H gene sequence from bellflower (campanula), cineraria, verbena, or pansy operably linked to a transcriptional regulatory sequence, and wherein the transcriptional regulatory region is
    a nucleic acid containing the nucleotide sequence indicated in SEQ ID NO: 34 or SEQ ID NO: 87.

7. The method according to claim 1, wherein the content of delphinidin in the petals is 25% by weight or more of the total weight of anthocyanidins, and wherein a translation enhancer derived from tobacco alcohol dehydrogenase is further used in addition to the transcriptional regulatory region.

8. The method according to claim 3, wherein the content of delphinidin in the petals is 25% by weight or more of the total weight of anthocyanidins.

\* \* \* \* \*